(12) United States Patent  
Orimoto et al.

(10) Patent No.: US 10,662,157 B2
(45) Date of Patent: May 26, 2020

(54) HETEROCYCLIC COMPOUND

(71) Applicant: Sumitomo Chemical Company, Limited, Tokyo (JP)

(72) Inventors: Kohei Orimoto, Takarazuka (JP); Takamasa Tanabe, Takarazuka (JP); Yoshihiko Nokura, Takarazuka (JP); Yuji Nakajima, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/091,364

(22) PCT Filed: Mar. 27, 2017

(86) PCT No.: PCT/JP2017/012289
§ 371 (c)(1),
(2) Date: Oct. 4, 2018

(87) PCT Pub. No.: WO2017/175613
PCT Pub. Date: Oct. 12, 2017

(65) Prior Publication Data
US 2019/0127328 A1 May 2, 2019

(30) Foreign Application Priority Data
Apr. 6, 2016 (JP) .................................. 2016-076517

(51) Int. Cl.
*C07D 401/04* (2006.01)
*C07D 213/71* (2006.01)
(Continued)

(52) U.S. Cl.
CPC ........... *C07D 213/71* (2013.01); *A01N 43/40* (2013.01); *A01N 43/58* (2013.01); *A01N 43/60* (2013.01);
(Continued)

(58) Field of Classification Search
CPC ................................................ C07D 401/04
(Continued)

(56) References Cited

U.S. PATENT DOCUMENTS

2003/0036544 A1 2/2003 Steiger et al.
2014/0199331 A1 7/2014 Robillard et al.
(Continued)

FOREIGN PATENT DOCUMENTS

EP 2499692 B1 7/2016
EP 3088392 A1 11/2016
(Continued)

OTHER PUBLICATIONS

Int'l Preliminary Report on Patentability dated Oct. 9, 2018 in Int'l Application No. PCT/JP2017/012289.
(Continued)

*Primary Examiner* — Patricia L Morris
(74) *Attorney, Agent, or Firm* — Panitch Schwarze Belisario & Nadel LLP

(57) ABSTRACT

A compound of formula (I), or an N-oxide thereof is provided. In the compound of formula (I), Het¹ represents Het¹-1, Het¹-2, Het¹-3, Het¹-4, Het¹-5, Het¹-6, Het¹-7, Het¹-8, or Het¹-9, and the remaining variable groups are as defined in the specification. The compound of formula (I), or N-oxide thereof has a superior effect in controlling arthropod pests.

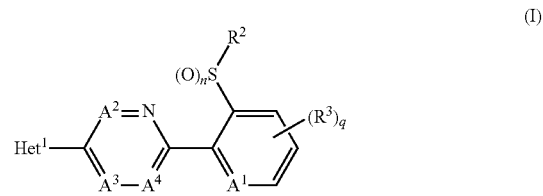

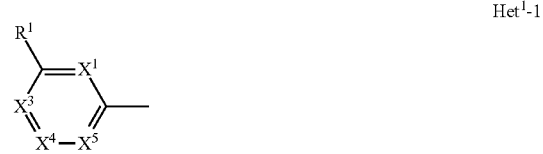

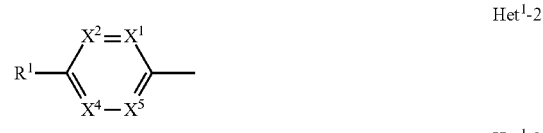

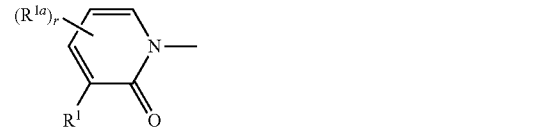

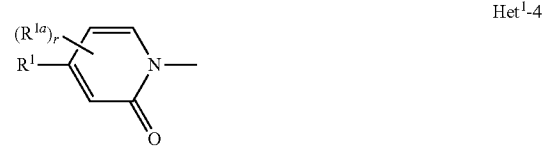

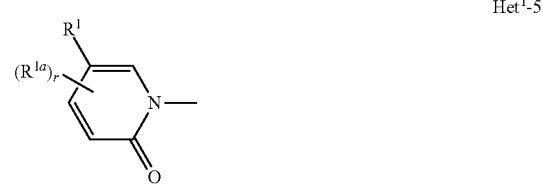

(Continued)

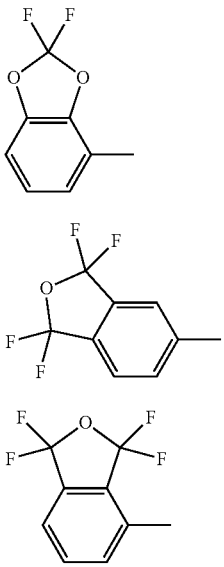

10 Claims, No Drawings

(51) Int. Cl.
    *A01N 43/40*         (2006.01)
    *A01N 43/60*         (2006.01)
    *C07D 401/14*       (2006.01)
    *A01N 43/58*         (2006.01)

(52) U.S. Cl.
    CPC ......... *C07D 401/04* (2013.01); *C07D 401/14* (2013.01)

(58) Field of Classification Search
    USPC ...................................... 544/238; 514/252.03
    See application file for complete search history.

(56) References Cited

U.S. PATENT DOCUMENTS

| 2018/0009778 A1 | 1/2018 | Tanabe et al. |
| 2018/0201600 A1 | 7/2018 | Jeschke et al. |
| 2018/0310559 A1 | 11/2018 | Tanabe et al. |

FOREIGN PATENT DOCUMENTS

| EP | 3135114 A1 | 3/2017 | |
| JP | 2002543191 A | 12/2002 | |
| JP | 2014515039 A | 6/2014 | |
| WO | 2000066568 A1 | 11/2000 | |
| WO | 2012156918 A1 | 11/2012 | |
| WO | 2014081300 A1 | 5/2014 | |
| WO | 2015163478 A1 | 10/2015 | |
| WO | 2016121969 A1 | 8/2016 | |
| WO | 2016121970 A1 | 8/2016 | |
| WO | WO-2016149315 A1 * | 9/2016 | ............. A01N 43/80 |
| WO | 2017005673 A1 | 1/2017 | |

OTHER PUBLICATIONS

Int'l Search Report dated May 30, 2017 in Int'l Application No. PCT/JP2017/012289.
Brooker, et al., Acaricidal 1,2,4,5-tetrazines. Pesticide Science. vol. 18, pp. 179-190, 1987.
Challis, et al., 1986 British Crop Protection Conference—Pests and Diseases, vol. 2, pp. 483-488, 1986.
Extended European Search Report dated Sep. 9, 2019 in EP Application No. 17778992.2.
Office Action dated Mar. 5, 2020 in IN Application No. 201847040947.

* cited by examiner

HETEROCYCLIC COMPOUND

CROSS-REFERENCE TO RELATED APPLICATION

This application is a Section 371 of International Application No. PCT/JP2017/012289, filed Mar. 27, 2017, which was published in the Japanese language on Oct. 12, 2017, under International Publication No. WO 2017/175613 A1, which claims priority under 35 U.S.C. § 119(b) to Japanese Application No. 2016-076517, filed Apr. 6, 2016, the disclosures of which are incorporated herein by reference in their entireties.

TECHNICAL FIELD

The present invention is related to a heterocyclic compound and an agent for controlling harmful arthropod comprising the same.

BACKGROUND ART

To date, some compounds for controlling harmful arthropods have been developed and come into practical use. Also, a certain class of compounds has been known to have an effect on controlling harmful arthropods (see, for example, Patent Document 1).

CITATION LIST

Patent Document

Patent Document 1: Pesticide Science, 1987, 18, 179-190

SUMMARY OF THE INVENTION

Problems to be Solved by Invention

An object of the present invention is to provide a compound having an excellent efficacy for controlling harmful arthropods.

Means to Solve Problems

The present invention provides the following embodiments.

[1] A compound represented by formula (I):

wherein $Het^1$ represents $Het^1$-1, $Het^1$-2, $Het^1$-3, $Het^1$-4, $Het^1$-5, $Het^1$-6, $Het^1$-7, $Het^1$-8, or $Het^1$-9:

$R^1$ represents $OR^4$, $OS(O)_2R^4$, $S(O)_mR^4$, $NR^5S(O)_2R$, a C1-C4 chain hydrocarbon group having one or more halogen atoms, or a halogen atom;

$R^4$ represents a C1-C4 chain hydrocarbon group having one or more halogen atoms;

$R^5$ represents a hydrogen atom, or a C1-C6 chain hydrocarbon group optionally having one or more halogen atoms;

$X^1$ represents a nitrogen atom, or $CR^{30}$;
$X^2$ represents a nitrogen atom, or $CR^{31}$;
$X^3$ represents a nitrogen atom, or $CR^{32}$;
$X^4$ represents a nitrogen atom, or $CR^{33}$;
$X^5$ represents a nitrogen atom, or $CR^{34}$;

$R^{30}$, $R^{31}$, $R^{32}$, $R^{33}$, and $R^{34}$ represent independently of each other a hydrogen atom, a C1-C6 chain hydrocarbon group optionally having one or more halogen atoms, a C3-C6 alicyclic group optionally having one or more halogen atoms, or a halogen atom, $R^{1a}$ represents a C1-C6 chain hydrocarbon group optionally having one or more halogen atoms, a C3-C6 alicyclic group optionally having one or more halogen atoms, or a halogen atom;

r is 0, 1, 2, or 3, and when r is 2 or 3, two or more $R^{1a}$ may be identical to or different from each other;

$A^1$ represents a nitrogen atom, or $CR^9$;

a combination of $A^2$, $A^3$, and $A^4$ represents a combination where $A^2$ represents $CR^6$, $A^3$ represents $CR^7$, and $A^4$ represents $CR^8$, a combination where $A^2$ represents a nitrogen atom, $A^3$ represents $CR^7$, and $A^4$ represents $CR^8$, a combination where $A^2$ represents $CR^6$, $A^3$ represents a nitrogen atom, and $A^4$ represents $CR^8$, or a combination where $A^2$ represents $CR^6$, $A^3$ represents $CR^7$, and $A^4$ represents a nitrogen atom;

$R^9$ represents a hydrogen atom, or a halogen atom;

$R^6$, $R^7$ and $R^8$ represent independently of each other a hydrogen atom, a C1-C6 chain hydrocarbon group optionally having one or more halogen atoms, a nitro group, $OR^{18}$, $NR^{18}R^{19}$, a cyano group, or a halogen atom;

n is 0, 1, or 2;

$R^2$ represents a cyclopropyl group, a cyclopropylmethyl group, or a C1-C6 alkyl group optionally having one or more halogen atoms;

q is 0, 1, 2, or 3;

$R^3$ represents a C1-C6 chain hydrocarbon group optionally having one or more substituents selected from Group B, a phenyl group optionally having one or more substituents selected from Group D, a five- or six-membered aromatic heterocyclic group optionally having one or more substituents selected from Group D, a nitro group, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)$ $NR^{15}R^{16}$, $NR^{24}NR^{11}C(O)$ $NR^{15}R^{16}$, $N=CHNR^{15}R^{16}$, $N=S(O)_xR^{15}R^{16}$, $S(O)_yR^{15}$, $C(O)OR^{17}$, $C(O)NR^{11}R^{12}$, a cyano group, or a halogen atom, and when q is 2 or 3, two or more $R^3$ is identical to or different from each other;

$R^{11}$, $R^{17}$, $R^{18}$, $R^{19}$ and $R^{24}$ represent independently of each other a hydrogen atom, or a C1-C6 chain hydrocarbon group optionally having one or more halogen atoms;

$R^{12}$ represents a hydrogen atom, $S(O)_2R^{23}$, a C1-C6 chain hydrocarbon group optionally having one or more halogen atoms, or a C1-C6 alkyl group having one substituent selected from Group F;

$R^{23}$ represents a C1-C6 chain hydrocarbon group optionally having one or more halogen atoms, or a phenyl group optionally having one or more substituents selected from Group D;

$R^{11a}$ and $R^{12a}$ combine together with a nitrogen atom to which they are attached to form a three- to seven-membered nonaromatic heterocyclic group optionally having one or more substituents selected from Group E {wherein said three- to seven-membered nonaromatic heterocyclic group represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, or a 1,4-thiazepane ring};

$R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a five- or six-membered aromatic heterocyclic group optionally having one or more substituents selected from Group D;

$R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group {wherein said phenyl moiety of the phenyl C1-C3 alkyl group may optionally have one or more substituents selected from Group D];

$R^{15}$ and $R^{16}$ represent independently of each other a C1-C6 alkyl group optionally having one or more halogen atoms;

m is 0, 1, or 2;

x is 0 or 1;

y is 0, 1, or 2;

Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom;

Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, $NHR^{21}$, $NR^{21}R^{22}$, $C(O)R^{21}$, $OC(O)R^{21}$, $C(O)OR^{21}$, a cyano group, a nitro group, and a halogen atom (wherein said $R^{21}$ and $R^{22}$ represent independently of each other a C1-C6 alkyl group optionally having one or more halogen atoms);

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C1-C6 alkoxy group optionally having one or more halogen atoms, an amino group, $NHR^{21}$, $NR^{21}R^{22}$, a cyano group, a phenyl group optionally having one or more substituents selected from Group D, a five- or six-membered aromatic heterocyclic group optionally having one or more substituents selected from Group D, a C3-C7 cycloalkyl group optionally having one or more halogen atoms, and a three- to seven-membered nonaromatic heterocyclic group optionally having one or more substituents selected from Group C {wherein said three- to seven-nonaromatic heterocyclic group represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, or a 1,4-thiazepane ring}]
or an N-oxide compound thereof
(hereinafter, the compound represented by formula (I) or the N-oxide compound is referred to as "Present compound" or "Compound of the present invention").

[2] The compound according to [1] wherein a combination of $A^2$, $A^3$ and $A^4$ represents a combination where $A^2$ represents $CR^6$, $A^3$ represents $CR^7$, and $A^4$ represents $CR^8$, a combination where $A^2$ represents a nitrogen atom, $A^3$ represents $CR^7$, and $A^4$ represents $CR^8$, or a combination where $A^2$ represents $CR^6$, $A^3$ represents a nitrogen atom, and $A^4$ represents $CR^8$.

[3] The compound according to [1] wherein a combination of $A^2$, $A^3$ and $A^4$ represents a combination wherein $A^2$ represents $CR^6$, $A^3$ represents $CR^7$, and $A^4$ represents $CR^8$.

[4] The compound according to [1] wherein a combination of $A^2$, $A^3$ and $A^4$ represents a combination wherein $A^2$ represents a nitrogen atom, $A^3$ represents $CR^7$, and $A^4$ represents $CR^8$.

[5] The compound according to claim 1 wherein a combination of $A^2$, $A^3$ and $A^4$ represents a combination wherein $A^2$ represents $CR^6$, $A^3$ represents a nitrogen atom, and $A^4$ represents $CR^8$.

[6] The compound according to any one of [1] to [5] wherein $Het^1$ represents $Het^1$-1 or $Het^1$-2.

[7] The compound according to any one of [1] to [5] wherein $Het^1$ represents $Het^1$-3, $Het^1$-4 or $Het^1$-5.

[8] The compound according to any one of [1] to [5] wherein $Het^1$ represents $Het^1$-6, or $Het^1$-7.

[9] The compound according to any one of [1] to [5] wherein $Het^1$ represents $Het^1$-8, or $Het^1$-9.

[10] The compound according to any one of [1] to [9] wherein $R^3$ represents a C1-C6 alkyl group optionally having one or more halogen atoms, a phenyl group optionally having one or more substituents selected from Group G, a five membered aromatic heterocyclic group containing one to four nitrogen atoms, a six membered aromatic heterocyclic group containing one to two nitrogen atoms, $NR^{11}R^{12}$, $NR^{24}NR^{11}R^{12}$ or a halogen atom,
Group G: a group consisting of a halogen atom and a C1-C6 haloalkyl group.

[11] The compound according to any one of [1] to [9] wherein $R^3$ represents a C1-C6 alkyl group optionally having one or more halogen atoms, or a halogen atom.

[12] The compound according to any one of [1] to [11] wherein $R^2$ represents an ethyl group.

[13] The compound according to [1] wherein $A^1$ represents a nitrogen atom, or CH; a combination of $A^2$, $A^3$ and $A^4$ represents a combination where $A^2$ represents $CR^6$, $A^3$ represents $CR^7$, and $A^4$ represents $CR^8$, a combination where $A^2$ represents a nitrogen atom, $A^3$ represents $CR^7$, and $A^4$ represents $CR^8$, or a combination where $A^2$ represents $CR^6$, $A^3$ represents a nitrogen atom, and $A^4$ represents $CR^8$; $R^1$ represents a C1-C4 chain hydrocarbon group having one or more halogen atoms, or a halogen atom; $R^2$ represents a methyl group, or an ethyl group; and $R^3$ represents a C1-C6 alkyl group optionally having one or more halogen atoms, a phenyl group optionally having one or more substituents selected from Group G, a five membered aromatic heterocyclic group containing one to four nitrogen atoms (wherein said five membered aromatic heterocyclic group may optionally have one or more substituents selected from Group G), a six membered aromatic heterocyclic group containing one to two nitrogen atoms (wherein said six membered aromatic heterocyclic group may optionally have one or more substituents selected from Group G), $NR^{11}R^{12}$, $NR^{24}NR^{11}R^{12}$, or a halogen atom; $R^{11}$, $R^{12}$ and $R^{24}$ represent independently of each other a hydrogen atom, a C1-C3 alkyl group optionally having one or more halogen atoms; $R^6$, $R^7$ and $R^8$ represent independently of each other a C1-C6 alkyl group optionally having one or more halogen atoms, or a halogen atom; $Het^1$ represents $Het^1$-1 or $Het^1$-2; and q is 0 or 1;
Group G: a group consisting of a halogen atom and a C1-C6 haloalkyl group.

[14] The compound according to [1] wherein $A^1$ represents a nitrogen atom, or CH; a combination of $A^2$, $A^3$ and $A^4$ represents a combination where $A^2$ represents $CR^6$, $A^3$ represents $CR^7$, and $A^4$ represents $CR^8$, a combination where $A^2$ represents a nitrogen atom, $A^3$ represents $CR^7$, and $A^4$ represents $CR^8$, or a combination where $A^2$ represents $CR^6$, $A^3$ represents a nitrogen atom, and $A^4$ represents $CR^8$; $R^1$ represents a C1-C4 chain hydrocarbon group having one or more halogen atoms, or a halogen atom; $R^2$ represents a methyl group, or an ethyl group; $R^3$ represents a C1-C6 alkyl group optionally having one or more halogen atoms, a phenyl group optionally having one or more substituents selected from Group G, a five membered aromatic heterocyclic group containing one to four nitrogen atoms (wherein said five membered aromatic heterocyclic group may optionally have one or more substituents selected from Group G), a six membered aromatic heterocyclic group containing one to two nitrogen atoms (wherein said six membered aromatic heterocyclic group may optionally have one or more substituents selected from Group G), $NR^{11}R^{12}$, $NR^{24}NR^{11}R^{12}$, or a halogen atom; $R^{11}$, $R^{12}$ and $R^{24}$ represent independently of each other a hydrogen atom, a C1-C3 alkyl group optionally having one or more halogen atoms; $R^6$, $R^7$ and $R^8$ represent independently of each other a hydrogen atom, a C1-C6 alkyl group optionally having one or more halogen atoms, or a halogen atom; and $Het^1$ represents $Het^1$-1 or $Het^1$-2; and q is 0 or 1;
Group G: a group consisting of a halogen atom and a C1-C6 haloalkyl group.

[15] The compound according to [1] wherein $A^1$ represents a nitrogen atom, or CH; a combination of $A^2$, $A^3$, and $A^4$ represents a combination where $A^2$ represents CH, $A^3$ represents CH, and $A^4$ represents CH, a combination where $A^2$ represents a nitrogen atom, $A^3$ represents CH, and $A^4$ represents CH, a combination where $A^2$ represents CH, $A^3$ represents a nitrogen atom, and $A^4$ represents CH; $R^1$ represents a C1-C4 chain hydrocarbon group having one or more halogen atoms, or a halogen atom; $R^2$ represents an ethyl group; q is 0 or 1; $R^3$ represents a C1-C6 alkyl group optionally having one or more halogen atoms, or a halogen atom; and $Het^1$ represents $Het^1$-1.

[16] A composition for controlling a harmful arthropod comprising the compound according to any one of [1] to [15] and an inert carrier.

[17] A method for controlling a harmful arthropod, said method comprising applying an effective amount of the compound according to any one of [1] to [15] to a harmful arthropod or a habitat where a harmful arthropod lives.

[18] A composition comprising one or more ingredients selected from the group consisting of the following Group (a), Group (b), Group (c), and Group (d), and the compound according to any one of [1] to [14], Group (a): one or more ingredients selected from the group consisting of insecticidal ingredients, miticidal ingredients, and nematicidal ingredients;
Group (b): fungicidal ingredients;
Group (c): plant growth modulating ingredients; and
Group (d): phytotoxicity-reducing ingredients.

Effect of Invention

The compound of the present invention has an excellent efficacy on controlling harmful arthropods, and is thus useful as an active ingredient for an agent for controlling harmful arthropod.

MODE FOR CARRYING OUT THE INVENTION

The substituent(s) as described herein is/are explained.

The term of "optionally having one or more halogen atoms" or "may optionally have one or more halogen atoms" means that when two or more halogen atoms is present, these halogen atoms may be identical to or different from each other.

The expression of "CX—CY" as used herein represents that the number of carbon atom is from X to Y. For example, the expression of "C1-C6" represents that the number of carbon atom is from 1 to 6.

The term "halogen atom" represents fluorine atom, chlorine atom, bromine atom, or iodine atom.

The term of "chain hydrocarbon group" represents an alkyl group, an alkenyl group, or an alkynyl group.

Example of the term of "alkyl group" include methyl group, ethyl group, propyl group, isopropyl group, 1,1-dimethylpropyl group, 1,2-dimethylpropyl group, 1-ethylpropyl group, butyl group, tert-butyl group, pentyl group, and hexyl group.

Example of the term of "alkenyl group" include vinyl group, 1-propenyl group, 2-propenyl group, 1-methyl-1-propenyl group, 1-methyl-2-propenyl group, 1,2-dimethyl-1-propenyl group, 1,1-dimethyl-2-propenyl group, 3-butenyl group, 4-pentenyl group, and 5-hexenyl group.

Example of the term of "alkynyl group" includes ethynyl group, 1-propynyl group, 2-propynyl group, 1-methyl-2-propynyl group, 1,1-dimethyl-2-propynyl group, 4-pentynyl group, and 5-hexynyl group.

The term of "C1-C6 haloalkyl group" represents a group wherein hydrogen atom(s) is/are replaced with halogen atom(s), and includes, for example, a C1-C6 fluoroalkyl group.

Example of the term of "C1-C6 haloalkyl group" include chloroethyl group, 2,2,2-trifluoroethyl group, 2-bromo-1,1,2,2-tetrafluoroethyl group, 2,2,3,3-tetrafluoropropyl group, 1-methyl-2,2,3,3-tetrafluoropropyl group, and perfluorohexyl group.

Examples of the term of "C1-C6 fluoroalkyl group" include 2,2,2-trifluoroethyl group, 2,2,3,3-tetrafluoropropyl group, 1-methyl-2,2,3,3-tetrafluoropropyl group, and perfluorohexyl group.

Example of the term of "cycloalkyl group" includes cyclopropyl group, cyclobutyl group, cyclopentyl group, cyclohexyl group and cycloheptyl group.

Examples of the term of "three- to seven-membered nonaromatic heterocyclic group" include aziridine ring, azetidine ring, pyrrolidine ring, imidazoline ring, imidazolidine ring, piperidine ring, tetrahydropyrimidine ring, hexahydropyrimidine ring, piperazine ring, azepane ring, oxazolidine ring, isoxazolidine ring, 1,3-oxazinane ring, morpholine ring, 1,4-oxazepane ring, thiazolidine ring, isothiazolidine ring, 1,3-thiazinane ring, thiomorpholine ring, or 1,4-thiazepane ring. Examples of the three to seven membered nonaromatic heterocyclic group optionally having one or more substituents selected from Group E include the followings:

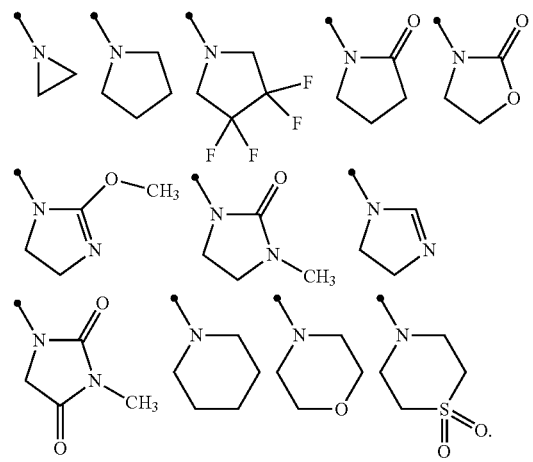

Examples of the term of "phenyl C1-C3 alkyl group {the phenyl moiety in the phenyl C1-C3 alkyl group may optionally have one or more substituents selected from Group D}" include benzyl group, 2-fluorobenzyl group, 4-chlorobenzyl group, 4-(trifluoromethyl)benzyl group, and 2-[4-(trifluoromethyl)phenyl]ethyl group.

The term of "(C3-C6 cycloalkyl)C1-C3 alkyl group optionally having one or more halogen atoms" represents a group wherein the (C3-C6 cycloalkyl) and/or the (C1-C3 alkyl) may optionally has/have one or more halogen atoms, and includes, for example, (2,2-difluorocyclopropyl)methyl group, 2-cyclopropyl-1,1,2,2-tetrafluoroethyl group, and 2-(2,2-difluorocyclopropyl)-1,1,2,2-tetrafluoroethyl group.

The term of "five- or six-membered aromatic heterocyclic group" represents a five membered aromatic heterocyclic group or a six membered aromatic heterocyclic group. Examples of the five membered aromatic heterocyclic group include pyrrolyl group, furyl group, thienyl group, pyrazolyl group, imidazolyl group, triazolyl group, tetrazolyl group, oxazolyl group, isoxazolyl group, thiazolyl group, oxadiazolyl group, and thiadiazolyl group. As the five membered aromatic heterocyclic group, a five membered aromatic heterocyclic group containing 1 to 4 nitrogen atoms, that is, pyrrolyl group, pyrazolyl group, imidazolyl group, 1,2,4-triazolyl group, 1,2,3-triazolyl group, or tetrazolyl group is preferably included. Examples of the six membered aromatic heterocyclic group include pyridyl group, pyridazinyl group, pyrimidinyl group, and pyrazinyl group. As the six membered aromatic heterocyclic group, a six membered aromatic heterocyclic group containing one to two nitrogen atoms, that is, pyridyl group, pyridazinyl group, pyrimidinyl group, and pyrazinyl group is preferably included.

In the compound of the present invention, the structure represented by the following formula:

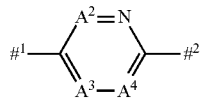

(hereinafter, the formula is referred to as Het². In the formula, #¹ represents a binding position to the Het¹, and #² represents a binding position to the following formula:

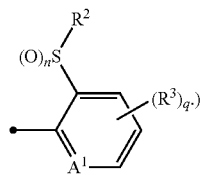

represents the following formulae: Het²-1, Het²-2, Het²-3, or Het²-4:

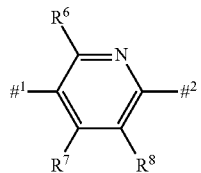

Het²-1

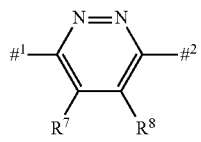

Het²-2

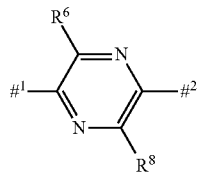

Het²-3

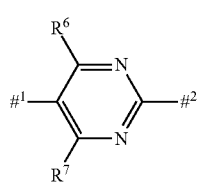

Het²-4

(wherein the symbols are the same as defined above.).

An N-oxide compound represents a compound represented by formula (N-1), a compound represented by formula (N-2), a compound represented by formula (N-3), a compound represented by formula (N-4), a compound represented by formula (N-5), or a compound represented by formula (N-6):

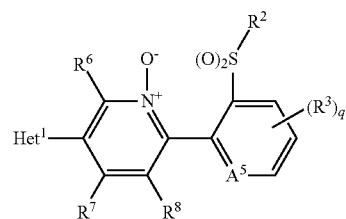

(N-1)

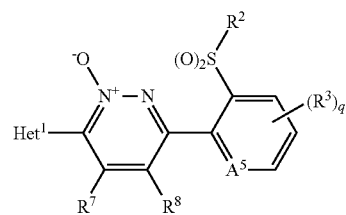

(N-2)

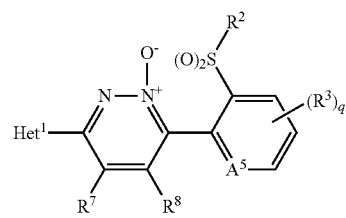

(N-3)

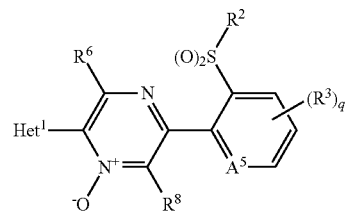

(N-4)

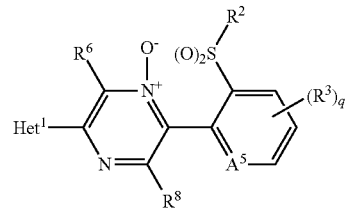

(N-5)

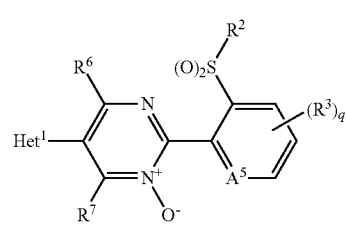

(N-6)

[wherein $A^5$ represents a nitrogen atom, $N^+O^-$, or $CR^9$, and the other symbols are the same as defined above.]).

Examples of the embodiment of the compound of the present invention include the following compounds.

Embodiment 1

A compound of the present invention wherein $R^1$ represents a C1-C4 chain hydrocarbon group having one or more halogen atoms, or a halogen atom;

Embodiment 2

A compound of the present invention wherein $R^1$ represents a C1-C4 alkyl group having three or more fluorine atoms;

Embodiment 3

A compound of the present invention wherein $R^2$ represents a cyclopropyl group, a cyclopropylmethyl group, or a C1-C3 alkyl group optionally having one or more halogen atoms;

Embodiment 4

A compound of the present invention wherein $R^2$ represents a methyl group, an ethyl group, a cyclopropyl group, or a cyclopropylmethyl group;

Embodiment 5

A compound of the present invention wherein $R^2$ represents a methyl group or an ethyl group;

Embodiment 6

A compound of the present invention wherein $R^2$ represents an ethyl group;

Embodiment 7

A compound of the present invention wherein $R^3$ represents a C1-C6 chain hydrocarbon group optionally having one or more substituents selected from Group B, a phenyl group optionally having one or more substituents selected from Group D, or a six membered aromatic heterocyclic group selected from Group V (wherein said six membered aromatic heterocyclic group may optionally have one or more substituents selected from Group D), a five membered aromatic heterocyclic group selected from Group W (wherein said five membered aromatic heterocyclic group may optionally have one or more substituents selected from Group D), $OR^{12}$, $NR^{11}R^{12}$, $NR^{11a}R^{12a}$, $NR^{24}NR^{11}R^{12}$, or a halogen atom;

Group V:

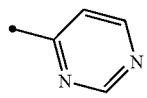
V-1

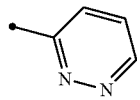
V-2

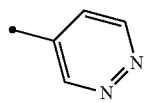
V-3

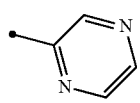
V-4

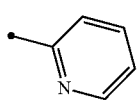
V-5

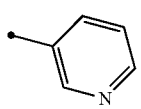
V-6

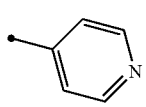
V-7

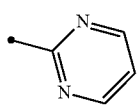
V-8

Group W:

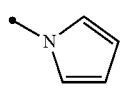
W-1

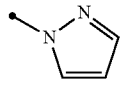
W-2

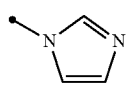
W-3

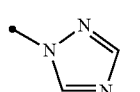
W-4

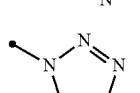
W-5

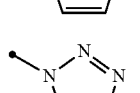
W-6

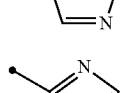
W-7

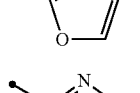
W-8

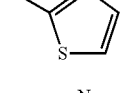
W-9

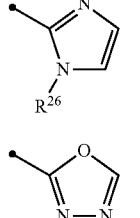
W-10

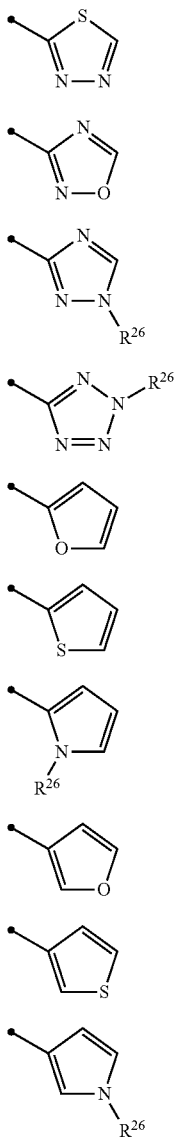

{In the above structure formula, $R^{26}$ represents a C1-C6 alkyl group optionally having one or more halogen atoms.).

Embodiment 8

A compound of the present invention wherein $R^3$ represents a C1-C6 alkyl group optionally having one or more halogen atoms, a phenyl group optionally having one or more substituents selected from Group G, a six membered aromatic heterocyclic group selected from Group V (wherein said six membered aromatic heterocyclic group may optionally have one or more substituents selected from Group G), a five membered aromatic heterocyclic group selected from W-1 to W-6 (wherein said five membered aromatic heterocyclic group may optionally have one or more substituents selected from Group G), $NR^{11}R^{12}$, $NR^{24}NR^{11}R^{12}$, or a halogen atom, $R^{11}$, $R^{12}$, and $R^{24}$ represent independently of each other a hydrogen atom, or a C1-C3 alkyl group optionally having one or more halogen atoms;

Embodiment 9

A compound of the present invention wherein $R^3$ represents a C1-C6 chain hydrocarbon group optionally having one or more halogen atoms, or a halogen atom;

Embodiment 10

A compound of the present invention wherein $R^3$ represents a C1-C6 alkyl group having one or more halogen atoms;

Embodiment 11

A compound of the present invention wherein $R^6$ represents a hydrogen atom, a C1-C6 alkyl group optionally having one or more halogen atoms, or a halogen atom;

Embodiment 12

A compound of the present invention wherein q is 0 or 1;

Embodiment 13

A compound of the present invention wherein q is 0;

Embodiment 14

A compound of the present invention wherein $A^1$ represents a nitrogen atom, or $CR^9$, and $R^9$ represents a hydrogen atom, or a halogen atom;

Embodiment 15

A compound of the present invention wherein $A^1$ represents a nitrogen atom, or CH;

Embodiment 16

A compound of the present invention wherein $A^1$ represents a nitrogen atom;

Embodiment 17

A compound of the present invention wherein $Het^1$ represents $Het^1$-1, $Het^1$-2, $Het^1$-3, $Het^1$-4, or $Het^1$-5:

Embodiment 18

A compound of the present invention wherein $Het^1$ represents $Het^1$-1, or $Het^1$-2;

Embodiment 19

A compound of the present invention wherein $Het^1$ represents $Het^1$-1;

Embodiment 20

A compound of the present invention wherein $Het^1$ represents $Het^1$-2;

Embodiment 21

A compound of the present invention wherein $Het^1$ represents $Het^1$-5;

Embodiment 22

A compound of the present invention wherein Het² represents Het²-1, Het²-2, or Het²-3;

Embodiment 23

A compound of the present invention wherein Het² represents Het²-1;

Embodiment 24

A compound of the present invention wherein Het² represents Het²-2;

Embodiment 25

A compound of the present invention wherein Het² represents Het²-3;

Embodiment 26

A compound of the present invention wherein Het² represents Het²-4;

Embodiment 27

A compound of the present invention wherein $A^1$ represents a nitrogen atom, or CH, $R^1$ represents a C1-C4 chain hydrocarbon group having one or more halogen atoms, or a halogen atom, $R^2$ represents a cyclopropyl group, a cyclopropylmethyl group, or a C1-C3 alkyl group optionally having one or more halogen atoms, $R^3$ represents a C1-C6 chain hydrocarbon group optionally having one or more substituents selected from Group B, a phenyl group optionally having one or more substituents selected from Group D, a six membered aromatic heterocyclic group selected from Group V (wherein said six membered aromatic heterocyclic group may optionally have one or more substituents selected from Group D), a five membered aromatic heterocyclic group selected from Group W (wherein said five membered aromatic heterocyclic group may optionally have one or more substituents selected from Group D), $OR^{12}$, $NR^{11}R^{12}$, $NR^{11a}R^{12a}$, $NR^{24}NR^{11}R^{12}$, or a halogen atom, and $R^6$, $R^7$ and $R^8$ represent independently of each other a hydrogen atom, a C1-C6 alkyl group optionally having one or more halogen atoms, or a halogen atom;

Embodiment 28

A compound of the present invention wherein $A^1$ represents a nitrogen atom, or CH, $R^1$ represents a C1-C4 alkyl group having three or more fluorine atoms, $R^2$ represents a cyclopropyl group, a cyclopropylmethyl group, or a C1-C3 alkyl group optionally having one or more halogen atoms, $R^3$ represents a C1-C6 chain hydrocarbon group optionally having one or more substituents selected from Group B, a phenyl group optionally having one or more substituents selected from Group D, a six membered aromatic heterocyclic group selected from Group V (wherein said six membered aromatic heterocyclic group may optionally have one or more substituents selected from Group D), a five membered aromatic heterocyclic group selected from Group W (wherein said five membered aromatic heterocyclic group may optionally have one or more substituents selected from Group D), $OR^{12}$, $NR^{11}R^{12}$, $NR^{11a}R^{12a}$, $NR^{24}NR^{11}R^{12}$, or a halogen atom, and $R^6$, $R^7$ and $R^8$ represent independently of each other a hydrogen atom, a C1-C6 alkyl group optionally having one or more halogen atoms, or a halogen atom;

Embodiment 29

A compound of the present invention wherein $A^1$ represents a nitrogen atom, or CH; $R^1$ represents a C1-C4 alkyl group having three or more fluorine atoms, $R^2$ represents a methyl group, or an ethyl group, $R^3$ represents a C1-C6 alkyl group optionally having one or more halogen atoms, a phenyl group optionally having one or more substituents selected from Group G, a six membered aromatic heterocyclic group selected from Group V (wherein said six membered aromatic heterocyclic group may optionally have one or more substituents selected from Group G), a five membered aromatic heterocyclic group selected from W-1 to W-6 (wherein said five membered aromatic heterocyclic group may optionally have one or more substituents selected from Group G), $NR^{11}R^{12}$, $NR^{24}NR^{11}R^{12}$, or a halogen atom, $R^{11}$, $R^{12}$ and $R^{24}$ represent independently of each other a hydrogen atom, or a C1-C3 alkyl group optionally having one or more halogen atoms, and $R^6$, $R^7$ and $R^8$ represent independently of each other a hydrogen atom, a C1-C6 alkyl group optionally having one or more halogen atoms, or a halogen atom;

Embodiment 30

A compound of the present invention wherein $A^1$ represents a nitrogen atom, or CH, $R^1$ represents a C1-C4 alkyl group having three or more fluorine atoms, $R^2$ represents an ethyl group, $R^3$ represents a C1-C6 chain hydrocarbon group optionally having one or more halogen atoms, or a halogen atom, and $R^6$, $R^7$ and $R^8$ represent independently of each other a C1-C6 alkyl group optionally having one or more halogen atoms, or a halogen atom;

Embodiment 31

A compound of the present invention wherein $A^1$ represents a nitrogen atom, $R^1$ represents a C1-C4 alkyl group having three or more fluorine atoms, $R^2$ represents an ethyl group, $R^3$ represents a C1-C6 chain hydrocarbon group optionally having one or more halogen atoms, or a halogen atom, and $R^6$, $R^7$ and $R^8$ represent independently of each other a hydrogen atom, a C1-C6 alkyl group optionally having one or more halogen atoms, or a halogen atom;

Embodiment 32

A compound of the present invention wherein $A^1$ represents a nitrogen atom, or CH, $R^1$ represents a C1-C4 alkyl group having three or more fluorine atoms, $R^2$ represents an ethyl group, $R^3$ represents a C1-C6 chain hydrocarbon group optionally having one or more substituents selected from Group B, a phenyl group optionally having one or more substituents selected from Group D, a six membered aromatic heterocyclic group selected from Group V (wherein said six membered aromatic heterocyclic group may optionally have one or more substituents selected from Group D), a five membered aromatic heterocyclic group selected from Group W (wherein said five membered aromatic heterocyclic group may optionally have one or more substituents selected from Group D), $OR^{12}$, $NR^{11}R^{12}$, $NR^{11a}R^{12a}$, $NR^{24}NR^{11}R^{12}$, or a halogen atom, and $R^6$, $R^7$ and $R^8$ represent independently of each other a hydrogen atom, a C1-C6 alkyl group optionally having one or more halogen atoms, or a halogen atom;

Embodiment 33

A compound of the present invention wherein $A^1$ represents a nitrogen atom, or CH, $R^1$ represents a C1-C4 alkyl group having three or more fluorine atoms, $R^2$ represents an ethyl group, $R^3$ represents a C1-C6 alkyl group optionally having one or more halogen atoms, a phenyl group optionally having one or more substituents selected from Group G, a six membered aromatic heterocyclic group selected from Group V (wherein said six membered aromatic heterocyclic group may optionally have one or more substituents selected from Group G), a five membered aromatic heterocyclic group selected from W-1 to W-6 (wherein said five membered aromatic heterocyclic group may optionally have one or more substituents selected from Group G), $NR^{11}R^{12}$, $NR^{24}NR^{11}R^{12}$, or a halogen atom, $R^{11}$, $R^{12}$ and $R^{24}$ represent independently of each other a hydrogen atom, or a C1-C3 alkyl group optionally having one or more halogen atoms, and $R^6$, $R^7$ and $R^8$ represent independently of each other a hydrogen atom, a C1-C6 alkyl group optionally having one or more halogen atoms, or a halogen atom;

Embodiment 34

The compound described in any one of [Embodiment 27] to [Embodiment 33] wherein $Het^1$ represents $Het^1$-1, $Het^1$-2, $Het^1$-3, $Het^1$-4, or $Het^1$-5, and $Het^2$ represents $Het^2$-1, $Het^2$-2, or $Het^2$-3;

Embodiment 35

The compound described in any one of [Embodiment 27] to [Embodiment 33] wherein $Het^1$ represents $Het^1$-1, $Het^1$-2, $Het^1$-3, $Het^1$-4, or $Het^1$-5, and $Het^2$ represents $Het^2$-1;

Embodiment 36

The compound described in any one of [Embodiment 27] to [Embodiment 33] wherein $Het^1$ represents $Het^1$-1, $Het^1$-2, $Het^1$-3, $Het^1$-4, or $Het^1$-5, and $Het^2$ represents $Het^2$-2;

Embodiment 37

The compound described in any one of [Embodiment 27] to [Embodiment 33] wherein $Het^1$ represents $Het^1$-1, $Het^1$-2, $Het^1$-3, $Het^1$-4, or $Het^1$-5, and $Het^2$ represents $Het^2$-3;

Embodiment 38

The compound described in any one of [Embodiment 27] to [Embodiment 33] wherein $Het^1$ represents $Het^1$-1, $Het^1$-2, $Het^1$-3, $Het^1$-4, or $Het^1$-5, and $Het^2$ represents $Het^2$-4;

Embodiment 39

The compound described in any one of [Embodiment 27] to [Embodiment 32] wherein $Het^1$ represents $Het^1$-1, and $Het^2$ represents $Het^2$-1, $Het^2$-2, or $Het^2$-3;

Embodiment 40

The compound described in any one of [Embodiment 27] to [Embodiment 33] wherein $Het^1$ represents $Het^1$-1, and $Het^2$ represents $Het^2$-1;

Embodiment 41

The compound described in any one of [Embodiment 27] to [Embodiment 33] wherein $Het^1$ represents $Het^1$-1, and $Het^2$ represents $Het^2$-2;

Embodiment 42

The compound described in any one of [Embodiment 27] to [Embodiment 33] wherein $Het^1$ represents $Het^1$-1, and $Het^2$ represents $Het^2$-3;

Embodiment 43

The compound described in any one of [Embodiment 27] to [Embodiment 33] wherein $Het^1$ represents $Het^1$-1, and $Het^2$ represents $Het^2$-4;

Embodiment 44

The compound described in any one of [Embodiment 27] to [Embodiment 33] wherein $Het^1$ represents $Het^1$-2, and $Het^2$ represents $Het^2$-1, $Het^2$-2, or $Het^2$-3;

Embodiment 45

The compound described in any one of [Embodiment 27] to [Embodiment 33) wherein $Het^1$ represents $Het^1$-2, and $Het^2$ represents $Het^2$-1;

Embodiment 46

The compound described in any one of [Embodiment 27] to [Embodiment 33] wherein $Het^1$ represents $Het^1$-2, and $Het^2$ represents $Het^2$-2;

Embodiment 47

The compound described in any one of [Embodiment 27] to (Embodiment 33] wherein $Het^1$ represents $Het^1$-2, and $Het^2$ represents $Het^2$-3;

Embodiment 48

The compound described in any one of [Embodiment 27] to [Embodiment 33] wherein $Het^1$ represents $Het^1$-2, and $Het^2$ represents $Het^2$-4;

Embodiment 49

The compound described in any one of [Embodiment 27] to [Embodiment 33] wherein $Het^1$ represents $Het^1$-5, and $Het^2$ represents $Het^2$-1, $Het^2$-2 or $Het^2$-3, and $R^1$ represents a C1-C4 chain hydrocarbon group optionally having one or more halogen atoms, or a halogen atom;

Embodiment 50

The compound described in any one of [Embodiment 27] to [Embodiment 33] wherein $Het^1$ represents $Het^1$-5, $Het^2$ represents Het²-1, and $R^{1a}$ represents a C1-C4 chain hydrocarbon group optionally having one or more halogen atoms, or a halogen atom;

Embodiment 51

The compound described in any one of [Embodiment 27] to [Embodiment 33] wherein $Het^1$ represents $Het^1$-5, $Het^2$ represents Het²-2, and $R^{1a}$ represents a C1-C4 chain hydrocarbon group optionally having one or more halogen atoms, or a halogen atom;

Embodiment 52

The compound described in any one of [Embodiment 27] to [Embodiment 33] wherein $Het^1$ represents $Het^1$-5, $Het^2$ represents Het²-3, and $R^{1a}$ represents a C1-C4 chain hydrocarbon group optionally having one or more halogen atoms, or a halogen atom;

Embodiment 53

The compound described in any one of [Embodiment 27] to [Embodiment 33] wherein $Het^1$ represents $Het^1$-5, $Het^2$ represents Het²-4, and $R^{1a}$ represents a C1-C4 chain hydrocarbon group optionally having one or more halogen atoms, or a halogen atom;

Embodiment 54

A compound of the present invention wherein $A^1$ represents a nitrogen atom, $R^1$ represents a C1-C4 chain hydrocarbon group having one or more halogen atoms, or a halogen atom, $R^2$ represents an ethyl group, $R^3$ represents a C1-C6 alkyl group optionally having one or more halogen atoms, or a halogen atom, $Het^1$ represents $Het^1$-1, $Het^2$ represents Het²-1, Het²-2, or Het²-3, and $R^6$, $R^7$ and $R^8$ represent a hydrogen atom, and q is 0 or 1;

Embodiment 55

The compound described in [Embodiment 54] wherein $Het^2$ represents Het²-1;

Embodiment 56

The compound described in [Embodiment 54] wherein $Het^2$ represents Het²-2;

Embodiment 57

The compound described in [Embodiment 54] wherein $Het^2$ represents Het²-3;

Embodiment 58

The compound described in [Embodiment 55] wherein $X^1$ represents CH, $X^3$ represents $CR^{32}$, $X^4$ represents $CR^{33}$, and $X^5$ represents CH;

Embodiment 59

The compound described in [Embodiment 55] wherein $X^1$ represents a nitrogen atom, $X^3$ represents $CR^{32}$, $X^4$ represents $CR^{33}$, and $X^5$ represents CH;

Embodiment 60

The compound described in [Embodiment 55] wherein $X^1$ represents CH, $X^3$ represents a nitrogen atom, $X^4$ represents $CR^{33}$, and $X^5$ represents CH;

Embodiment 61

The compound described in [Embodiment 55] wherein $X^1$ represents CH, $X^3$ represents $CR^{32}$, $X^4$ represents a nitrogen atom, and $X^5$ represents CH;

Embodiment 62

The compound described in [Embodiment 55] wherein $X^1$ represents CH, $X^3$ represents CR, $X^4$ represents $CR^{33}$, and $X^5$ represents a nitrogen atom;

Embodiment 63

The compound described in [Embodiment 56] wherein $X^1$ represents CH, $X^3$ represents $CR^{32}$, $X^4$ represents $CR^{33}$, and $X^5$ represents CH;

Embodiment 64

The compound described in [Embodiment 56] wherein $X^1$ represents a nitrogen atom, $X^3$ represents $CR^{32}$, $X^4$ represents $CR^{33}$, and $X^5$ represents CH;

Embodiment 65

The compound described in [Embodiment 56] wherein $X^1$ represents CH, $X^3$ represents a nitrogen atom, $X^4$ represents $CR^{33}$, and $X^5$ represents CH;

Embodiment 66

The compound described in [Embodiment 56] wherein $X^1$ represents CH, $X^3$ represents $CR^{32}$, $X^4$ represents a nitrogen atom, and $X^5$ represents CH;

Embodiment 67

The compound described in [Embodiment 56] wherein $X^1$ represents CH, $X^3$ represents CR, $X^4$ represents $CR^{33}$, and $X^5$ represents a nitrogen atom;

Embodiment 68

The compound described in [Embodiment 57] wherein $X^1$ represents CH, $X^3$ represents $CR^{32}$, $X^4$ represents $CR^{33}$, and $X^5$ represents CH;

Embodiment 69

The compound described in [Embodiment 57] wherein $X^1$ represents a nitrogen atom, $X^3$ represents $CR^{32}$, $X^4$ represents $CR^{33}$, and $X^5$ represents CH;

Embodiment 70

The compound described in [Embodiment 57] wherein $X^1$ represents CH, $X^3$ represents a nitrogen atom, $X^4$ represents $CR^{33}$, and $X^5$ represents CH;

Embodiment 71

The compound described in [Embodiment 57] wherein $X^1$ represents CH, $X^3$ represents $CR^{32}$, $X^4$ represents a nitrogen atom, and $X^5$ represents CH;

Embodiment 72

The compound described in [Embodiment 57] wherein $X^1$ represents CH, $X^3$ represents $CR^{32}$, $X^4$ represents $CR^{33}$, and $X^5$ represents a nitrogen atom;

Embodiment 73

A compound represented by formula (I-1):

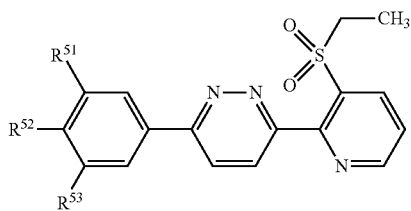

(I-1)

[wherein, any one of $R^{51}$, $R^{52}$ and $R^{53}$ represents a C1-C4 chain hydrocarbon group having one or more halogen atoms, and the remaining groups represent a hydrogen atom or a halogen atom.];

Embodiment 74

A compound represented by formula (I-2):

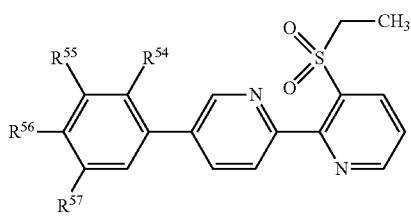

(I-2)

[wherein, any one of $R^{55}$, $R^{56}$ and $R^{57}$ represents $OR^4$, a C1-C4 chain hydrocarbon group having one or more halogen atoms, or a halogen atom, the remaining groups represent a hydrogen atom, or a halogen atom, and $R^{54}$ represents a hydrogen atom, a halogen atom, or a C1-C6 chain hydrocarbon group optionally having one or more halogen atoms.];

Embodiment 75

A compound represented by formula (I-3):

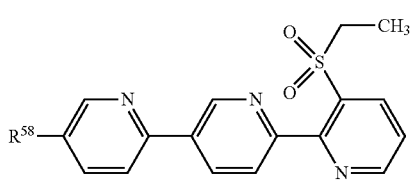

(I-3)

[wherein, $R^{58}$ represents a halogen atom, or a C1-C4 chain hydrocarbon group having one or more halogen atoms.];

Embodiment 76

A compound represented by formula (I-4):

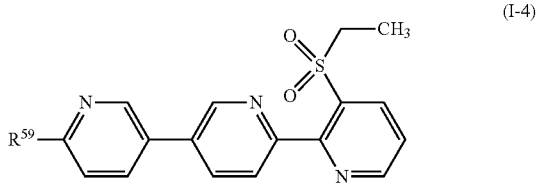

(I-4)

[wherein, $R^{59}$ represents a halogen atom, or a C1-C4 chain hydrocarbon group having one or more halogen atoms.];

Embodiment 77

A compound represented by formula (I-5):

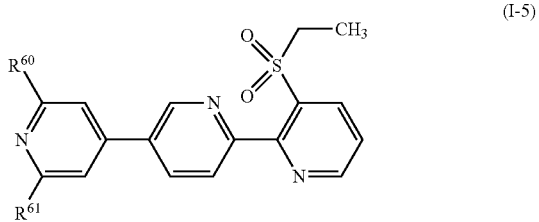

(I-5)

[wherein, any one of $R^{60}$ and $R^{61}$ represents a halogen atom, or a C1-C4 chain hydrocarbon group having one or more halogen atoms, and the other represents a hydrogen atom, a halogen atom, or a C1-C4 chain hydrocarbon group having one or more halogen atoms.];

Embodiment 78

A compound of the present invention wherein $R^6$, $R^7$ and $R^8$ represents a hydrogen atom, a C1-C6 alkyl group optionally having one or more halogen atoms, or a halogen atom;

Embodiment 79

A compound of the present invention wherein $A^1$ represents a nitrogen atom, or CH, $R^1$ represents a C1-C4 alkyl group having three or more fluorine atoms, $R^2$ represents an ethyl group, $R^3$ represents a C1-C6 chain hydrocarbon group optionally having one or more halogen atoms, or a halogen atom, and $R^6$, $R^7$ and $R^8$ represent independently of each other a hydrogen atom, a C1-C6 alkyl group optionally having one or more halogen atoms, or a halogen atom;

Embodiment 80

The compound described in [Embodiment 79] wherein $Het^1$ represents $Het^1$-1, $Het^1$-2, $Het^1$-3, $Het^1$-4, or $Het^1$-5, and $Het^2$ represents $Het^2$-1, $Het^2$-2, or $Het^2$-3;

Embodiment 81

The compound described in [Embodiment 79] wherein Het$^1$ represents Het$^1$-1, Het$^1$-2, Het$^1$-3, Het$^1$-4, or Het$^1$-5, and Het$^2$ represents Het$^2$-1;

Embodiment 82

The compound described in [Embodiment 79] wherein Het$^1$ represents Het$^1$-1, Het$^1$-2, Het$^1$-3, Het$^1$-4, or Het$^1$-5, and Het$^2$ represents Het$^2$-2;

Embodiment 83

The compound described in [Embodiment 79] wherein Het$^1$ represents Het$^1$-1, Het$^1$-2, Het$^1$-3, Het$^1$-4, or Het$^1$-5, and Het$^2$ represents Het$^2$-3;

Embodiment 84

The compound described in [Embodiment 79] wherein Het$^1$ represents Het$^1$-1, Het$^1$-2, Het$^1$-3, Het$^1$-4, or Het$^1$-5, and Het$^2$ represents Het$^2$-4;

Embodiment 85

The compound described in [Embodiment 79] wherein Het$^1$ represents Het$^1$-1, and Het$^2$ represents Het$^2$-1, Het$^2$-2, or Het$^2$-3;

Embodiment 86

The compound described in [Embodiment 79] wherein Het$^1$ represents Het$^1$-1, and Het$^2$ represents Het$^2$-1;

Embodiment 87

The compound described in [Embodiment 79] wherein Het$^1$ represents Het$^1$-1, and Het$^2$ represents Het$^2$-2;

Embodiment 88

The compound described in [Embodiment 79] wherein Het$^1$ represents Het$^1$-1, and Het$^2$ represents Het$^2$-3;

Embodiment 89

The compound described in [Embodiment 79] wherein Het$^1$ represents Het$^1$-1, and Het$^2$ represents Het$^2$-4;

Embodiment 90

The compound described in [Embodiment 79] wherein Het$^1$ represents Het$^1$-2, and Het$^2$ represents Het$^2$-1, Het$^2$-2, or Het$^2$-3;

Embodiment 91

The compound described in [Embodiment 79] wherein Het$^1$ represents Het$^1$-2, and Het$^2$ represents Het$^2$-1;

Embodiment 92

The compound described in [Embodiment 79] wherein Het$^1$ represents Het$^1$-2, and Het$^2$ represents Het$^2$-2;

Embodiment 93

The compound described in [Embodiment 79] wherein Het$^1$ represents Het$^1$-2, and Het$^2$ represents Het$^2$-3;

Embodiment 94

The compound described in [Embodiment 79] wherein Het$^1$ represents Het$^1$-2, and Het$^2$ represents Het$^2$-4;

Embodiment 95

The compound described in [Embodiment 79] wherein Het$^1$ represents Het$^1$-5, Het$^2$ represents Het$^2$-1, Het$^2$-2, or Het$^2$-3, and R$^{1a}$ represents a C1-C4 chain hydrocarbon group optionally having one or more halogen atoms, or a halogen atom;

Embodiment 96

The compound described in [Embodiment 79] wherein Het$^1$ represents Het$^1$-5, Het$^2$ represents Het$^2$-1, and R$^{1a}$ represents a C1-C4 chain hydrocarbon group optionally having one or more halogen atoms, or a halogen atom;

Embodiment 97

The compound described in [Embodiment 79] wherein Het$^1$ represents Het$^1$-5, Het$^2$ represents Het$^2$-2, and R$^{1a}$ represents a C1-C4 chain hydrocarbon group optionally having one or more halogen atoms, or a halogen atom;

Embodiment 98

The compound described in [Embodiment 79] wherein Het$^1$ represents Het$^1$-5, Het$^2$ represents Het$^2$-3, and R$^{1a}$ represents a C1-C4 chain hydrocarbon group optionally having one or more halogen atoms, or a halogen atom;

Embodiment 99

The compound described in [Embodiment 79] wherein Het$^1$ represents Het$^1$-5, Het$^2$ represents Het$^2$-4, and R$^{1a}$ represents a C1-C4 chain hydrocarbon group optionally having one or more halogen atoms, or a halogen atom.

Next, a process for preparing the compound of the present invention is explained.

The compounds of the present invention and the production intermediate compounds can be prepared by the below-mentioned processes.

Process 1

In the compound of the present invention, a compound wherein n is 1 (hereinafter, referred to as Compound (1-n1)) or a compound wherein n is 2 (hereinafter, referred to as Compound (1-n2)) may be prepared by oxidizing a compound wherein n is 0 (hereinafter, referred to as Compound (1-n0)).

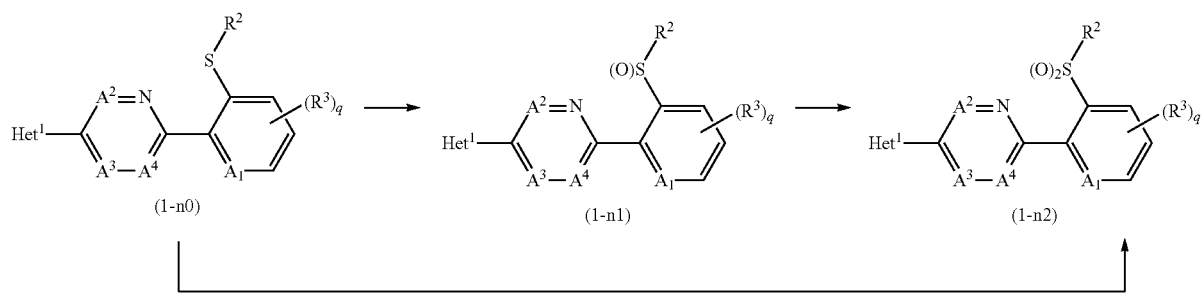

(1-n0)  (1-n1)  (1-n2)

[wherein, the symbols are the same as defined above.]

First, a process for preparing the Compound (1-n1) from the Compound (1-n0) is described.

The reaction is usually carried out in a solvent. Examples of the solvent to be used in the reaction include halogenated aliphatic hydrocarbons such as dichloromethane and chloroform (hereinafter, collectively referred to as halogenated aliphatic hydrocarbons); nitriles such as acetonitrile (hereinafter, collectively referred to nitriles); alcohols such as methanol and ethanol (hereinafter, collectively referred to as alcohols); acetic acid; water; and mixed solvents thereof.

Examples of the oxidizing agent to be used in the reaction include sodium periodate, m-chloroperoxybenzoic acid (hereinafter, referred to as mCPBA) and hydrogen peroxide. When hydrogen peroxide is used as an oxidizing agent, sodium carbonate or a catalyst may be added as needed.

Examples of the catalyst to be used in the reaction include tungstic acid, and sodium tungstate.

In the reaction, the oxidizing agent is used usually within a range of 1 to 1.2 molar ratio(s), the base is used usually within a range of 0.01 to 1 molar ratio(s), and the catalyst is used usually within a range of 0.01 to 0.5 molar ratios, as opposed to 1 mole of the compound (1-n0).

The reaction temperature of the reaction is usually within a range of −20 to 80° C. The reaction period of the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are dried and concentrated to give the compound (1-n1).

Next, a process for preparing the compound (1-n2) from the compound (1-n1) is described.

The reaction is usually carried out in a solvent. Examples of the solvent to be used in the reaction include halogenated aliphatic hydrocarbons, nitriles, alcohols, acetic acid, water, and mixed solvents thereof.

Examples of the oxidizing agent to be used in the reaction include mCPBA and peroxide hydrogen. When peroxide hydrogen is used as an oxidizing agent, a base or a catalyst may be added as needed.

Examples of the base to be used in the reaction include sodium carbonate.

Examples of the catalyst to be used in the reaction include sodium tungstate.

In the reaction, the oxidizing agent is used usually within a range of 1 to 2 molar ratio(s), the base is used usually within a range of 0.01 to 1 molar ratio(s), and the catalyst is used usually within a range of 0.01 to 0.5 molar ratios, as opposed to 1 mole of the compound (1-n1).

The reaction temperature of the reaction is usually within a range of −20 to 120° C. The reaction period of the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are dried and concentrated to give the compound (1-n2).

Also, the compound (1-n2) may be prepared by reacting the compound (1-n0) with an oxidizing agent in one step (one pot).

The reaction may be carried out by using the oxidizing agent in a ratio of usually 2 to 5 molar ratios as opposed to 1 mole of the compound (1-n0) according to the method for preparing the compound (1-n2) from the compound (1-n1).

Process 2

The compound (1-n0) may be prepared by reacting a compound represented by formula (M-1) (hereinafter, referred to as Compound (M-1)) and a compound represented by formula (R-1) (hereinafter, referred to as Compound (R-1)) in the presence of a base.

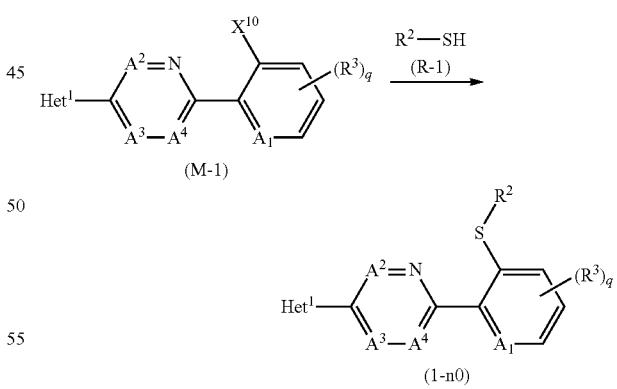

[wherein, $X^{10}$ represents a halogen atom, and the other symbols are the same as defined above.]

The reaction is usually carried out in the presence of a solvent. Examples of the solvents to be used in the reaction include ethers such as tetrahydrofuran (hereinafter, referred to as THF), and ethylene glycol dimethyl ether (hereinafter, referred to as DME), methyl tert-butyl ether, and 1,4-dioxane (hereinafter, collectively referred to as ethers); aromatic hydrocarbons such as toluene and xylene (hereinafter, collectively referred to as aromatic hydrocarbons); nitriles; and aprotic polar solvents such as dimethylformamide (hereinafter, referred to as DMF), N-methylpyrrolidone, and dimethyl sulfoxide (hereinafter, collectively referred to as polar aprotic solvent); and mixed solvents thereof.

Examples of the base to be used in the reaction include alkali metal carbonates such as sodium carbonate and potassium carbonate (hereinafter, collectively referred to as alkali metal carbonates); and alkali metal hydrides such as sodium hydride (hereinafter, collectively referred to as alkali metal hydrides).

In the reaction, the compound (R-1) is used usually within a range of 1 to 10 molar ratio(s), and the base is used usually within a range of 1 to 10 molar ratio(s), as opposed to 1 mole of the compound (M-1).

The reaction temperature of the reaction is usually within a range of −20 to 150° C. The reaction period of the reaction is usually within a range of 0.5 to 24 hours.

When the reaction is completed, water is added to reaction mixtures, and the reaction mixtures are extracted with organic solvent(s), and the organic layers are worked up (for example, drying and concentration) to give the compound (1-n0).

In the reaction, $X^{10}$ is preferably a fluorine atom or a chlorine atom.

Process 3

A compound represented by formula (1a) (hereinafter, referred to Compound (1a)) may be prepared by reacting a compound represented by formula (M-3) (hereinafter, referred to as Compound (M-3)) with a compound represented by formula (R-2) (hereinafter, referred to as Compound (M-3)) in the presence of a metal catalyst.

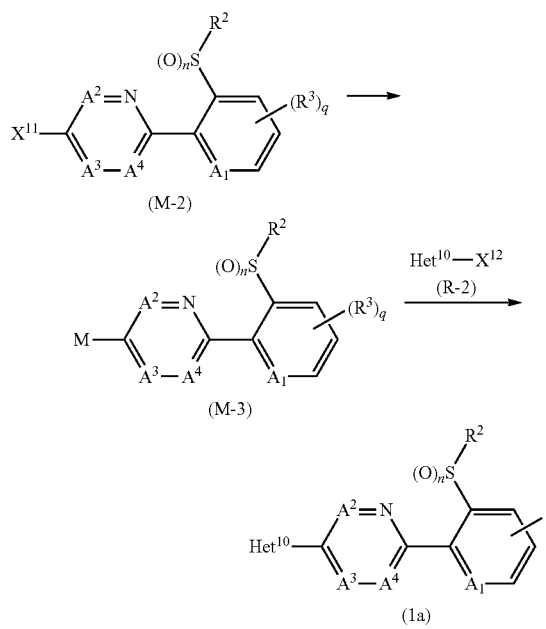

[wherein, $X^{11}$ represents a bromine atom, or an iodine atom; $X^{12}$ represents a chlorine atom, a bromine atom, or an iodine atom; M represents 9-borabiclo[3.3.1]nonan-9-yl, —B(OH)$_2$, a 4,4,5,5,-tetramethyl-1,3,2-dioxaborolan-2-yl, Sn(n-C$_4$H$_9$)$_3$, ZnCl, MgCl, or MgBr; Het$^{10}$ represents Het$^1$-1, Het$^1$-2, Het$^1$-6, Het$^1$-7, Het$^1$-8, or Het$^1$-9; and the other symbols are the same as defined above.]

First, the process for preparing the compound (1a) from the compound (M-3) and the compound (R-2) is described.

The reaction is usually carried out in the presence of a solvent. Examples of the solvent to be used in the reaction include ethers, aromatic hydrocarbons, aprotic polar solvents, water, and mixed solvents thereof.

Examples of the metal catalyst to be used in the reaction include palladium catalysts such as tetrakis(triphenylphosphine)palladium(0), 1,1'-bis(diphenylphosphino)ferrocene palladium(II) dichloride, tris(dibenzylideneacetone)dipalladium(0), and palladium(II) acetate; nickel catalysts such as bis(cyclooctadiene)nickel(0) and nickel(II) chloride; and copper catalyst such as copper(I) iodide and copper(I) chloride.

A ligand, a base, or an inorganic halogenated compound may be added to the reaction as needed.

Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroquinoline, and 1,10-phenanthroline.

Examples of the base to be used in the reaction include alkali metal hydrides; alkali metal carbonates; and organic bases.

Examples of the inorganic halogenated compounds include alkali metal fluorides such as potassium fluoride, and sodium fluoride; and alkali metal chlorides such as lithium chloride, and sodium chloride.

In the reaction, the compound (M-3) is usually used within a range of 1 to 10 molar ratio(s), the metal catalyst is usually used within a range of 0.01 to 0.5 molar ratios, the ligand is usually used within a range of 0.01 to 1 molar ratio(s), the base is usually used within a range of 0.1 to 5 molar ratio(s), and the inorganic halogenated compound is usually used within a range of 0.1 to 5 molar ratios, as opposed to 1 mole of the compound (R-2).

The reaction temperature is usually within a range of −20 to 200° C. The reaction period of the reaction is usually within a range of 0.1 to 24 hours.

When the reaction is completed, water is added to the reaction mixtures, and the reaction mixtures are extracted with organic solvent(s), and the organic layers are worked up (for example, drying and concentration) to give the compound (1a).

The compound (R-2) is a commercially available compound, or can be prepared by using a known method.

The compound (M-3) may be prepared by using a compound represented by formula (M-2) (hereinafter, referred to as Compound (M-2)) according to the method described in WO 06/097691 or the method described in The Journal Of Organic Chemistry, 1995, 60, 7508-7510.

Process 4

A compound represented by formula (1b) (hereinafter, referred to as Compound (1b)) may be prepared by reacting a compound represented by formula (M-4) (hereinafter, referred to as Compound (M-4)) with a compound represented by formula (R-3) (hereinafter, referred to as Compound (R-3)) in the presence of a base. A compound represented by formula (1c) (hereinafter, referred to as Compound (1c)) may be prepared by reacting the compound (M-4) with a compound represented by formula (R-4) (hereinafter, referred to as Compound (R-4)) in the presence of a base. A compound represented by formula (1d) (hereinafter, referred to as Compound (1d)) may be prepared by reacting the compound (M-4) with a compound represented by formula (R-5) (hereinafter, referred to as Compound (R-5)) in the presence of a base.

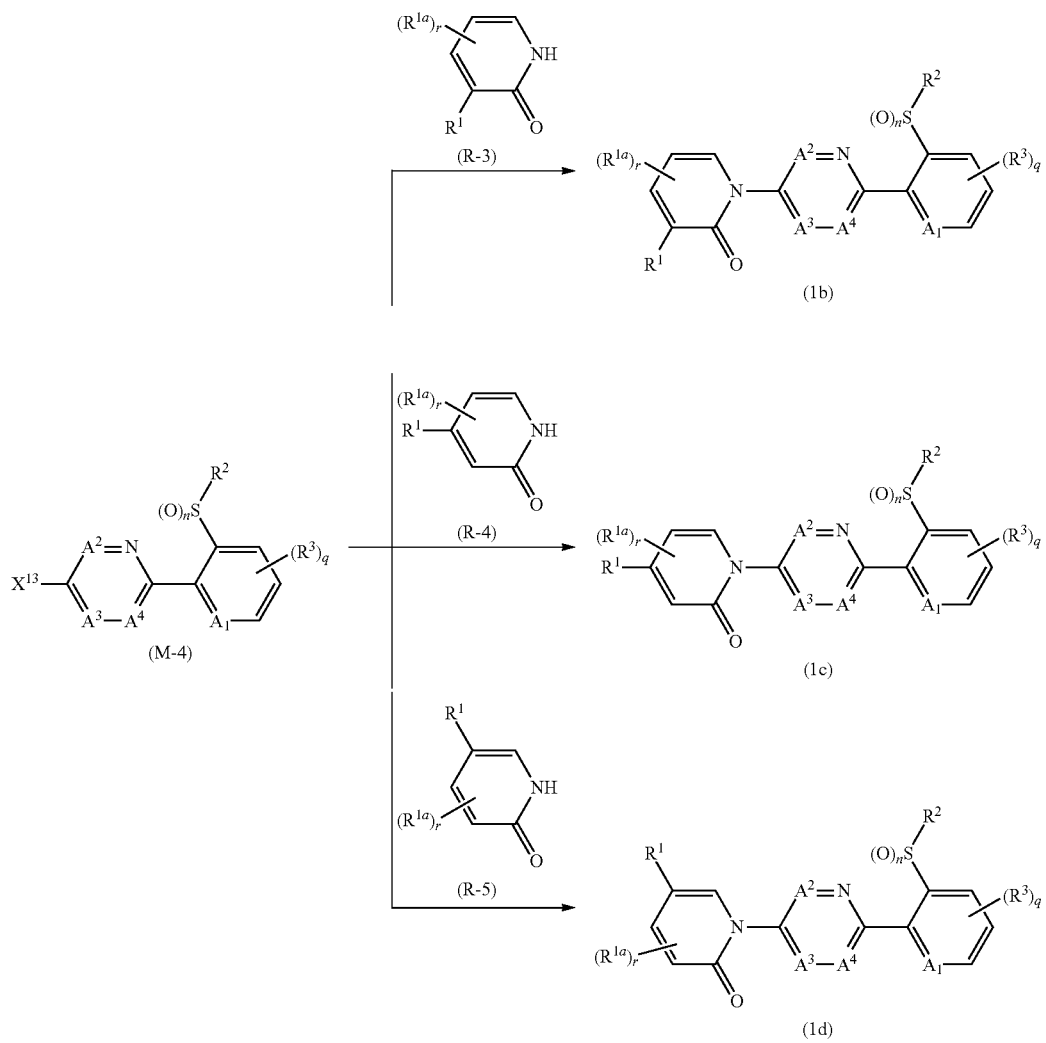

[wherein, $X^{13}$ represents a chlorine atom, or a fluorine atom; and the other symbols are the same as defined above.]

First, a process for preparing the compound (1b) from the compound (M-4) and the compound (R-3) is described.

The compound (R-3) is a commercially available compound, or can be prepared by using a known method.

The reaction is usually carried out in a solvent. Examples of the solvent to be used in the reaction include ethers, aromatic hydrocarbons, nitriles, polar aprotic solvent, and mixed solvents thereof.

Examples of the base to be used in the reaction include alkali metal carbonates, and alkali metal hydrides.

In the reaction, the compound (R-3) is usually used within a range of 1 to 10 molar ratio(s), and the base is usually used with a range of 1 to 10 molar ratios, as opposed to 1 mole of the compound (M-4).

The reaction temperature is usually within a range of −20 to 150° C. The reaction period of the reaction is usually within a range of 0.5 to 24 hours.

When the reaction is completed, water is added to reaction mixtures, and the reaction mixtures are extracted with organic solvent(s), and the organic layers are worked up (for example, drying and concentration) to give the compound (1b).

The compound (1c) may be prepared by using the compound (R-4) in the place of the compound (R-3).

The compound (R-4) is a commercially available compound, or can be prepared by using a known method.

The compound (1d) may be prepared by using the compound (R-5) in the place of the compound (R-3) according to the method of preparing the compound (1b).

The compound (R-5) is a commercially available compound, or can be prepared by using a known method.

Process 5

The compound (1a) may be prepared by reacting a compound represented by formula (M-14) (hereinafter, referred to as Compound (M-14)) with the compound (R-2).

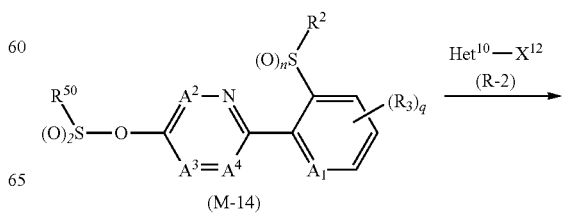

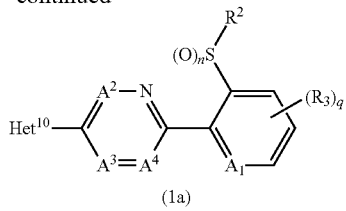

(1a)

[wherein, $R^{50}$ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G; and the other symbols are the same as defined above.]

The reaction may be conducted according to the method described in Process 3 for preparing the compound (1a) from the compound (M-3) and the compound (R-2).

A process for an intermediate compound is described below.

Reference Process 1

The compound (M-2) and the compound (M-4) may be prepared according to the below-mentioned scheme to prepare them as a compound represented by formula (M-6) (hereinafter, referred to as Compound (M-6)) or a compound represented by formula (M-7) (hereinafter, referred to as Compound (M-7)).

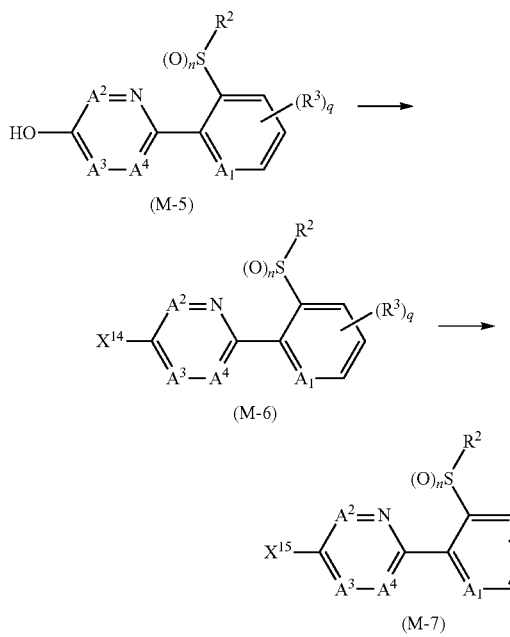

[wherein, $X^{14}$ represents a chlorine atom, or a bromine atom, $X^{15}$ represents a fluorine atom or an iodine atom; and the other symbols are the same as defined above.]

First, a process for preparing the compound (M-6) from the compound (M-5) is described.

The compound (M-6) may be prepared by reacting the compound (M-5) with phosphorus oxychloride or phosphorus oxybromide.

The reaction is usually carried out in a solvent. Examples of the solvent to be used in the reaction include aromatic hydrocarbons.

When phosphorus oxychloride is used, phosphorus oxychloride may be used as a solvent.

In the reaction, phosphorus oxychloride or phosphorus oxybromide is usually used within a range of 1 to 10 molar ratio(s) as opposed to 1 mole of the compound (M-5).

The reaction temperature is usually within a range of 0 to 150° C. The reaction period of the reaction is usually within a range of 0.5 to 24 hours.

When the reaction is completed, water is added to reaction mixtures, and the reaction mixtures are extracted with organic solvents, and the organic layers are worked up (for example, drying and concentration) to give the compound (M-6).

Next, a process for preparing the compound (M-7) from the compound (M-6) is described.

The compound (M-7) may be prepared by reacting the compound (M-6) with inorganic fluoride or inorganic iodide.

The reaction is usually carried out in a solvent. Examples of the solvent to be used in the reaction include nitriles, polar aprotic solvent, nitrogen-containing aromatic solvents, and mixed solvents thereof.

Examples of the inorganic fluoride compound to be used in the reaction include potassium fluoride, sodium fluoride and cesium fluoride. Examples of the inorganic iodide compound to be used in the reaction include potassium iodide and sodium iodide.

In the reaction, inorganic fluoride compound or inorganic iodide compound is usually used within a range of 1 to 10 molar ratio(s) as opposed to 1 mole of the compound (M-6).

The reaction temperature is usually within a range of 0 to 250° C. The reaction period of the reaction is usually within a range of 0.5 to 24 hours.

When the reaction is completed, water is added to reaction mixtures, and the reaction mixtures are extracted with organic solvents, and the organic layers are worked up (for example, drying and concentration) to give the compound (M-7).

Reference Process 2

The compound (M-5) may be prepared by undergoing a dealkylation to a compound represented by formula (M-8) (hereinafter, referred to as Compound (M-8)) in the presence of an acid.

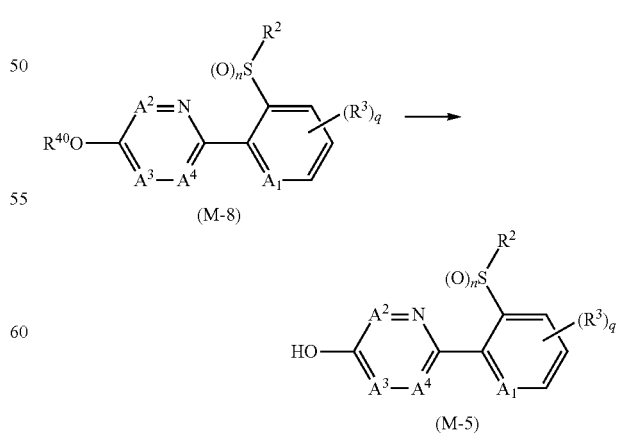

[wherein, $R^{40}$ represents a methyl group or an ethyl group, and the other symbols are the same as defined above.]

The reaction is usually carried out in a solvent. Examples of the solvent to be used in the reaction include halogenated aliphatic hydrocarbons, aromatic hydrocarbons, nitriles, alcohols, acetic acid, water, and mixed solvents thereof.

Examples of the acid to be used in the reaction include inorganic acids such as hydrochloric acid; boron halides such as boron trichloride and boron tribromide; and titanium chloride and aluminum chloride.

In the reaction, the acid is usually used within the range of 0.1 to 10 molar ratio(s) as opposed to 1 mole of the compound (M-8). When the inorganic acids such as hydrochloric acid are used as an acid in the reaction, the inorganic acids may be used as a solvent.

The reaction temperature is usually within a range of −20 to 150° C. The reaction period of the reaction is usually within a range of 0.1 to 24 hours.

When the reaction is completed, water is added to reaction mixtures, and the reaction mixtures are extracted with organic solvents, and the organic layers are worked up (for example, drying and concentration) to give the compound (M-5).

Reference Process 3

The compound (M-8) wherein n is 0 (hereinafter, referred to as Compound (M-8a)), the compound (M-8) wherein n is 1 (hereinafter, referred to as Compound (M-8b)), and the compound (M-8) wherein n is 2 (hereinafter, referred to as Compound (M-8c)) may be prepared according to a below-mentioned method.

Reference Process 4

The compound (M-9) may be prepared by reacting a compound represented by formula (M-12) (hereinafter, referred to as Compound (M-12)) with a compound represented by formula (R-7) (hereinafter, referred to as Compound (R-)) in the presence of a base.

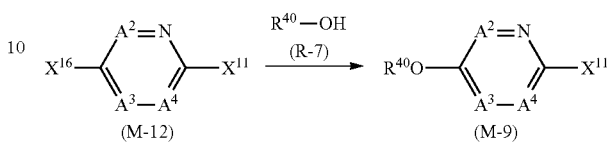

[wherein, $X^{16}$ represents a fluorine atom, a chlorine atom, or a bromine atom; and the other symbols are the same as defined above.]

The reaction is usually carried out in a solvent. Examples of the solvent to be used in the reaction include ethers, aromatic hydrocarbons, nitriles, aprotic polar solvents, and mixed solvents thereof.

Examples of the base to be used in the reaction include alkali metal carbonates, and alkali metal hydrides.

In the reaction, the compound (R-7) is used usually within a range of 1 to 10 molar ratio(s), and the base is used usually within a range of 1 to 10 molar ratio(s), as opposed to 1 mole of the compound (M-12).

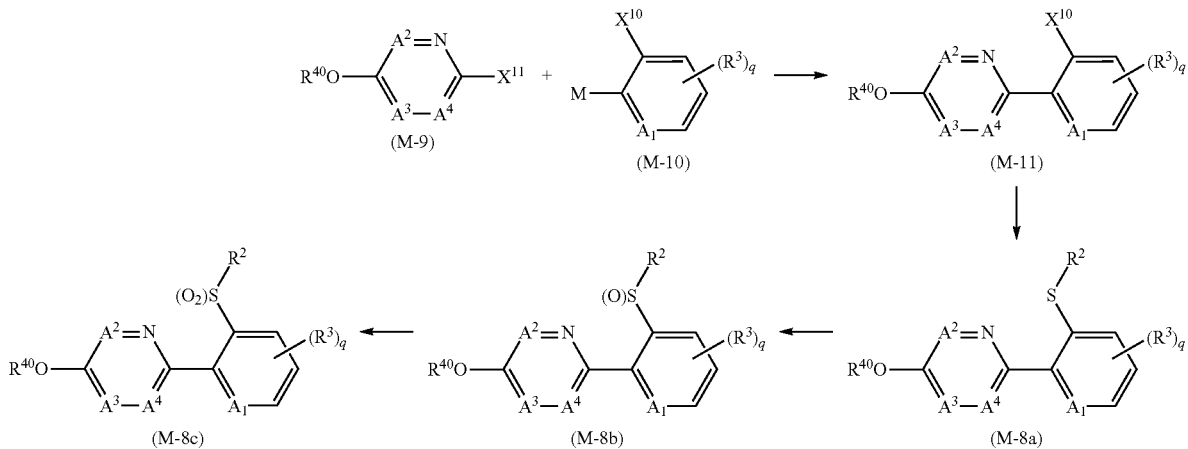

[wherein the symbols are the same as defined above.]

First, a process for preparing a compound represented by formula (M-11) (hereinafter referred to Compound (M-11)) is described.

The compound (M-11) may be prepared by using the compound (M-9) in the place of the compound (R-2) and using the compound (M-10) in the place of the compound (M-3) according to the similar method to that described in Process 3.

The compound (M-10) may be prepared according to the method described in WO 06/097691 or a method described in The Journal Of Organic Chemistry, 1995, 60, 7508-7510.

The compound (M-8a) may be prepared by using the compound (M-11) in the place of the compound (M-1) according to the method described in the process 2.

The compound (M-8b) and the compound (M-8c9 may be prepared by using the compound (M-8a) in the place of the compound (1-n0) according to the method described in the Process 1.

The reaction temperature of the reaction is usually within a range of −20 to 150° C. The reaction period of the reaction is usually within a range of 0.5 to 24 hours.

When the reaction is completed, water is added to the reaction mixtures, and the reaction mixtures are extracted with organic solvent(s), and the organic layers are worked up (for example, drying and concentration) to give the compound (M-9).

Each of the compound (M-12) and the compound (R-7) is a commercially available compound, or can be prepared by using a known method.

Reference Process 5

The compound (M-1) may be prepared by reacting a compound represented by formula (M-13) (hereinafter, referred to Compound (M-13)) with the compound (M-10) in the presence of a metal catalyst.

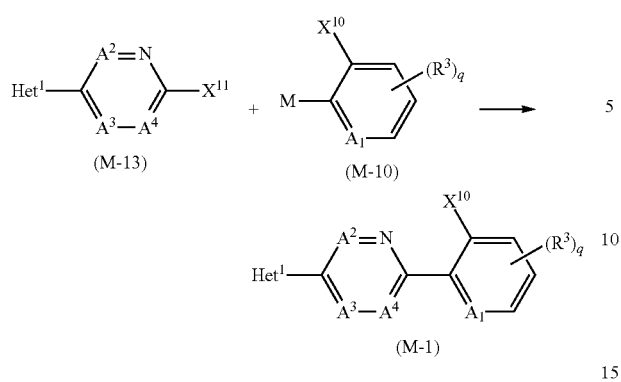

(M-13) + (M-10) → (M-1)

[wherein, the symbols are the same as defined above.]

The compound (M-1) may be prepared by using the compound (M-13) in the place of the compound (M-9) according to the method described in the process 3 for preparing the compound (M-11).

The compound (M-13) may be prepared by using a known method.

Reference Process 6

The compound (M-14) may be prepared by reacting the compound (M-5) with a compound represented by formula (R-6) (hereinafter, referred to as Compound (R-6)) in the presence of a base.

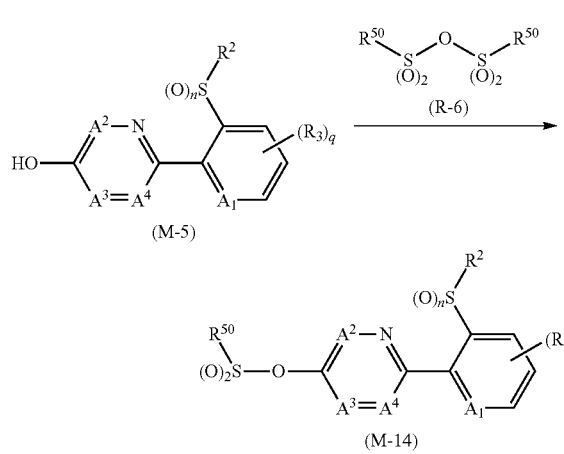

(M-5) + (R-6) → (M-14)

[wherein, the symbols are the same as defined above.]

The compound (R-6) is a commercially available compound, or can be prepared by using a known method.

The reaction is usually carried out in a solvent. Examples of the solvent to be used in the reaction include ethers, aromatic hydrocarbons, nitriles, aprotic polar solvents, and mixed solvents thereof.

Examples of the base to be used in the reaction include organic bases such as diisopropylethylamine and 2,6-lutidine, alkali metal hydrides, and alkali metal carbonates.

In the reaction, the compound (R-6) is usually used within a range of 1 to 2 molar ratio(s), and the base is usually used within a range of 1 to 10 molar ratio(s), as opposed to 1 mole of the compound (M-5).

The reaction temperature of the reaction is usually within a range of −20 to 150° C. The reaction period of the reaction is usually within a range of 0.5 to 24 hours.

When the reaction is completed, water is added to reaction mixtures, and the reaction mixtures are extracted with organic solvent(s), and the organic layers are worked up (for example, drying and concentration) to give the compound (M-14).

Next, specific examples of the compound of the present invention are indicated below.

A compound represented by formula (L-1):

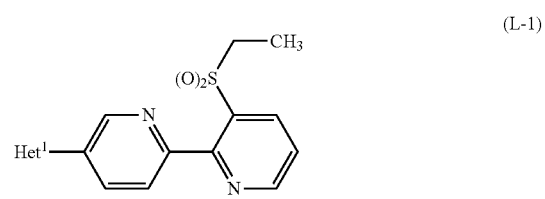

(hereinafter, referred to as Compound (L-1)) wherein $Het^1$ represents H-1:

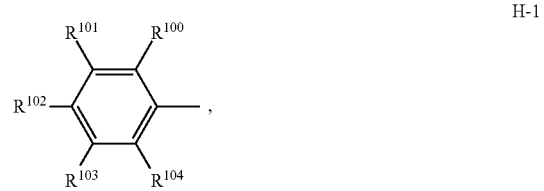

and $R^{100}$, $R^{101}$, $R^{102}$, $R^{103}$, and $R^{104}$ represents any substituents indicated in Table 1 to Table 3 (hereinafter, referred to as Compound Class SX1).

TABLE 1

| $R^{100}$ | $R^{101}$ | $R^{102}$ | $R^{103}$ | $R^{104}$ |
|---|---|---|---|---|
| H | CF$_3$ | H | H | H |
| H | H | CF$_3$ | H | H |
| H | OCF$_3$ | H | H | H |
| H | H | OCF$_3$ | H | H |
| H | SCF$_3$ | H | H | H |
| H | S(O)CF$_3$ | H | H | H |
| H | S(O)$_2$CF$_3$ | H | H | H |
| H | H | SCF$_3$ | H | H |
| H | H | S(O)CF$_3$ | H | H |
| H | H | S(O)$_2$CF$_3$ | H | H |
| H | OS(O)$_2$CF$_3$ | H | H | H |
| H | H | OS(O)$_2$CF$_3$ | H | H |
| H | CF$_3$ | CF$_3$ | H | H |
| H | CF$_3$ | F | H | H |
| H | CF$_3$ | Cl | H | H |
| H | CF$_3$ | CN | H | H |
| H | CF$_3$ | NO$_2$ | H | H |
| H | CF$_3$ | COOCH$_3$ | H | H |
| H | CF$_3$ | N(CH$_3$)$_2$ | H | H |

TABLE 2

| $R^{100}$ | $R^{101}$ | $R^{102}$ | $R^{103}$ | $R^{104}$ |
|---|---|---|---|---|
| H | CF$_3$ | H | CF$_3$ | H |
| H | CF$_3$ | H | F | H |
| H | CF$_3$ | H | Cl | H |
| H | CF$_3$ | H | CN | H |
| H | CF$_3$ | H | NO$_2$ | H |
| H | CF$_3$ | H | COOCH$_3$ | H |
| H | CF$_3$ | H | N(CH$_3$)$_2$ | H |
| H | CF$_3$ | H | H | CF$_3$ |
| H | CF$_3$ | H | H | F |
| H | CF$_3$ | H | H | Cl |

TABLE 2-continued

| $R^{100}$ | $R^{101}$ | $R^{102}$ | $R^{103}$ | $R^{104}$ |
|---|---|---|---|---|
| H | $CF_3$ | H | H | CN |
| H | $CF_3$ | H | H | $NO_2$ |
| H | $CF_3$ | H | H | $COOCH_3$ |
| H | $CF_3$ | H | H | $N(CH_3)_2$ |

TABLE 3

| $R^{100}$ | $R^{101}$ | $R^{102}$ | $R^{103}$ | $R^{104}$ |
|---|---|---|---|---|
| H | F | $CF_3$ | H | H |
| H | Cl | $CF_3$ | H | H |
| H | CN | $CF_3$ | H | H |
| H | $NO_2$ | $CF_3$ | H | H |
| H | $COOCH_3$ | $CF_3$ | H | H |
| H | $N(CH_3)_2$ | $CF_3$ | H | H |
| $CF_3$ | H | $CF_3$ | H | H |
| F | H | $CF_3$ | H | H |
| Cl | H | $CF_3$ | H | H |
| CN | H | $CF_3$ | H | H |
| $NO_2$ | H | $CF_3$ | H | H |
| $COOCH_3$ | H | $CF_3$ | H | H |
| $N(CH_3)_2$ | H | $CF_3$ | H | H |
| H | F | H | F | H |
| H | F | F | F | H |
| H | Cl | H | Cl | H |
| H | Cl | Cl | Cl | H |

The compound (L-1) wherein $Het^1$ represents H-2:

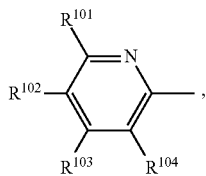

H-2 and $R^{101}$, $R^{102}$, $R^{103}$, and $R^{104}$ represents any substituents indicated in Table 4 to Table 6 (hereinafter, referred to as Compound Class SX2).

TABLE 4

| $R^{101}$ | $R^{102}$ | $R^{103}$ | $R^{104}$ |
|---|---|---|---|
| $CF_3$ | H | H | H |
| H | $CF_3$ | H | H |
| H | H | $CF_3$ | H |
| $OCF_3$ | H | H | H |
| H | $OCF_3$ | H | H |
| H | H | $OCF_3$ | H |
| $SCF_3$ | H | H | H |
| $S(O)CF_3$ | H | H | H |
| $S(O)_2CF_3$ | H | H | H |
| H | $SCF_3$ | H | H |
| H | $S(O)CF_3$ | H | H |
| H | $S(O)_2CF_3$ | H | H |
| H | H | $SCF_3$ | H |
| H | H | $S(O)CF_3$ | H |
| H | H | $S(O)_2CF_3$ | H |
| $OS(O)_2CF_3$ | H | H | H |
| H | $OS(O)_2CF_3$ | H | H |
| H | H | $OS(O)_2CF_3$ | H |

TABLE 5

| $R^{101}$ | $R^{102}$ | $R^{103}$ | $R^{104}$ |
|---|---|---|---|
| $CF_3$ | $CF_3$ | H | H |
| $CF_3$ | F | H | H |
| $CF_3$ | Cl | H | H |
| $CF_3$ | CN | H | H |
| $CF_3$ | H | $CF_3$ | H |
| $CF_3$ | H | F | H |
| $CF_3$ | H | Cl | H |
| $CF_3$ | H | CN | H |
| H | $CF_3$ | $CF_3$ | H |
| H | $CF_3$ | F | H |
| H | $CF_3$ | Cl | H |
| H | $CF_3$ | CN | H |
| H | F | $CF_3$ | H |
| H | Cl | $CF_3$ | H |
| H | CN | $CF_3$ | H |

TABLE 6

| $R^{101}$ | $R^{102}$ | $R^{103}$ | $R^{104}$ |
|---|---|---|---|
| F | $CF_3$ | H | H |
| Cl | $CF_3$ | H | H |
| CN | $CF_3$ | H | H |
| F | H | $CF_3$ | H |
| Cl | H | $CF_3$ | H |
| CN | H | $CF_3$ | H |
| F | H | F | H |
| F | F | F | H |
| Cl | H | Cl | H |
| Cl | Cl | Cl | H |

The compound (L-1) wherein $Het^1$ represents H-3:

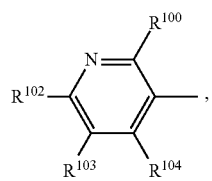

H-3 and $R^{100}$, $R^{102}$, $R^{103}$, and $R^{104}$ represents any substituents indicated in Table 7 to Table 8 (hereinafter, referred to as Compound Class SX3).

TABLE 7

| $R^{100}$ | $R^{102}$ | $R^{103}$ | $R^{104}$ |
|---|---|---|---|
| H | $CF_3$ | H | H |
| H | $OCF_3$ | H | H |
| H | $SCF_3$ | H | H |
| H | $S(O)CF_3$ | H | H |
| H | $S(O)_2CF_3$ | H | H |
| H | $OS(O)_2CF_3$ | H | H |
| H | H | $CF_3$ | H |
| H | H | $OCF_3$ | H |
| H | H | $SCF_3$ | H |
| H | H | $S(O)CF_3$ | H |
| H | H | $S(O)_2CF_3$ | H |
| H | H | $OS(O)_2CF_3$ | H |

TABLE 8

| R¹⁰⁰ | R¹⁰² | R¹⁰³ | R¹⁰⁴ |
|---|---|---|---|
| H | Cl | CF₃ | H |
| H | Cl | OCF₃ | H |
| H | Cl | SCF₃ | H |
| H | Cl | S(O)CF₃ | H |
| H | Cl | S(O)₂CF₃ | H |
| H | Cl | OS(O)₂CF₃ | H |
| H | CF₃ | Cl | H |
| H | OCF₃ | Cl | H |
| H | SCF₃ | Cl | H |
| H | S(O)CF₃ | Cl | H |
| H | S(O)₂CF₃ | Cl | H |
| H | OS(O)₂CF₃ | Cl | H |
| H | F | H | H |
| H | H | F | H |
| H | F | F | H |
| H | Cl | H | H |
| H | H | Cl | H |
| H | Cl | Cl | H |

The compound (L-1) wherein Het¹ represents H-4:

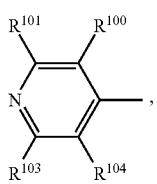

H-4 and R¹⁰⁰, R¹⁰¹, R¹⁰³, and R⁰⁴ represents any substituents indicated in Table 9 (hereinafter, referred to as Compound Class SX4).

TABLE 9

| R¹⁰⁰ | R¹⁰¹ | R¹⁰³ | R¹⁰⁴ |
|---|---|---|---|
| H | CF₃ | H | H |
| H | OCF₃ | H | H |
| H | SCF₃ | H | H |
| H | S(O)CF₃ | H | H |
| H | S(O)₂CF₃ | H | H |
| H | OS(O)₂CF₃ | H | H |
| H | CF₃ | CF₃ | H |
| H | CF₃ | F | H |
| H | CF₃ | Cl | H |
| H | F | H | H |
| H | Cl | H | H |
| H | F | F | H |
| H | Cl | Cl | H |

The compound (L-1) wherein Het¹ represents H-5:

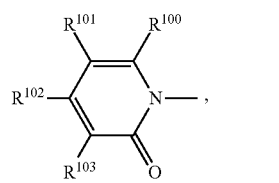

H-5 and R¹⁰⁰, R¹⁰¹, R¹⁰², and R¹⁰³ represents any substituents indicated in Table 10 to Table 11 (hereinafter, referred to as Compound Class SX5).

TABLE 10

| R¹⁰⁰ | R¹⁰¹ | R¹⁰² | R¹⁰³ |
|---|---|---|---|
| H | CF₃ | H | H |
| H | OCF₃ | H | H |
| H | SCF₃ | H | H |
| H | S(O)CF₃ | H | H |
| H | S(O)₂CF₃ | H | H |
| H | OS(O)₂CF₃ | H | H |
| H | H | CF₃ | H |
| H | H | OCF₃ | H |
| H | H | SCF₃ | H |
| H | H | S(O)CF₃ | H |
| H | H | S(O)₂CF₃ | H |
| H | H | OS(O)₂CF₃ | H |
| H | H | H | CF₃ |
| H | H | H | OCF₃ |
| H | H | H | SCF₃ |
| H | H | H | S(O)CF₃ |
| H | H | H | S(O)₂CF₃ |
| H | H | H | OS(O)₂CF₃ |

TABLE 11

| R¹⁰⁰ | R¹⁰¹ | R¹⁰² | R¹⁰³ |
|---|---|---|---|
| H | CF₃ | CF₃ | H |
| H | CF₃ | H | CF₃ |
| H | CF₃ | F | H |
| H | CF₃ | Cl | H |
| H | CF₃ | H | F |
| H | CF₃ | H | Cl |
| H | H | CF₃ | CF₃ |
| H | H | CF₃ | F |
| H | H | CF₃ | Cl |
| H | F | CF₃ | H |
| H | Cl | CF₃ | H |
| H | F | H | CF₃ |
| H | Cl | H | CF₃ |
| H | H | F | CF₃ |
| H | H | Cl | CF₃ |

The compound (L-1) wherein Het¹ represents any one of H-6, H-7, H-8, or H-9:

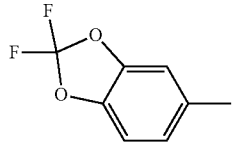

H-6

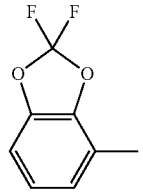

H-7

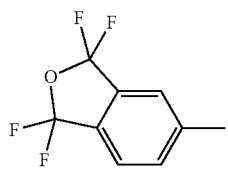

H-8

-continued

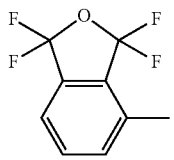

H-9

(hereinafter, referred to as Compound Class SX6).

The compound (L-1) wherein Het$^1$ represents H-10:

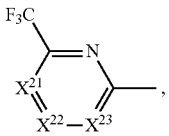

H-10 and $X^{21}$, $X^{22}$ and $X^{23}$ represents any groups indicated in Table 12 (hereinafter, referred to as Compound Class SX7).

TABLE 12

| $X^{21}$ | $X^{22}$ | $X^{23}$ |
|---|---|---|
| N | CH | CH |
| CH | N | CH |
| CH | CH | N |
| N | N | CH |
| CH | N | N |
| N | CH | N |
| N | N | N |

The compound (L-1) wherein Het$^1$ represents H-11:

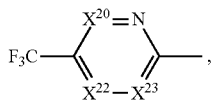

H-11 and $X^{20}$, $X^{22}$ and $X^{23}$ represents any groups indicated in Table 13 (hereinafter, referred to as Compound Class SX8).

TABLE 13

| $X^{20}$ | $X^{22}$ | $X^{23}$ |
|---|---|---|
| N | CH | CH |
| CH | N | CH |
| CH | CH | N |
| N | N | CH |
| CH | N | N |
| N | CH | N |
| N | N | N |

A compound represented by formula (L-2):

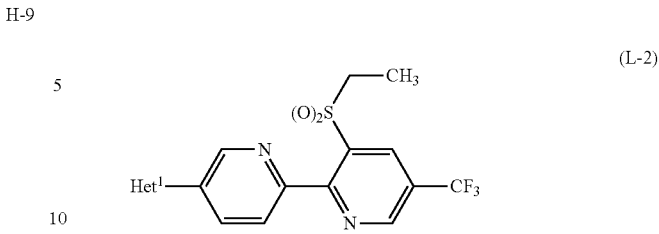

(L-2)

(hereinafter, referred to as Compound (L-2)) wherein Het$^1$ represents H-1, and $R^{100}$, $R^{101}$, $R^{102}$, $R^{103}$, and $R^{104}$ represents any substituents indicated in Table 1 to Table 3 (hereinafter, referred to as Compound Class SX9);

The compound (L-2) wherein Het$^1$ represents H-2, $R^{101}$, $R^{102}$, $R^{103}$ and $R^{104}$ represents any substituents indicated in Table 4 to Table 6 (hereinafter, referred to as Compound Class SX10);

The compound (L-2) wherein Het$^1$ represents H-3, $R^{100}$, $R^{102}$, $R^{103}$ and $R^{104}$ represents any substituents indicated in Table 7 to Table 8 (hereinafter, referred to as Compound Class SX11);

The compound (L-2) wherein Het$^1$ represents H-4, $R^{100}$, $R^{101}$, $R^{103}$ and $R^{104}$ represents any substituents indicated in Table 9 (hereinafter, referred to as Compound Class SX12);

The compound (L-2) wherein Het$^1$ represents H-5, $R^{100}$, $R^{101}$, $R^{102}$ and $R^{103}$ represents any substituents indicated in Table 10 to Table 11 (hereinafter, referred to as Compound Class SX13);

The compound (L-2) wherein Het$^1$ represents any of H-6, H-7, H-8, or H-9 (hereinafter, referred to as Compound Class SX14);

The compound (L-2) wherein Het$^1$ represents H-10, and $X^{21}$, $X^{22}$ and $X^{23}$ represents any groups indicated in Table 12 (hereinafter, referred to as Compound Class SX15).

The compound (L-2) wherein Het$^1$ represents H-11, and $X^{20}$, $X^{22}$ and $X^{23}$ represents any groups indicated in Table 13 (hereinafter, referred to as Compound Class SX16).

A compound represented by formula (L-3):

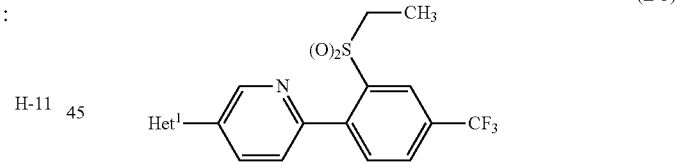

(L-3)

(hereinafter, referred to as Compound (L-3)) wherein Het$^1$ represents H-1, and $R^{100}$, $R^{101}$, $R^{102}$, $R^{103}$, and $R^{104}$ represents any substituents indicated in Table 1 to Table 3 (hereinafter, referred to as Compound Class SX17);

The compound (L-3) wherein Het$^1$ represents H-2, $R^{101}$, $R^{102}$, $R^{103}$ and $R^{104}$ represents any substituents indicated in Table 4 to Table 6 (hereinafter, referred to as Compound Class SX18);

The compound (L-3) wherein Het$^1$ represents H-3, $R^{100}$, $R^{102}$, $R^{103}$ and $R^{104}$ represents any substituents indicated in Table 7 to Table 8 (hereinafter, referred to as Compound Class SX19);

The compound (L-3) wherein Het$^1$ represents H-4, $R^{100}$, $R^{101}$, $R^{103}$ and $R^{104}$ represents any substituents indicated in Table 9 (hereinafter, referred to as Compound Class SX20);

The compound (L-3) wherein Het$^1$ represents H-5, $R^{100}$, $R^{101}$, $R^{102}$ and $R^{103}$ represents any substituents indicated in Table 10 to Table 11 (hereinafter, referred to as Compound Class SX21);

The compound (L-3) wherein Het$^1$ represents any of H-6, H-7, H-8, or H-9 (hereinafter, referred to as Compound Class SX22);

The compound (L-3) wherein Het$^1$ represents H-10, and X$^{21}$, X$^{22}$ and X$^{23}$ represents any groups indicated in Table 12 (hereinafter, referred to as Compound Class SX23).

The compound (L-3) wherein Het$^1$ represents H-11, and X$^{20}$, X$^{22}$ and X$^{23}$ represents any groups indicated in Table 13 (hereinafter, referred to as Compound Class SX24).

A compound represented by formula (L-4):

(L-4)

(hereinafter, referred to as Compound (L-4)) wherein Het$^1$ represents H-1, and R$^{100}$, R$^{101}$, R$^{102}$, R$^{103}$, and R$^{104}$ represents any substituents indicated in Table 1 to Table 3 (hereinafter, referred to as Compound Class SX25);

The compound (L-4) wherein Het$^1$ represents H-2, R$^{101}$, R$^{102}$, R$^{103}$ and R$^{104}$ represents any substituents indicated in Table 4 to Table 6 (hereinafter, referred to as Compound Class SX26);

The compound (L-4) wherein Het$^1$ represents H-3, R$^{100}$, R$^{102}$, R$^{103}$ and R$^{104}$ represents any substituents indicated in Table 7 to Table 8 (hereinafter, referred to as Compound Class SX27);

The compound (L-4) wherein Het$^1$ represents H-4, R$^{100}$, R$^{101}$, R$^{103}$ and R$^{104}$ represents any substituents indicated in Table 9 (hereinafter, referred to as Compound Class SX28);

The compound (L-4) wherein Het$^1$ represents H-5, R$^{100}$, R$^{101}$, R$^{102}$ and R$^{103}$ represents any substituents indicated in Table 10 to Table 11 (hereinafter, referred to as Compound Class SX29);

The compound (L-4) wherein Het$^1$ represents any of H-6, H-7, H-8, or H-9 (hereinafter, referred to as Compound Class SX30);

The compound (L-4) wherein Het$^1$ represents H-10, and X$^{21}$, X$^{22}$ and X$^{23}$ represents any groups indicated in Table 12 (hereinafter, referred to as Compound Class SX31).

The compound (L-4) wherein Het$^1$ represents H-11, and X$^{20}$, X$^{22}$ and X$^{23}$ represents any groups indicated in Table 13 (hereinafter, referred to as Compound Class SX32).

A compound represented by formula (L-5):

(L-5)

(hereinafter, referred to as Compound (L-5)) wherein Het$^1$ represents H-1, and R$^{100}$, R$^{101}$, R$^{102}$, R$^{103}$, and R$^{104}$ represents any substituents indicated in Table 1 to Table 3 (hereinafter, referred to as Compound Class SX33);

The compound (L-5) wherein Het$^1$ represents H-2, R$^{101}$, R$^{102}$, R$^{103}$ and R$^{104}$ represents any substituents indicated in Table 4 to Table 6 (hereinafter, referred to as Compound Class SX34);

The compound (L-5) wherein Het$^1$ represents H-3, R$^{100}$, R$^{102}$, R$^{103}$ and R$^{104}$ represents any substituents indicated in Table 7 to Table 8 (hereinafter, referred to as Compound Class SX35);

The compound (L-5) wherein Het$^1$ represents H-4, R$^{100}$, R$^{101}$, R$^{103}$ and R$^{104}$ represents any substituents indicated in Table 9 (hereinafter, referred to as Compound Class SX36);

The compound (L-5) wherein Het$^1$ represents H-5, R$^{100}$, R$^{101}$, R$^{102}$ and R$^{103}$ represents any substituents indicated in Table 10 to Table 11 (hereinafter, referred to as Compound Class SX37);

The compound (L-5) wherein Het$^1$ represents any of H-6, H-7, H-8, or H-9 (hereinafter, referred to as Compound Class SX38);

The compound (L-5) wherein Het$^1$ represents H-10, and X$^{21}$, X$^{22}$ and X$^{23}$ represents any groups indicated in Table 12 (hereinafter, referred to as Compound Class SX39).

The compound (L-5) wherein Het$^1$ represents H-11, and X$^{20}$, X$^{22}$ and X$^{23}$ represents any groups indicated in Table 13 (hereinafter, referred to as Compound Class SX40).

A compound represented by formula (L-6):

(L-6)

(hereinafter, referred to as Compound (L-6)) wherein Het$^1$ represents H-1, and R$^{100}$, R$^{101}$, R$^{102}$, R$^{103}$, and R$^{104}$ represents any substituents indicated in Table 1 to Table 3 (hereinafter, referred to as Compound Class SX41);

The compound (L-6) wherein Het$^1$ represents H-2, R$^{101}$, R$^{102}$, R$^{103}$ and R$^{104}$ represents any substituents indicated in Table 4 to Table 6 (hereinafter, referred to as Compound Class SX42);

The compound (L-6) wherein Het$^1$ represents H-3, R$^{100}$, R$^{102}$, R$^{103}$ and R$^{104}$ represents any substituents indicated in Table 7 to Table 8 (hereinafter, referred to as Compound Class SX43);

The compound (L-6) wherein Het$^1$ represents H-4, R$^{100}$, R$^{101}$, R$^{103}$ and R$^{104}$ represents any substituents indicated in Table 9 (hereinafter, referred to as Compound Class SX44);

The compound (L-6) wherein Het$^1$ represents H-5, R$^{100}$, R$^{101}$, R$^{102}$ and R$^{103}$ represents any substituents indicated in Table 10 to Table 11 (hereinafter, referred to as Compound Class SX45);

The compound (L-6) wherein Het$^1$ represents any of H-6, H-7, H-8, or H-9 (hereinafter, referred to as Compound Class SX46);

The compound (L-6) wherein Het$^1$ represents H-10, and X$^{21}$, X$^{22}$ and X$^{23}$ represents any groups indicated in Table 12 (hereinafter, referred to as Compound Class SX47).

The compound (L-6) wherein Het$^1$ represents H-11, and X$^{20}$, X$^{22}$ and X$^{23}$ represents any groups indicated in Table 13 (hereinafter, referred to as Compound Class SX48).

A compound represented by formula (L-7):

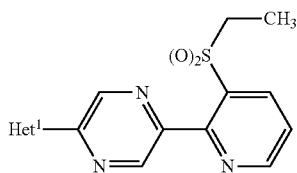

(L-7)

(hereinafter, referred to as Compound (L-7)) wherein $Het^1$ represents H-1, and $R^{100}$, $R^{101}$, $R^{102}$, $R^{103}$, and $R^{104}$ represents any substituents indicated in Table 1 to Table 3 (hereinafter, referred to as Compound Class SX49);

The compound (L-7) wherein $Het^1$ represents H-2, $R^{101}$, $R^{102}$, $R^{103}$ and $R^{104}$ represents any substituents indicated in Table 4 to Table 6 (hereinafter, referred to as Compound Class SX50);

The compound (L-7) wherein $Het^1$ represents H-3, $R^{100}$, $R^{102}$, $R^{103}$ and $R^{104}$ represents any substituents indicated in Table 7 to Table 8 (hereinafter, referred to as Compound Class SX51);

The compound (L-7) wherein $Het^1$ represents H-4, $R^{100}$, $R^{101}$, $R^{103}$ and $R^{104}$ represents any substituents indicated in Table 9 (hereinafter, referred to as Compound Class SX52);

The compound (L-7) wherein $Het^1$ represents H-5, $R^{100}$, $R^{101}$, $R^{102}$ and $R^{103}$ represents any substituents indicated in Table 10 to Table 11 (hereinafter, referred to as Compound Class SX53);

The compound (L-7) wherein $Het^1$ represents any of H-6, H-7, H-8, or H-9 (hereinafter, referred to as Compound Class SX54);

The compound (L-7) wherein $Het^1$ represents H-10, and $X^{21}$, $X^{22}$ and $X^{23}$ represents any groups indicated in Table 12 (hereinafter, referred to as Compound Class SX55).

The compound (L-7) wherein $Het^1$ represents H-11, and $X^{20}$, $X^{22}$ and $X^{23}$ represents any groups indicated in Table 13 (hereinafter, referred to as Compound Class SX56).

A compound represented by formula (L-8):

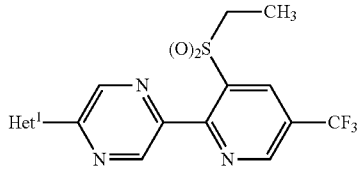

(L-8)

(hereinafter, referred to as Compound (L-8)) wherein $Het^1$ represents H-1, and $R^{100}$, $R^{101}$, $R^{102}$, $R^{103}$, and $R^{104}$ represents any substituents indicated in Table 1 to Table 3 (hereinafter, referred to as Compound Class SX57);

The compound (L-8) wherein $Het^1$ represents H-2, $R^{101}$, $R^{102}$, $R^{103}$ and $R^{104}$ represents any substituents indicated in Table 4 to Table 6 (hereinafter, referred to as Compound Class SX58);

The compound (L-8) wherein $Het^1$ represents H-3, $R^{100}$, $R^{102}$, $R^{103}$ and $R^{104}$ represents any substituents indicated in Table 7 to Table 8 (hereinafter, referred to as Compound Class SX59);

The compound (L-8) wherein $Het^1$ represents H-4, $R^{100}$, $R^{101}$, $R^{103}$ and $R^{104}$ represents any substituents indicated in Table 9 (hereinafter, referred to as Compound Class SX60);

The compound (L-8) wherein $Het^1$ represents H-5, $R^{100}$, $R^{101}$, $R^{102}$ and $R^{103}$ represents any substituents indicated in Table 10 to Table 11 (hereinafter, referred to as Compound Class SX61);

The compound (L-8) wherein $Het^1$ represents any of H-6, H-7, H-8, or H-9 (hereinafter, referred to as Compound Class SX62);

The compound (L-8) wherein $Het^1$ represents H-10, and $X^{21}$, $X^{22}$ and $X^{23}$ represents any groups indicated in Table 12 (hereinafter, referred to as Compound Class SX63).

The compound (L-8) wherein $Het^1$ represents H-11, and $X^{20}$, $X^{22}$ and $X^{23}$ represents any groups indicated in Table 13 (hereinafter, referred to as Compound Class SX64).

A compound represented by formula (L-9):

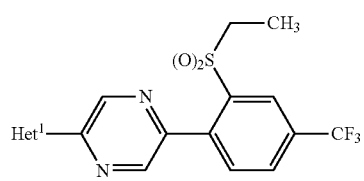

(L-9)

(hereinafter, referred to as Compound (L-9)) wherein $Het^1$ represents H-1, and $R^{100}$, $R^{101}$, $R^{102}$, $R^{103}$, and $R^{104}$ represents any substituents indicated in Table 1 to Table 3 (hereinafter, referred to as Compound Class SX65);

The compound (L-9) wherein $Het^1$ represents H-2, $R^{101}$, $R^{102}$, $R^{103}$ and $R^{104}$ represents any substituents indicated in Table 4 to Table 6 (hereinafter, referred to as Compound Class SX66);

The compound (L-9) wherein $Het^1$ represents H-3, $R^{100}$, $R^{102}$, $R^{103}$ and $R^{104}$ represents any substituents indicated in Table 7 to Table 8 (hereinafter, referred to as Compound Class SX67);

The compound (L-9) wherein $Het^1$ represents H-4, $R^{100}$, $R^{101}$, $R^{103}$ and $R^{104}$ represents any substituents indicated in Table 9 (hereinafter, referred to as Compound Class SX68);

The compound (L-9) wherein $Het^1$ represents H-5, $R^{100}$, $R^{101}$, $R^{102}$ and $R^{104}$ represents any substituents indicated in Table 10 to Table 11 (hereinafter, referred to as Compound Class SX69);

The compound (L-9) wherein $Het^1$ represents any of H-6, H-7, H-8, or H-9 (hereinafter, referred to as Compound Class SX70);

The compound (L-9) wherein $Het^1$ represents H-10, and $X^{21}$, $X^{22}$ and $X^{23}$ represents any groups indicated in Table 12 (hereinafter, referred to as Compound Class SX71).

The compound (L-9) wherein $Het^1$ represents H-11, and $X^{20}$, $X^{22}$ and $X^{23}$ represents any groups indicated in Table 13 (hereinafter, referred to as Compound Class SX72).

A compound represented by formula (L-10):

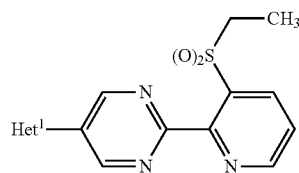

(L-10)

(hereinafter, referred to as Compound (L-10)) wherein $Het^1$ represents H-1, and $R^{100}$, $R^{101}$, $R^{102}$, $R^{103}$, and $R^{104}$ represents any substituents indicated in Table 1 to Table 3 (hereinafter, referred to as Compound Class SX73);

The compound (L-10) wherein Het$^1$ represents H-2, R$^{101}$, R$^{102}$, R$^{103}$ and R$^{104}$ represents any substituents indicated in Table 4 to Table 6 (hereinafter, referred to as Compound Class SX74);

The compound (L-10) wherein Het$^1$ represents H-3, R$^{100}$, R$^{102}$, R$^{103}$ and R$^{104}$ represents any substituents indicated in Table 7 to Table 8 (hereinafter, referred to as Compound Class SX75);

The compound (L-10) wherein Het$^1$ represents H-4, R$^{100}$, R$^{101}$, R$^{103}$ and R$^{104}$ represents any substituents indicated in Table 9 (hereinafter, referred to as Compound Class SX76);

The compound (L-10) wherein Het$^1$ represents H-5, R$^{100}$, R$^{101}$, R$^{102}$ and R$^{103}$ represents any substituents indicated in Table 10 to Table 11 (hereinafter, referred to as Compound Class SX77);

The compound (L-10) wherein Het$^1$ represents any of H-6, H-7, H-8, or H-9 (hereinafter, referred to as Compound Class SX78);

The compound (L-10) wherein Het$^1$ represents H-10, and X$^{21}$, X$^{22}$ and X$^{23}$ represents any groups indicated in Table 12 (hereinafter, referred to as Compound Class SX79).

The compound (L-10) wherein Het$^1$ represents H-11, and X$^{20}$, X$^{22}$ and X$^{23}$ represents any groups indicated in Table 13 (hereinafter, referred to as Compound Class SX80).

A compound represented by formula (L-11):

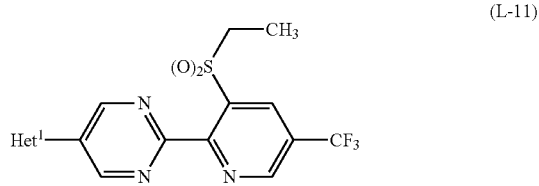

(L-11)

(hereinafter, referred to as Compound (L-11)) wherein Het$^1$ represents H-1, and R$^{100}$, R$^{101}$, R$^{102}$, R$^{103}$, and R$^{104}$ represents any substituents indicated in Table 1 to Table 3 (hereinafter, referred to as Compound Class SX81);

The compound (L-11) wherein Het$^1$ represents H-2, R$^{101}$, R$^{102}$, R$^{103}$ and R$^{104}$ represents any substituents indicated in Table 4 to Table 6 (hereinafter, referred to as Compound Class SX82);

The compound (L-11) wherein Het$^1$ represents H-3, R$^{100}$, R$^{102}$, R$^{103}$ and R$^{104}$ represents any substituents indicated in Table 7 to Table 8 (hereinafter, referred to as Compound Class SX83);

The compound (L-11) wherein Het$^1$ represents H-4, R$^{100}$, R$^{101}$, R$^{103}$ and R$^{104}$ represents any substituents indicated in Table 9 (hereinafter, referred to as Compound Class SX84);

The compound (L-11) wherein Het$^1$ represents H-5, R$^{100}$, R$^{101}$, R$^{102}$ and R$^{103}$ represents any substituents indicated in Table 10 to Table 11 (hereinafter, referred to as Compound Class SX85);

The compound (L-11) wherein Het$^1$ represents any of H-6, H-7, H-8, or H-9 (hereinafter, referred to as Compound Class SX86);

The compound (L-11) wherein Het$^1$ represents H-10, and X$^{21}$, X$^{22}$ and X$^{23}$ represents any groups indicated in Table 12 (hereinafter, referred to as Compound Class SX87);

The compound (L-11) wherein Het$^1$ represents H-11, and X$^{20}$, X$^{22}$ and X$^{23}$ represents any groups indicated in Table 13 (hereinafter, referred to as Compound Class SX88).

A compound represented by formula (L-12):

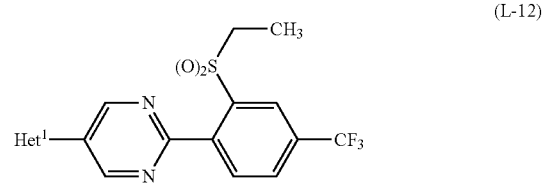

(L-12)

(hereinafter, referred to as Compound (L-12)) wherein Het$^1$ represents H-1, and R$^{100}$, R$^{101}$, R$^{102}$, R$^{103}$, and R$^{104}$ represents any substituents indicated in Table 1 to Table 3 (hereinafter, referred to as Compound Class SX89);

The compound (L-12) wherein Het$^1$ represents H-2, R$^{101}$, R$^{102}$, R$^{103}$ and R$^{104}$ represents any substituents indicated in Table 4 to Table 6 (hereinafter, referred to as Compound Class SX90);

The compound (L-12) wherein Het$^1$ represents H-3, R$^{100}$, R$^{102}$, R$^{103}$ and R$^{104}$ represents any substituents indicated in Table 7 to Table 8 (hereinafter, referred to as Compound Class SX91);

The compound (L-12) wherein Het$^1$ represents H-4, R$^{100}$, R$^{101}$, R$^{103}$ and R$^{104}$ represents any substituents indicated in Table 9 (hereinafter, referred to as Compound Class SX92);

The compound (L-12) wherein Het$^1$ represents H-5, R$^{100}$, R$^{101}$, R$^{102}$ and R$^{103}$ represents any substituents indicated in Table 10 to Table 11 (hereinafter, referred to as Compound Class SX93);

The compound (L-12) wherein Het$^1$ represents any of H-6, H-7, H-8, or H-9 (hereinafter, referred to as Compound Class SX94);

The compound (L-12) wherein Het$^1$ represents H-10, and X$^{21}$, X$^{22}$ and X$^{23}$ represents any groups indicated in Table 12 (hereinafter, referred to as Compound Class SX95).

The compound (L-12) wherein Het$^1$ represents H-11, and X$^{20}$, X$^{22}$ and X$^{23}$ represents any groups indicated in Table 13 (hereinafter, referred to as Compound Class SX96).

Next, specific examples of production intermediate compound are described below.

A compound represented by formula (L-13):

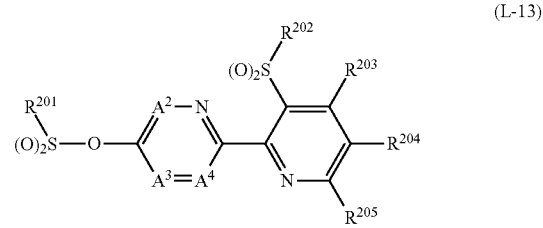

(L-13)

(hereinafter, referred to as Compound (L-13)) wherein A$^2$, A$^3$, and A$^4$ represent CH, and R$^{201}$, R$^{202}$, R$^{203}$, R$^{204}$, and R$^{205}$ represent any substituents indicated in Table 14 to Table 17);

The compound represented by formula (L-13) wherein A$^2$ and A$^4$ represent CH, A$^3$ represents C(CH$_3$), and R$^{201}$, R$^{202}$, R$^{203}$, R$^{204}$, and R$^{205}$ represent any substituents indicated in Table 14 to Table 17;

The compound represented by formula (L-13) wherein A$^2$ and A$^4$ represent CH, A$^3$ represents C(OCH$_3$), and R$^{201}$, R$^{202}$, R$^{203}$, R$^{204}$, and R$^{205}$ represent any substituents indicated in Table 14 to Table 17;

The compound represented by formula (L-13) wherein $A^2$ and $A^4$ represent CH, $A^3$ represents $C(NO_2)$, and $R^{201}$, $R^{202}$, $R^{203}$, $R^{204}$, and $R^{205}$ represent any substituents indicated in Table 14 to Table 17;

The compound represented by formula (L-13) wherein $A^2$ represents a nitrogen atom, $A^3$ and $A^4$ represent CH, and $R^{201}$, $R^{202}$, $R^{203}$, $R^{204}$, and $R^{205}$ represent any substituents indicated in Table 14 to Table 17;

The compound represented by formula (L-13) wherein $A^2$ and $A^4$ represent CH, $A^3$ represents a nitrogen atom, and $R^{201}$, $R^{202}$, $R^{203}$, $R^{204}$, and $R^{205}$ represent any substituents indicated in Table 14 to Table 17;

The compound represented by formula (L-13) wherein $A^2$ and $A^4$ represent CH, $A^4$ represents a nitrogen atom, and $R^{201}$, $R^{202}$, $R^{203}$, $R^{204}$, and $R^{205}$ represent any substituents indicated in Table 14 to Table 17.

TABLE 14

| $R^{201}$ | $R^{202}$ | $R^{203}$ | $R^{204}$ | $R^{205}$ |
|---|---|---|---|---|
| $CF_3$ | $CH_3$ | H | H | H |
| $CF_3$ | $CH_2CH_3$ | H | H | H |
| $CF_2CF_3$ | $CH_3$ | H | H | H |
| $CF_2CF_3$ | $CH_2CH_3$ | H | H | H |
| $CF_2CF_2CF_3$ | $CH_3$ | H | H | H |
| $CF_2CF_2CF_3$ | $CH_2CH_3$ | H | H | H |
| $CF_2CF_2CF_3$ | $CH_3$ | H | H | H |
| $CF_2CF_2CF_3$ | $CH_2CH_3$ | H | H | H |

TABLE 15

| $R^{201}$ | $R^{202}$ | $R^{203}$ | $R^{204}$ | $R^{205}$ |
|---|---|---|---|---|
| $CF_3$ | $CH_2CH_3$ | H | H | $NH_2$ |
| $CF_3$ | $CH_2CH_3$ | H | H | $NHCH_3$ |
| $CF_2CF_3$ | $CH_2CH_3$ | H | H | $N(CH_3)_2$ |
| $CF_2CF_3$ | $CH_2CH_3$ | H | H | 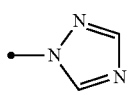 |
| $CF_2CF_2CF_3$ | $CH_2CH_3$ | H | H | 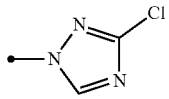 |
| $CF_2CF_2CF_3$ | $CH_2CH_3$ | H | H | 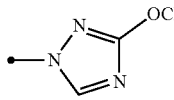 |
| $CF_2CF_2CF_3$ | $CH_2CH_3$ | H | H | 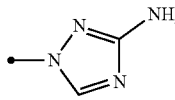 |

TABLE 16

| $R^{201}$ | $R^{202}$ | $R^{203}$ | $R^{204}$ | $R^{205}$ |
|---|---|---|---|---|
| $CF_3$ | $CH_2CH_3$ | H | 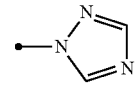 | H |
| $CF_3$ | $CH_2CH_3$ | H |  | H |
| $CF_2CF_3$ | $CH_2CH_3$ | H |  | H |
| $CF_2CF_3$ | $CH_2CH_3$ | H |  | H |
| $CF_2CF_2CF_3$ | $CH_2CH_3$ | H |  | H |
| $CF_2CF_2CF_3$ | $CH_2CH_3$ | H | 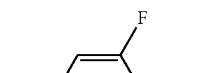 | H |
| $CF_2CF_2CF_3$ | $CH_2CH_3$ | H | 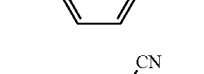 | H |
| $CF_2CF_2CF_3$ | $CH_2CH_3$ | H | 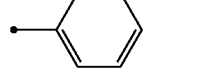 | H |
| $CF_2CF_2CF_3$ | $CH_2CH_3$ | H | 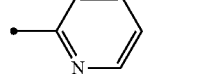 | H |
| $CF_2CF_2CF_3$ | $CH_2CH_3$ | H | 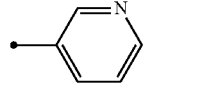 | H |
| $CF_2CF_2CF_3$ | $CH_2CH_3$ | H | 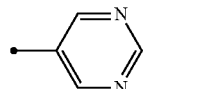 | H |
| $CF_2CF_2CF_3$ | $CH_2CH_3$ | H | 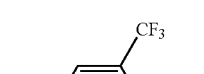 | H |

TABLE 17

| $R^{201}$ | $R^{202}$ | $R^{203}$ | $R^{204}$ | $R^{205}$ |
|---|---|---|---|---|
| $CF_2CF_2CF_3$ | $CH_2CH_3$ | H | $OCH_3$ | H |
| $CF_2CF_2CF_3$ | $CH_2CH_3$ | H | $OCH_2CH_3$ | H |
| $CF_2CF_2CF_3$ | $CH_2CH_3$ | H | $OCH_2CH_2CH_3$ | H |
| $CF_2CF_2CF_3$ | $CH_2CH_3$ | H | $OCH_2CH_2CH_2CH_3$ | H |
| $CF_2CF_2CF_3$ | $CH_2CH_3$ | H | $OCH(CH_3)_2$ | H |
| $CF_2CF_2CF_3$ | $CH_2CH_3$ | H | $OCH_2CF_3$ | H |
| $CF_2CF_2CF_3$ | $CH_2CH_3$ | H | $OCH_2CF_2H$ | H |
| $CF_2CF_2CF_3$ | $CH_2CH_3$ | H | $OCH_2CF_2CF_3$ | H |
| $CF_2CF_2CF_3$ | $CH_2CH_3$ | H | $OCF_3$ | H |
| $CF_2CF_2CF_3$ | $CH_2CH_3$ | H | $OCF_2CF_2H$ | H |
| $CF_2CF_2CF_3$ | $CH_2CH_3$ | H | $CF_3$ | H |
| $CF_2CF_2CF_3$ | $CH_2CH_3$ | H | $CF_2CF_3$ | H |
| $CF_2CF_2CF_3$ | $CH_2CH_3$ | H | $CF_2CF_2H$ | H |

TABLE 17-continued

| R$^{201}$ | R$^{202}$ | R$^{203}$ | R$^{204}$ | R$^{205}$ |
|---|---|---|---|---|
| CF$_2$CF$_2$CF$_3$ | CH$_2$CH$_3$ | H | cyclopropyl | H |
| CF$_2$CF$_2$CF$_3$ | CH$_2$CH$_3$ | H | cyclobutyl | H |
| CF$_2$CF$_2$CF$_3$ | CH$_2$CH$_3$ | H | cyclopentyl | H |
| CF$_2$CF$_2$CF$_3$ | CH$_2$CH$_3$ | H | cyclohexyl | H |
| CF$_2$CF$_2$CF$_3$ | CH$_2$CH$_3$ | H | 2-cyanocyclopropyl (NC-) | H |
| CF$_2$CF$_2$CF$_3$ | CH$_2$CH$_3$ | H | 2-(trifluoromethyl)cyclopropyl (F$_3$C-) | H |

The Present compound may be mixed or combined with one or more ingredient(s) selected from a group consisting of Group (a), Group (b), Group (c), and Group (d) (hereinafter, referred to as Present ingredient).

The above-mentioned mixing or combining represents a use of the Present compound and the Present ingredient at same time, separately or at certain intervals.

When the Present compound and the present ingredient are used at the same time, the Present compound and the Present ingredient may be contained in separate formulations respectively or may be contained in the same one formulation.

One aspect of the present invention is a composition comprising one or more ingredients selected from Group (a), Group (b), Group (c) and Group (d) (that is, Present ingredient) as well as the Present compound.

Group (a) represents an insecticidal ingredient group, a miticidal ingredient group, or a nematicidal ingredient group, which is selected from the group consisting of the following sub group a-1 to sub group a-10.
Sub group a-1: Carbamate acetylcholinesterase (AChE) inhibitors
Sub group a-2: Organophosphorus acetylcholinesterase (AChE) inhibitors
Sub group a-3: GABA-gated chloride channel blockers
Sub group a-4: GABA-gated chloride channel allosteric modulators
Sub group a-5: Sodium channel modulators
Sub group a-6: Nicotinic acetylcholine receptor (nAChR) competitive modulators
Sub group a-7: Ryanodine receptor modulators
Sub group a-8: Microbial materials
Sub group a-9: Nematicidal ingredients
Sub group a-10: The other group as insecticidal active ingredients and miticidal active ingredients Group (b) represents a fungicidal active ingredient group selected from the group consisting of the following sub group b-1 to sub group b-18.
Sub group b-1: PA fungicides (Phenyl amide)
Sub group b-2: MBC fungicides (methyl benzimidazole carbamate)
Sub group b-3: Thiazole carboxamides
Sub group b-4: SDHI (Succinate dehydrogenase inhibitors)
Sub group b-5: QoI fungicides (Qo Inhibitors)
Sub group b-6: QiI fungicides (Qi Inhibitors)
Sub group b-7: Thiophene carboxamides
Sub group b-8: AP fungicides (Anilinopyrimidine)
Sub group b-9: PP fungicides (Phenylpyrrole)
Sub group b-10: AH fungicides (Aromatic hydrocarbons)
Sub group b-11: DMI fungicides (Demethylation inhibitors)
Sub group b-12: CCA fungicides (Carboxylic acid amide)
Sub group b-13: Piperidinyl thiazole isoxazoline
Sub group b-14: Tetrazolyl oxime
Sub group b-15: Dithiocarbamate
Sub group b-16: Phthalimide
Sub group b-17: Microbial fungicides
Sub group b-18: Other fungicides Group (c) represents a plant growth modulating ingredients group selected from the group consisting of the following sub group c-1, sub group c-2, and sub group c-3.
Sub group c-1: Plant growth modulating compounds
Sub group c-2: Mycorrhizal fungi group
Sub group c-3: Root nodule bacteria group Group (d) represents a phytotoxicity-reducing ingredient group.

The composition comprising the above-mentioned present ingredients and the present compounds can exert their efficacies of the composition depending on the content or the content ratio of the above-mentioned present ingredients and the present compounds contained in the composition. Accordingly, the usage of the above-mentioned composition may be decided depending on the effect that is expressed by the above-mentioned composition. The above-mentioned composition may have one or two usages therefor.

One aspect of above-mentioned composition is an agrochemical composition.

Another aspect of the above-mentioned composition is a composition for controlling harmful arthropods.

Another aspect of the above-mentioned composition is an insecticidal, miticidal or nematicidal composition.

Another aspect of the above-mentioned composition is a fungicidal composition.

Another aspect of the above-mentioned composition is a plant growth modulating composition.

Another aspect of the above-mentioned composition is a phytotoxicity-reducing composition.

Examples of the combination of the Present ingredient and the Present compound are described below. For example, "akanicarb+SX" represents a combination of alanycarb and SX. The symbol of "SX" represents any one of the Present compound selected from the Compound Class SX1 to the Compound Class SX96. Also, all of the below-mentioned present ingredient are known ingredients, and are commercially available or may be produced by the known method. If the present ingredient is a bacteria, it is available from the bacterial authority depository. The numerical number in bracket represents a CAS register number.

Examples of the combination of the Present ingredient of the above sub group a-1 and the Present compound:
alanycarb+SX, aldicarb+SX, bendiocarb+SX, benfuracarb+SX, butocarboxim+SX, butoxycarboxim+SX, carbaryl: NAC+SX, carbofuran+SX, carbosulfan+SX, ethiofencarb+SX, fenobucarb: BPMC+SX, formetanate+SX, furathiocarb+SX, isoprocarb: MIPC+SX, methiocarb+SX, methomyl+SX, metolcarb+SX, oxamyl+SX, pirimicarb+SX, propoxur: PHC+SX, thiodicarb+SX, thiofanox+SX, triazamate+SX, trimethacarb+SX, XMC+SX, xylylcarb+SX.

Examples of the combination of the Present ingredient of the above sub group a-2 and the Present compound:

acephate+SX, azamethiphos+SX, azinphos-ethyl+SX, azinphos-methyl+SX, cadusafos+SX, chlorethoxyfos+SX, chlorfenvinphos+SX, chlormephos+SX, chlorpyrifos+SX, chlorpyrifos-methyl+SX, coumaphos+SX, cyanophos: CYAP+SX, demeton-S-methyl+SX, diazinon+SX, dichlorvos: DDVP+SX, dicrotophos+SX, dimethoate+SX, dimethylvinphos+SX, disulfoton+SX, EPN+SX, ethion+SX, ethoprophos+SX, famphur+SX, fenamiphos+SX, fenitrothion: MEP+SX, fenthion: MPP+SX, fosthiazate+SX, heptenophos+SX, imicyafos+SX, isofenphos+SX, isopropyl-O-(methoxyaminothiophosphoryl)salicylate+SX, isoxathion+SX, malathion+SX, mecarbam+SX, methamidophos+SX, methidathion: DMTP+SX, mevinphos+SX, monocrotophos+SX, naled: BRP+SX, omethoate+SX, oxydemeton-methyl+SX, parathion+SX, parathion-methyl+SX, phenthoate: PAP+SX, phorate+SX, phosalone+SX, phosmet: PMP+SX, phosphamidon+SX, phoxim+SX, pirimiphos-methyl+SX, profenofos+SX, propetamphos+SX, prothiofos+SX, pyraclofos+SX, pyridaphenthion+SX, quinalphos+SX, sulfotep+SX, tebupirimfos+SX, temephos+SX, terbufos+SX, tetrachlorvinphos+SX, thiometon+SX, triazophos+SX, trichlorfon: DEP+SX, vamidothion+SX.

Examples of the combination of the Present ingredient of the above sub group a-3 and the Present compound:

ethiprole+SX, fipronil+SX, flufiprole+SX, chlordane+SX, endosulfan+SX, alpha-endosulfan+SX.

Examples of the combination of the Present ingredient of the above sub group a-4 and the Present compound:

afoxolaner+SX, fluralaner+SX, broflanilide+SX, fluxametamide+SX.

Examples of the combination of the Present active ingredient of the above sub group a-5 and the Present compound:

acrinathrin+SX, allethrin+SX, bifenthrin+SX, kappa-bifenthrin+SX, bioallethrin+SX, bioresmethrin+SX, cycloprothrin+SX, cyfluthrin+SX, beta-cyfluthrin+SX, cyhalothrin+SX, gamma-cyhalothrin+SX, lambda-cyhalothrin+SX, cypermethrin+SX, alpha-cypermethrin+SX, beta-cypermethrin+SX, theta-cypermethrin+SX, zeta-cypermethrin+SX, cyphenothrin+SX, deltamethrin+SX, empenthrin+SX, esfenvalerate+SX, etofenprox+SX, fenpropathrin+SX, fenvalerate+SX, flucythrinate+SX, flumethrin+SX, fluvalinate+SX, tau-fluvalinate+SX, halfenprox+SX, heptafluthrin+SX, imiprothrin+SX, kadethrin+SX, meperfluthrin+SX, momfluorothrin+SX, permethrin+SX, phenothrin+SX, prallethrin+SX, pyrethrins+SX, resmethrin+SX, silafluofen+SX, tefluthrin+SX, kappa-tefluthrin+SX, tetramethrin+SX, tetramethylfluthrin+SX, tralomethrin+SX, transfluthrin+SX, benfluthrin+SX, flufenoprox+SX, flumethrin+SX, sigma-cypermethrin+SX, furamethrin+SX, metofluthrin+SX, profluthrin+SX, dimefluthrin+SX, epsilon-metofluthrin+SX, epsilon-momfluorothrin+SX, methoxychlor+SX.

Examples of the combination of the Present ingredient of the above sub group a-6 and the Present compound:

acetamiprid+SX, clothianidin+SX, dinotefuran+SX, imidacloprid+SX, nitenpyram+SX, thiacloprid+SX, thiamethoxam+SX, sulfoxaflor+SX, flupyradifurone+SX, triflumezopyrim+SX, dicloromezotiaz+SX, cycloxaprid+SX, (E)-N-{1-[(6-chloropyridin-3-yl)methyl]pyridine-2(1H)-ylidene}-2,2,2-trifluoroacetamide (1689566-03-7)+SX.

Examples of the combination of the Present active ingredient of the above sub group a-7 and the Present compound: chlorantraniliprole+SX, cyantraniliprole+SX, cycloniliprole+SX, flubendiamide+SX, tetraniliprole+SX, cyhalodiamide+SX, a compound represented by the following formula:

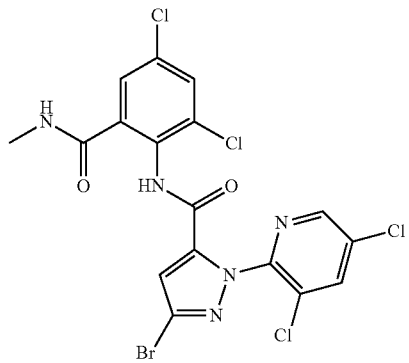 [SMILES: CNC(=O)c1cc(Cl)cc(Cl)c1NC(=O)c1cc(Br)nn1-c1ncc(Cl)cc1Cl]

(1104384-14-6)+SX.

Examples of the combination of the Present ingredient of the above sub group a-8 and the Present compound:

*Beauveria bassiana*+SX, *Beauveria brongniartii*+SX, *Paecilomyces fumosoroseus*+SX, *Paecilomyces lilacinus*+SX, *Paecilomyces tenuipes*+SX, *Verticillium lecani*+SX, *Arthrobotrys dactyloides*+SX, *Bacillus thuringiensis*+SX, *Bacillus firmus*+SX, *Bacillus megaterium*+SX, *Hirsutella rhossiliensis*+SX, *Hirsutella minnesotensis*+SX, *Monacrosporium phymatopagus*+SX, *Pasteuria nishizawae*+SX, *Pasteuria penetrans*+SX, *Pasteuria usgae*+SX, *Verticillium chlamydosporium*+SX.

Examples of the combination of the Present ingredient of the above sub group a-9 and the Present compound:

abamectin+SX, fluazaindolizine+SX, fluensulfone+SX, fluopyram+SX, tioxazafen+SX.

Examples of the combination of the Present ingredient of the above sub group a-10 and the Present compound:

spinetoram+SX, spinosad+SX, emamectin-benzoate+SX, lepimectin+SX, milbemectin+SX, hydroprene+SX, kinoprene+SX, methoprene+SX, fenoxycarb+SX, pyriproxyfen+SX, methyl bromide+SX, chloropicrin+SX, sulfuryl fluoride+SX, sodium aluminium fluoride or chiolite+SX, borax+SX, boric acid+SX, disodium octaborate+SX, sodium borate+SX, sodium metaborate+SX, tartar emetic+SX, dazomet+SX, metam+SX, pymetrozine+SX, pyrifluquinazone+SX, clofentezine+SX, hexythiazox+SX, diflovidazin+SX, etoxazole+SX, diafenthiuron+SX, azocyclotin+SX, cyhexatin+SX, fenbutatin oxide+SX, propargite+SX, tetradifon+SX, chlorfenapyr+SX, DNOC+SX, sulfluramid+SX, bensultap+SX, cartap+SX, cartap hydrochloride+SX, thiocyclam+SX, thiosultap-disodium+SX, thiosultap-monosodium+SX, bistrifluron+SX, chlorfluazuron+SX, diflubenzuron+SX, fluazuron+SX, flucycloxuron+SX, flufenoxuron+SX, hexaflumuron+SX, lufenuron+SX, novaluron+SX, noviflumuron+SX, teflubenzuron+SX, triflumuron+SX, buprofezin+SX, cyromazine+SX, chromafenozide+SX, halofenozide+SX, methoxyfenozide+SX, tebufenozide+SX, amitraz+SX, hydramethylnon+SX, acequinocyl+SX, fluacrypyrim+SX, bifenazate+SX, fenazaquin+SX, fenpyroximate+SX, pyridaben+SX, pyrimidifen+SX, tebufenpyrad+SX, tolfenpyrad+SX, rotenone+SX, indoxacarb+SX, metaflumizone+SX, spirodiclofen+SX, spiromesifen+SX, spirotetramat+SX, aluminium phosphide+SX, calcium phosphide+SX, phosphine+SX, zinc phosphide+SX, calcium cyanide+SX, potassium cyanide+SX, sodium cyanide+SX, cyenopyrafen+SX, cyflumetofen+SX, pyflubumide+SX, flonicamid+SX, azadirachtin+SX, benzoximate+SX, bromopropylate+SX, chinomethionat+SX, dicofol+SX, pyridalyl+SX, lime sulfur+SX, sulfur+SX, machine oil+SX, nicotine+SX, nicotine-sulfate+SX, afidopyropen+SX, flometoquin+SX, metoxadiazone+SX, pyriminostrobin+SX, N-[3-chloro-1-(pyridin-3-yl)-1H-pyrazol-4-yl]-N-ethyl-3-(3,3,3-trifluoropropylsulfanyl)propanamide (1477919-27-9)+SX, N-[3-chloro-1-(pyridin-3-yl)-1H-pyrazol-4-yl]-N-ethyl-3-(3,3,3-trifluoropropylsulfanyl)propanamide (1477919-27-9)+SX, 5-(1,3-dioxan-2-yl)-4-[4-(trifluoromethyl)benzyloxy]pyridine (1449021-97-9)+SX.

Examples of the combination of the Present active ingredient of the above sub group b-1 and the Present compound:
benalaxyl+SX, benalaxyl-M+SX, furalaxyl+SX, metalaxyl+SX, metalaxyl-M+SX, oxadixyl+SX, ofurace+SX.

Examples of the combination of the Present ingredient of the above sub group b-2 and the Present compound:
benomyl+SX, carbendazim+SX, fuberidazole+SX, thiabendazole+SX, thiophanate+SX, thiophanate-methyl+SX.

Examples of the combination of the Present ingredient of the above sub group b-3 and the Present compound:
ethaboxam+SX.

Examples of the combination of the Present ingredient of the above sub group b-4 and the Present compound:
benodanil+SX, flutolanil+SX, mepronil+SX, isofetamid+SX, fenfuram+SX, carboxin+SX, oxycarboxin+SX, thifluzamide+SX, benzovindiflupyr+SX, bixafen+SX, fluxapyroxad+SX, furametpyr+SX, isopyrazam+SX, penflufen+SX, penthiopyrad+SX, sedaxane+SX, pydiflumetofen+SX, boscalid+SX, pyraziflumid+SX, 3-difluoromethyl-N-methoxy-1-methyl-N-[(1R)-1-methyl-2-(2,4,6-trichlorophenyl)ethyl]pyrazol-4-carboxamide (1639015-48-7)+SX, 3-difluoromethyl-N-methoxy-1-methyl-N-[(1S)-1-methyl-2-(2,4,6-trichlorophenyl)ethyl]pyrazol-4-carboxamide (1639015-49-8)+SX, N-cyclopropyl-3-(difluoromethyl)-5-fluoro-N-(5-chloro-2-isopropylbenzyl)-1-methyl-1H-pyrazole-4-carboxamide (1255734-28-1)+SX, 3-difluoromethyl-1-methyl-N-(1,1,3-trimethylindan-4-yl)pyrazole-4-carboxamide (141573-94-6)+SX, 3-difluoromethyl-1-methyl-N-[(3R)-1,1,3-trimethylindan-4-yl]pyrazole-4-carboxamide (1352994-67-2)+SX, 3-difluoromethyl-N-(7-fluoro-1,1,3-trimethylindan-4-yl)-1-methylpyrazole-4-carboxamide (1383809-87-7)+SX, 3-difluoromethyl-N-[(3R)-7-fluoro-1,1,3-trimethylindan-4-yl]-1-methylpyrazole-4-carboxamide (1513466-73-3)+SX.

Examples of the combination of the Present ingredient of the above sub group b-5 and the Present compound:
azoxystrobin+SX, coumoxystrobin+SX, enoxastrobin+SX, flufenoxystrobin+SX, picoxystrobin+SX, pyraoxystrobin+SX, mandestrobin+SX, pyraclostrobin+SX, pyrametostrobin+SX, triclopyricarb+SX, kresoxim-methyl+SX, trifloxystrobin+SX, dimoxystrobin+SX, fenaminstrobin+SX, metominostrobin+SX, orysastrobin+SX, famoxadone+SX, fluoxastrobin+SX, fenamidone+SX, pyribencarb+SX.

Examples of the combination of the Present ingredient of the above sub group b-6 and the Present compound:
cyazofamid+SX, amisulbrom+SX, binapacryl+SX, meptyldinocap+SX, dinocap+SX, fluazinam+SX.

Examples of the combination of the Present ingredient of the above sub group b-7 and the Present compound:
silthiofam+SX.

Examples of the combination of the Present active ingredient of the above sub group b-8 and the Present compound:
cyprodinil+SX, mepanipyrim+SX, pyrimethanil+SX.

Examples of the combination of the Present ingredient of the above sub group b-9 and the Present compound:
fenpiclonil+SX, fludioxonil+SX.

Examples of the combination of the Present ingredient of the above sub group b-10 and the Present compound:
biphenyl+SX, chloroneb+SX, dicloran+SX, quintozene+SX, tecnazene+SX, tolclofos-methyl+SX.

Examples of the combination of the Present ingredient of the above sub group b-11 and the Present compound:
azaconazole+SX, bitertanol+SX, bromuconazole+SX, cyproconazole+SX, difenoconazole+SX, diniconazole+SX, diniconazole-M+SX, epoxiconazole+SX, etaconazole+SX, fenbuconazole+SX, fluquinconazole+SX, flusilazole+SX, flutriafol+SX, hexaconazole+SX, imibenconazole+SX, ipconazole+SX, ipfentrifluconazole+SX, mefentriflucon-azole+SX, metconazole+SX, myclobutanil+SX, penconazole+SX, propiconazole+SX, simeconazole+SX, tebuconazole+SX, tetraconazole+SX, triadimefon+SX, triadimenol+SX, triticonazole+SX, prothioconazole+SX, triforine+SX, pyrifenox+SX, pyrisoxazole+SX, fenarimol+SX, nuarimol+SX, imazalil+SX, oxpoconazole+SX, oxpoconazole fumarate+SX, pefurazoate+SX, prochloraz+SX, triflumizole+SX.

Examples of the combination of the Present ingredient of the above sub group b-12 and the Present compound:
dimethomorph+SX, flumorph+SX, pyrimorph+SX, benthiavalicarb+SX, benthivalicarb-isopropyl+SX, iprovalicarb+SX, valifenalate+SX, mandipropamid+SX.

Examples of the combination of the Present ingredient of the above sub group b-13 and the Present compound:
oxathiapiprolin+SX.

Examples of the combination of the Present ingredient of the above sub group b-14 and the Present compound:
picarbutrazox+SX.

Examples of the combination of the Present ingredient of the above sub group b-15 and the Present compound:
ferbam+SX, mancozeb+SX, maneb+SX, metiram+SX, propineb+SX, thiram+SX, zineb+SX, ziram+SX.

Examples of the combination of the Present active ingredient of the above sub group b-16 and the Present compound:
captan+SX, captafol+SX, folpet+SX.

Examples of the combination of the Present ingredient of the above sub group b-17 and the Present compound:
*Agrobacterium radiobactor* strains (such as its 84 strain)+SX, *Bacillus amyloliquefaciens*+SX, *Bacillus amyloliquefaciens* strain QST713+SX, *Bacillus amyloliquefaciens* strain FZB24+SX, *Bacillus amyloliquefaciens* strain MBI600+SX, *Bacillus amyloliquefaciens* strain D747+SX, *Bacillus amyloliquefaciens* strain AT332+SX, *Bacillus amyloliquefaciens* strain PTA4838+SX, *Bacillus pumilus*+SX, *Bacillus simplex* CGF2856 strains (such as its CGF2856 strain)+SX, *Bacillus subtilis*+SX, *Bacillus subtilis* strain QST713+SX, *Bacillus subtilis* strain HAI0404+SX, *Bacillus subtilis* strain Y1336+SX, *Variovorax paradoxus* strains (such as its CGF4526 strain)+SX, *Erwinia carotovora* strains (such as its CGE234M403 strain)+SX, *Pseudomonas fluorescens* strains (such as its G7090 strain)+SX, *Talaromyces flavus* strains (such as its SAY-Y-94-01 strain)+SX, *Trichoderma atroviride* strains (such as its SKT-1 strain)+SX, *Trichoderma harzianum* strains+SX, Harpin protein+SX.

Examples of the combination of the Present ingredient of the above sub group b-18 and the Present compound:

bupirimate+SX, dimethirimol+SX, ethirimol+SX, hymexazole+SX, octhilinone+SX, oxolinic acid+SX, diethofencarb+SX, zoxamide+SX, pencycuron+SX, fluopicolide+SX, phenamacril+SX, diflumetorim+SX, tolfenpyrad+SX, fentin acetate+SX, fentin chloride+SX, fentin hydroxide+SX, ametoctradin+SX, blasticidin-S+SX, kasugamycin+SX, streptomycin+SX, oxytetracycline+SX, quinoxyfen+SX, proquinazid+SX, chlozolinate+SX, dimethachlone+SX, iprodione+SX, procymidone+SX, vinclozolin+SX, edifenphos+SX, iprobenfos+SX, pyrazophos+SX, isoprothiolane+SX, etridiazole+SX, iodocarb+SX, propamocarb+SX, prothiocarb+SX, aldimorph+SX, dodemorph+SX, fenpropidin+SX, fenpropimorph+SX, piperalin+SX, spiroxamine+SX, tridemorph+SX, fenhexamid+SX, fenpyrazamine+SX, pyributicarb+SX, naftifine+SX, terbinafine+SX, polyoxins+SX, phthalide+SX, pyroquilon+SX, tricyclazole+SX, carpropamid+SX, diclocymet+SX, fenoxanil+SX, tolprocarb+SX, acibenzolar-S-methyl+SX, probenazole+SX, tiadinil+SX, isotianil+SX, laminarin+SX, cymoxanil+SX, fosetyl+SX, teclofthalam+SX, triazoxide+SX, flusulfamide+SX, diclomezine+SX, methasulfocarb+SX, cyflufenamid+SX, metrafenone+SX, pyriofenone+SX, dodine+SX, flutianil+SX, ferimzone+SX, tebufloquin+SX, validamycin+SX, basic copper chloride+SX, copper(II) hydroxide+SX, basic copper sulphate+SX, Dodecylbenzenesulphonic acid bisethylenediamine copper [II] salt (DBEDC)+SX, organocopper+SX, sulfur+SX, chlorothalonil+SX, dichlofluanid+SX, tolylfluanid+SX, guazatine+SX, iminoctadine+SX, anilazine+SX, dithianon+SX, chinomethionat+SX, fluoroimide+SX, dipymetitrone+SX, quinofumelin+SX, dichlobentiazox+SX, 3-chloro-5-phenyl-6-methyl-4-(2,6-difluorophenyl) pyridazine (1358061-55-8)+SX, fenpicoxamid+SX, N'-[4-({3-[(4-chlorophenyl)methyl]-1,2,4-thiadiazol-5-yl}oxy-2,5-dimethylphenyl]-N-ethyl-N-methylmethaneimidamide (1202781-91-6)+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl=methanesulfonate (1360819-11-9)+SX, 4-(2-bromo-4-fluorophenyl)-N-(2-chloro-6-fluorophenyl)-1,3-dimethyl-1H-pyrazole-5-amine (1362477-26-6)+SX, 2,2-dimethyl-9-fluoro-5-(quinolin-3-yl)-2,3-dihydrobenzo[f][1,4]oxazepine (1207749-50-5)+SX, 2-[6-(3-fluoro-4-methoxyphenyl)-5-methylpyridin-2-yl]quinazoline (1257056-97-5)+SX, 5-fluoro-2-[(4-methylphenyl)methoxy]-4-pyrimidineamine (1174376-25-0)+SX, 5-fluoro-4-imino-3-methyl-1-tosyl-3,4-dihydropyrimidine-2(1H)-one (1616664-98-2)+SX, N'-(2,5-dimethyl-4-phenoxyphenyl)-N-ethyl-N-methyl-methaneimidamide (1052688-31-9)+SX, N'-{4-[(4,5-dichlorothiazol-2-yl)oxy]-2,5-dimethylphenyl}-N-ethyl-N-methylmethaneimidamide (929908-57-6)+SX, ethyl (2Z)-3-amino-2-cyano-3-phenylacrylate (39491-78-6)+SX, N-{(2-chlorothiazol-5-yl)methyl}-N-ethyl-6-methoxy-3-nitropyridine-2-amine (1446247-98-8)+SX, 1-[2-({[1-(4-chlorophenyl)-1H-pyrazol-3-yl]oxy}methyl)-3-methylphenyl]-4-methyl-5-oxo-4,5-dihydro-1H-tetrazole (1472649-01-6)+SX.

Examples of the combination of the Present ingredient of the above sub group c-1 and the Present compound:

ethephon+SX, chlormequat+SX, chlormequat-chloride+SX, mepiquat+SX, mepiquat-chloride+SX, Gibberellin A3+SX, abscisic acid+SX, Kinetin+SX, benzyladenine+SX, forchlorfenuron+SX, thidiazuron+SX.

Examples of the combination of the Present ingredient of the above sub group c-2 and the Present compound:

*Glomus* spp.+SX, *Glomus intraradices*+SX, *Glomus mosseae*+SX, *Glomus aggregatum*+SX, *Glomus etunicatum*+SX.

Examples of the combination of the Present ingredient of the above sub group c-3 and the Present compound:

*Bradyrhizobium elkani*+SX, *Bradyrhizobium japonicum*+SX, *Bradyrhizobium lupini*+SX, *Rhizobium leguminosarum* bv. *trifolii*+SX, *Rhizobium leguminosarum* bv. *phaseoli*+SX, *Rhizobium leguminosarum* bv. *viciae*+SX, *Sinorhizobium meliloti*+SX, *Rhizobium* spp.+SX.

Examples of the combination of the Present active ingredient of the above sub group d and the Present compound:

benoxacor+SX, cloquintocet-mexyl+SX, cyometrinil+SX, dichlormid+SX, fenchlorazole-ethyl+SX, fenclorim+SX, flurazole+SX, furilazole+SX, mefenpyr-diethyl+SX, MG191 (2-(dichloromethyl)-2-methyl-1,3-dioxolane)+SX, oxabetrinil+SX, allidochlor+SX, isoxadifen-ethyl+SX, cyprosulfamide+SX, fluxofenim+SX, 1,8-naphthalic anhydride+SX, AD-67 4-(dichloroacetyl)-1-oxa-4-azaspiro[4.5]decane)+SX.

Examples of the harmful arthropod on which the compound of the present invention has efficacies include harmful insects and harmful mites. Specific examples of harmful arthropods include the followings.

Hemiptera Pests:

Delphacidae (for example, *Laodelphax striatellus, Nilaparvata lugens, Sogatella furcifera, Peregrinus maidis, Javesella pellucida, Perkinsiella saccharicida*, or *Tagosodes orizicolus*);

Cicadellidae (for example, *Nephotettix cincticeps, Nephotettix virescens, Nephotettix nigropictus, Recilia dorsalis, Empoasca onukii, Empoasca fabae, Dalbulus maidis*, or *Cofana spectra*);

Cercopidae (for example, *Mahanarva posticata*, or *Mahanarva fimbriolata*);

Aphididae (for example, *Aphis fabae, Aphis glycines, Aphis gossypii, Aphis pomi, Aphis spiraecola, Myzus persicae, Brachycaudus helichrysi, Brevicoryne brassicae*, Rosy apple aphid (*Dysaphis plantaginea*), *Lipaphis erysimi, Macrosiphum euphorbiae, Aulacorthum solani, Nasonovia ribisnigri, Rhopalosiphum padi, Rhopalosiphum maidis, Toxoptera citricidus, Hyalopterus pruni, Melanaphis sacchari, Tetraneura nigriabdominalis, Ceratovacuna lanigera*, or *Eriosoma lanigerum*);

Phylloxeridae (for example, *Daktulosphaira vitifoliae*, Pecan phylloxera (*Phylloxera devastatrix*), Pecan leaf *phylloxera* (*Phylloxera notabilis*), or Southern pecan leaf *phylloxera* (*Phylloxera russellae*));

Adelgidae (for example, *Adelges tsugae, Adelges piceae*, or *Aphrastasia pectinatae*);

Pentatomidae (for example, *Scotinophara lurida*, Malayan rice black bug (*Scotinophara coarctata*), *Nezara antennata, Eysarcoris aeneus, Eysarcoris lewisi, Eysarcoris ventralis, Eysarcoris annamita, Halyomorpha halys, Nezara viridula*, Brown stink bug (*Euschistus heros*), Red banded stink bug (*Piezodorus guildinii*), *Oebalus pugnax, Dichelops melacanthus*);

Cydnidae (for example, Burrower brown bug (*Scaptocoris castanea*));

Alydidae (for example, *Riptortus pedestris, Leptocorisa chinensis*, or *Leptocorisa acuta*);

Coreidae (for example, *Cletus punctiger*, or *Leptoglossus australis*);

Lygaeidae (for example, *Caverelius saccharivorus, Togo hemipterus*, or *Blissus leucopterus*);

Miridae (for example, *Trigonotylus caelestialium, Stenotus rubrovittatus, Stenodema calcarata*, or *Lygus lineolaris*);

Aleyrodidae (for example, *Trialeurodes vaporariorum, Bemisia tabaci, Dialeurodes citri, Aleurocanthus spiniferus, Aleurocanthus camelliae*, or *Pealius euryae*);

Diaspididae (for example, *Abgrallaspis cyanophylli, Aonidiella aurantii, Diaspidiotus perniciosus, Pseudaulacaspis pentagona, Unaspis yanonensis*, or *Unaspis citri*);

Coccidae (for example, *Ceroplastes rubens*);

Margarodidae (for example, *Icerya purchasi*, or *Icerya seychellarum*);

Pseudococcidae (for example, *Phenacoccus solani, Phenacoccus solenopsis, Planococcus kraunhiae, Planococcus comstocki, Planococcus citri, Pseudococcus calceolariae, Pseudococcus longispinus*, or *Brevennia rehi*);

Psyllidae (for example, *Diaphorina citri, Trioza erytreae, Cacopsylla pyrisuga, Cacopsylla chinensis, Bactericera cockerelli*, or Pear psylla (*Cacopsylla pyricola*));

Tingidae (for example, *Corythucha ciliata, Corythucha marmorata, Stephanitis nashi*, or *Stephanitis pyrioides*);

Cimicidae (for example, *Cimex lectularius*); and

Cicadidae (for example, Giant Cicada (*Quesada gigas*)).

Lepidoptera

Crambidae (for example, *Chilo suppressalis*, Darkheaded stem borer (*Chilo polychrysus*), White stem borer (*Scirpophaga innotata*), *Scirpophaga incertulas, Rupela albina, Cnaphalocrocis medinalis, Marasmia patnalis, Marasmia exigua, Notarcha derogata, Ostrinia furnacalis*, European corn borer (*Ostrinia nubilalis*), *Hellula undalis, Herpetogramma luctuosale, Pediasia teterrellus, Nymphula depunctalis*, Sugarcane borer (*Diatraea saccharalis*));

Pyralidae (for example, *Elasmopalpus lignosellus* or *Plodia interpunctella*);

Noctuidae (for example, *Spodoptera litura, Spodoptera exigua, Mythimna separata, Mamestra brassicae, Sesamia inferens, Spodoptera mauritia, Naranga aenescens, Spodoptera frugiperda, Spodoptera exempta, Agrotis ipsilon, Autographa nigrisigna, Plusia festucae*, Soybean looper (*Chrysodeixis includens*), *Trichoplusia* spp., *Heliothis* spp. (for example, *Heliothis virescens*), *Helicoverpa armigera, Helicoverpa* spp. (for example, *Helicoverpa zea*), Velvetbean caterpillar (*Anticarsia gemmatalis*), Cotton leafworm (*Alabama argillacea*), Hop vine borer (*Hydraecia immanis*)), Pieridae (for example, *Pieris rapae*);

Tortricidae (for example, *Grapholita molesta, Grapholita dimorpha, Leguminivora glycinivorella, Matsumuraeses azukivora, Adoxophyes orana fasciata, Adoxophyes honmai, Homona magnanima, Archips fuscocupreanus, Cydia pomonella, Tetramoera schistaceana*, Bean Shoot Borer (*Epinotia aporema*), or Citrus fruit borer (*Ecdytolopha aurantiana*));

Gracillariidae (for example, *Caloptilia theivora*, or *Phyllonorycter ringoniella*);

Carposinidae (for example, *Carposina sasakii*);

Lyonetiidae (for example, Coffee Leaf miner (*Leucoptera coffeela*), *Lyonetia clerkella*, or *Lyonetia prunifoliella*);

Lymantriidae (for example, *Lymantria* spp. (for example, *Lymantria dispar*), or *Euproctis* spp. (for example, *Euproctis pseudoconspersa*));

Plutellidae (for example, *Plutella xylostella*);

Gelechiidae (for example, *Anarsia lineatella, Helcystogramma triannulellum, Pectinophora gossypiella, Phthorimaea operculella*, or *Tuta absolut*);

Arctiidae (for example, *Hyphantria cunea*);

Castniidae (for example, Giant Sugarcane borer (*Telchin licus*));

Cossidae (for example, *Cosus insularis*);

Geometridae (for example, *Ascotis selenaria*);

Limacodidae (for example, *Parasa lepida*);

Stathmopodidae (for example, *Stathmopoda masinissa*);

Sphingidae (for example, *Acherontia lachesis*);

Sesiidae (for example, *Nokona feralis*);

Hesperiidae (for example, *Parnara guttata*).

Thysanoptera

Thripidae (for example, *Frankliniella occidentalis, Thrips palmi, Scirtothrips dorsalis, Thrips tabaci, Frankliniella intonsa, Stenchaetothrips biformis*, or *Echinothrips americanus*);

Phlaeothripidae (for example, *Haplothrips aculeatus*).

Diptera

Anthomyiidae (for example, *Delia platura* or *Delia antiqua*);

Ulidiidae (for example, *Tetanops myopaeformis*);

Agromyzidae (for example, *Agromyza oryzae, Liriomyza sativae, Liriomyza trifolii*, or *Chromatomyia horticola*);

Chloropidae (for example, *Chlorops oryzae*);

Tephritidae (for example, *Bactrocera cucurbitae, Bactrocera dorsalis, Bactrocera latifrons, Bactrocera oleae, Bactrocera tryoni*, or *Ceratitis capitata*);

Ephydridae (for example, *Hydrellia griseola, Hydrellia philippina, Hydrellia sasakii*, or Ephydridae);

Drosophilidae (for example, *Drosophila suzukii*);

Phoridae (for example, *Megaselia spiracularis*);

Psychodidae (for example, *Clogmia albipunctata*);

Sciaridae (for example, *Bradysia difformis*);

Cecidomyiidae (for example, *Mayetiola destructor*, or *Orseolia oryzae*);

Diopsidae (for example, *Diopsis macrophthalma*);

Tipulidae (for example, *Tipula aino*, Common cranefly (*Tipula oleracea*), or European cranefly (*Tipula paludosa*)).

Coleoptera

Chrysomelidae (for example, *Diabrotica virgifera virgifera, Diabrotica undecimpunctata howardi, Diabrotica barberi, Diabrotica virgifera zeae, Diabrotica balteata*, Cucurbit Beetle (*Diabrotica speciosa*), *Cerotoma trifurcata, Oulema melanopus, Aulacophora femoralis, Phyllotreta striolata*, Cabbage flea beetle (*Phyllotreta cruciferae*), Western black flea beetle (*Phyllotreta pusilla*), Cabbage stem flea beetle (*Psylliodes chrysocephala*), *Leptinotarsa decemlineata, Oulema oryzae, Colaspis brunnea, Chaetocnema pulicaria, Chaetocnema confi, Epitrix cucumeris, Dicladispa armigera*, Grape *Colaspis* (*Colaspis brunnea*), southern corn leaf beetle (*Myochrous denticollis*), *Laccoptera quadrimacu*, or *Epitrix hirtipennis*);

Carabidae (for example, Seedcorn beetle (*Stenolophus lecontei*), or Slender seedcorn beetle (*Clivina impressifrons*));

Scarabaeidae (for example, *Anomala cuprea, Anomala rufocuprea, Anomala albopilosa, Popillia japonica, Heptophylla picea*, European Chafer (*Rhizotrogus majalis*), *Tomarus gibbosus, Holotrichia* spp., or *Phyllophaga* spp. (for example, *Phyllophaga crinita*), *Diloboderus* spp. (for example, *Diloboderus abderus*));

Curculionidae (for example, *Araecerus coffeae, Cylas formicarius, Euscepes postfasciatus, Hypera postica, Sitophilus zeamais, Echinocnemus squameus, Lissorhoptrus oryzophilus, Rhabdoscelus lineatocollis, Anthonomus grandis, Sphenophorus venatus*, Southern Corn Billbug (*Sphenophorus callosus*), Soybean stalk weevil (*Sternechus subsignatus*), Sugarcane wiivil (*Sphenophorus levis*), *Scepticus griseus, Scepticus uniformis, Zabrotes subfasciatus*,

*Tomicus piniperda*, Coffee Berry Borer (*Hypothenemus hampei*), *Aracanthus* spp. (for example, *Aracanthus mourei*), and cotton root borer (*Eutinobothrus brasiliensis*));

Tenebrionidae (for example, *Tribolium castaneum*, or *Tribolium confusum*);

Coccinellidae (for example, *Epilachna vigintioctopunctata*);

Bostrychidae (for example, *Lyctus brunneus*);

Ptinidae;

Cerambycidae (for example, *Anoplophora malasiaca*, or *Migdolus fryanus*);

Elateridae (for example, *Melanotus okinawensis, Agriotes fuscicollis, Melanotus legatus, Anchastus* spp., *Conoderus* spp., *Ctenicera* spp., *Limonius* spp., or *Aeolus* spp.); and Staphylinidae (for example, *Paederus fuscipes*).

Orthoptera

Acrididae (for example, *Locusta migratoria, Dociostaurus maroccanus, Chortoicetes terminifera, Nomadacris septemfasciata*, Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), *Schistocerca gregaria*, Yellow-winged locust (*Gastrimargus musicus*), Spur-throated locust (*Austracris guttulosa*), *Oxya yezoensis, Oxya japonica*, or *Patanga succincta*);

Gryllotalpidae (for example, *Gryllotalpa africana*);

Gryllidae (for example, *Acheta domesticus*, or *Teleogryllus emma*);

Tettigoniidae (for example, Mormon cricket (*Anabrus simplex*).

Hymenoptera

Tenthredinidae (for example, *Athalia rosae*, and *Athalia japonica*); and

Formicidae (for example, Brown leaf-cutting ant (*Atta capiguara*)).

Blattodea

Blattellidae (for example, *Blattella germanica*);

Blattidae (for example, *Periplaneta fuliginosa, Periplaneta americana, Periplaneta brunnea*, or *Blatta orientalis*);

Termitidae (for example, *Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Hodotermopsis sjostedti, Coptotermes guangzhouensis, Reticulitermes amamianus, Reticulitermes miyatakei, Reticulitermes kanmonensis, Nasutitermes takasagoensis, Pericapritermes nitobei, Sinocapritermes mushae*, or *Cornitermes cumulans*).

Acari

Tetranychidae (for example, *Tetranychus urticae, Tetranychus kanzawai, Tetranychus evansi, Panonychus citri, Panonychus ulmi*, or *Oligonychus* spp.);

Eriophyidae (for example, *Aculops pelekassi, Phyllocoptruta citri, Aculops lycopersici, Calacarus carinatus, Acaphylla theavagrans, Eriophyes chibaensis, Aculus schlechtendali, Aceria diospyri, Aceria tosichella*, or *Shevtchenkella* sp.);

Tarsonemidae (for example, *Polyphagotarsonemus latus*);

Tenuipalpidae (for example, *Brevipalpus phoenicis*);

Tuckerellidae;

Ixodidae (for example, *Haemaphysalis longicornis, Haemaphysalis flava, Dermacentor taiwanensis, Dermacentor variabilis, Ixodes ovatus, Ixodes persulcatus, Ixodes scapularis, Amblyomma americanum, Boophilus microplus*, or *Rhipicephalus sanguineus*);

Acaridae (for example, *Tyrophagus putrescentiae*, or *Tyrophagus similis*);

Pyroglyphidae (for example, *Dermatophagoides farinae*, or *Dermatophagoides pteronyssinus*);

Cheyletidae (for example, *Cheyletus eruditus, Cheyletus malaccensis, Cheyletus moorei*, or *Cheyletiella yasguri*);

Sarcoptidae (for example, *Otodectes cynotis*, or *Sarcoptes scabiei*);

Demodicidae (for example, *Demodex canis*);

Listrophoridae;

Haplochthoniidae;

Macronyssidae (for example, *Ornithonyssus bacoti*, or *Ornithonyssus sylviarum*);

Dermanyssidae (for example, *Dermanyssus gallinae*);

Trombiculidae (for example, *Leptotrombidium akamushi*).

The compound (M-14) has an efficacy for controlling harmful arthropod.

The agent for controlling harmful arthropods of the present invention comprises the compound of the present invention and an inert active carrier. The agent for controlling harmful arthropods is usually prepared by mixing the compound of the present invention with an inert active carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations and tablets and the others. Such formulations may be processed into mosquito repellent coils, electric mosquito repellent mats, liquid mosquito formulations, smoking agents, fumigants, sheet formulations, spot-on formulations or formulations for oral treatment. Also, the agent for controlling harmful arthropods of the present invention may be mixed with other pesticides, miticides, nematicides, fungicides, plant growth regulators, herbicides, and synergists.

The agent for controlling harmful arthropods of the present invention comprises usually 0.01 to 95% by weight of the compound of the present invention.

Examples of the solid carrier to be used in the formulation include fine powders or granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate or hydrated silica) or chemical fertilizers (for example, ammonium sulfate, ammonium phosphate, ammonium nitrate, urea or ammonium chloride) and the others; as well as synthetic resins (for Example, polyester resins such as polypropylene, polyacrylonitrile, polymethylmethacrylate and polyethylene terephthalate; nylon resins (for Example, nylon-6, nylon-11 and nylon-66); polyamide resins; polyvinyl chloride, polyvinylidene chloride, vinyl chloride-propylene copolymers, and the others).

Examples of the above-mentioned liquid carriers include water; alcohols (for example, methanol, ethanol, isopropyl alcohol, butanol, hexanol, benzyl alcohol, ethylene glycol, propylene glycol or phenoxy ethanol); ketones (for Example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl myristate, ethyl oleate, diisopropyl adipate, diisobutyl adipate or propylene glycol monomethyl ether acetate); nitriles (for Example, acetonitrile or isobutyronitrile); ethers (for Example, diisopropyl ether, 1,4-dioxane, ethyleneglycol dimethyl ether, diethyleneglycol dimethyl ether, diethylene glycol monomethyl ether, propylene glycol monomethyl ether, dipropylene glycol monomethyl ether or 3-methoxy-3-methyl-1-butanol); acid amides (for example, dimethylformamide (DMF) or dimethylacetamide); halogenated hydrocarbons (for example, dichloromethane, trichloroethane, carbon tetrachloride); sulfoxides (for example, dimethyl sulfoxide (DMSO)); propylene carbonate; and vegetable oils (for example, soybean oil or cottonseed oil).

Examples of the above-mentioned gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), and BHA (a mixture of 2-tert-butyl-4-methoxyphenol and 3-tert-butyl-4-methoxyphenol).

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by mixing the compound of the present invention with the above-mentioned base material, kneading the mixture, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor and peanut oil.

The method for controlling harmful arthropods of the present invention is conducted by applying an effective amount of the compound of the present invention to a harmful arthropod directly and/or a habitat thereof (for example, plant bodies, soil, an interior of a house, animal bodies). In the method for controlling harmful arthropods of the present invention, the Present compound is usually used in the form of an agent for controlling harmful arthropods.

When an agent for controlling harmful arthropods of the present invention is used for controlling harmful arthropods in an agricultural field, the application dose as an amount of the compound of the present invention is usually within a range from 1 to 10,000 g per 10,000 m². The emulsifiable concentrate, the wettable powder, or the flowable formulation etc. of an agent for controlling harmful arthropods of the present invention is usually applied by diluting it with water in such a way that a concentration of the compound of the present invention is within a range from 0.01 to 10,000 ppm. The granular formulation, or the dust formulation etc., is usually applied as itself without diluting it.

These formulations or an aqueous dilution thereof can be sparged directly to harmful arthropods or plants (such as crops) to be protected from harmful arthropods, and also may be applied to the soil of crop land in order to control harmful arthropods which live there.

The resin preparation which is processed into a sheet or a string may be applied by winding a plant with a sheet or a string of the resin preparation, putting a string of the resin preparation around a crop so that the plant is surrounded by the string, or laying a sheet of the resin preparation on the soil surface near the root of a plant.

When the agent for controlling harmful arthropods of the present invention is used to control harmful arthropods that live inside a house, the application dose as an amount of the Present compound is usually within a range from 0.01 to 1,000 mg per 1 m² of an area to be treated, in the case of using it on a planar area. In the case of using it spatially, the application dose as an amount of the Present compound is usually within a range from 0.01 to 500 mg per 1 m³ of the space to be treated. When the agent for controlling harmful arthropods of the present invention is formulated into emulsifiable concentrates, wettable powders, flowables or the others, such formulations are usually applied after diluting it with water in such a way that a concentration of the active ingredient is within a range from 0.1 to 10,000 ppm, and then sparging it. In the case of being formulated into oil solutions, aerosols, smoking agents, poison baits and the others, such formulations are used as itself without diluting it.

When the agent for controlling harmful arthropods of the present invention is sued for controlling external parasites of livestock such as cows, horses, pigs, sheep, goats and chickens and small animals such as dogs, cats, rats and mice, the pest control agent of the present invention can be applied to the animals by a known method in the veterinary field. Specifically, when systemic control is intended, the pest control agent of the present invention is administered to the animals as a tablet, a mixture with feed or a suppository, or by injection (including intramuscular, subcutaneous, intravenous and intraperitoneal injections). On the other hand, when non-systemic control is intended, the pest control agent of the present invention is applied to the animals by means of spraying of the oil solution or aqueous solution, pour-on or spot-on treatment, or washing of the animal with a shampoo formulation, or by putting a collar or ear tag made of the resin formulations to the animal. In the case of administering to an animal body, the dose of the Present compound is usually within a range from 0.1 to 1,000 mg per 1 kg of an animal body weight.

EXAMPLES

Hereinafter, the present invention is explained in more detail by using Preparation example, Formulation example, and Test example, however, the present invention should not be limited to these examples.

First, the preparation example of a compound of the present invention is shown below.

Preparation Example 1

To a mixture of 3-chloropyridine-2-carbonitrile 54 g and THF 300 mL was added dropwise 1M solution of methyl magnesium bromide in THF 500 mL under ice-cooling. The reaction mixture was stirred under ice-cooling for 2 hours. The resulting reaction mixture was added 2N hydrochloric acid under ice-cooling, and the mixture was stirred for 30 minutes. The mixture was made pH 8 by adding 1N aqueous sodium hydroxide solution, and the mixture was then extracted with ethyl acetate. The resulting organic layers were washed with saturated brine, and the organic layers were dried over anhydrous sodium sulfate. The organic layers were concentrated under reduced pressure to give an intermediate compound 1 58 g.

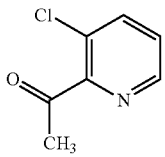

Intermediate compound 1: $^1$H-NMR (CDCl$_3$) δ: 8.55 (1H, dd), 7.80 (1H, dd), 7.38 (1H, dd), 2.70 (3H, s).

Preparation Example 2

To a suspension of sodium hydride (in oil, 60%) 57 g and DMF 560 mL was added dropwise ethanethiol 100 mL under ice-cooling. To the resulting mixture was added dropwise a mixture of the intermediate compound 1 204 g and DMF 190 mL under ice-cooling. The resulting reaction mixture was stirred for 1 hour under ice-cooling, and the mixture was added to ice water. The precipitated out solids were filtered, and washed with water. The obtained solids were dissolved into ethyl acetate, and the resulting solutions were washed with saturated brine, and the organic layers were dried over sodium sulfate. The resulting organic layers were concentrated under reduced pressure, and the obtained solids were then washed with hexane to give an intermediate compound 2 160 g.

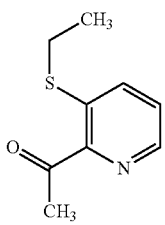

Intermediate compound 2:
$^1$H-NMR (CDCl$_3$) δ: 8.40 (1H, dd), 7.69 (1H, dd), 7.37 (1H, dd), 2.92 (2H, q), 2.72 (3H, s), 1.40 (3H, t).

Preparation Example 3

To a mixture of the intermediate compound 2 5.4 g, glyoxylic acid monohydrate 2.8 g, and methanol 90 mL was added dropwise a mixed solution of sodium hydroxide 2.4 g and methanol 60 mL under ice-cooling. The reaction mixture was stirred at 60° C. for 2 hours. The reaction mixture was allowed to stand to cool to room temperature, and thereto were then added acetic acid 11 mL and hydrazine monohydrate 2.3 g successively. The resulting mixture was stirred at 100° C. for 19 hours. The resulting mixture was allowed to stand to cool to room temperature, and thereto was then added saturated aqueous ammonium chloride solution, and the mixture was extracted with chloroform. The resulting organic layers were dried over sodium sulfate, and concentrated under reduced pressure. The resulting residue was subjected to silica gel chromatography to give an intermediate compound 3 3.8 g.

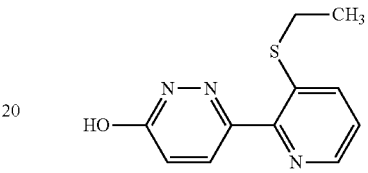

Intermediate compound 3: $^1$H-NMR (CDCl$_3$) δ: 10.60 (1H, br s), 8.43 (1H, dd), 8.13 (1H, d), 7.71 (1H, dd), 7.29 (1H, dd), 7.05 (1H, d), 2.95 (2H, q), 1.35 (3H, t).

Preparation Example 4

To a mixture of the intermediate compound 3 4.2 g and chloroform 60 mL was added 70% mCPBA 8.7 g under ice-cooling. The mixture was warmed to room temperature, and then stirred for 12 hours. To the resulting reaction mixture were added saturated aqueous sodium hydrogen carbonate solution, and aqueous sodium thiosulfate solution, and the mixture was extracted with chloroform. The resulting organic layers were dried over anhydrous sodium sulfate, and concentrated under reduced pressure to give an intermediate compound 4 represented by the following formula 4.7 g.

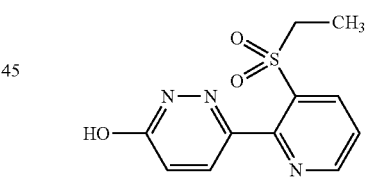

Intermediate compound 4: $^1$H-NMR (CDCl$_3$) δ: 11.66 (1H, s), 8.90 (1H, dd), 8.49 (1H, dd), 7.78 (1H, d), 7.61 (1H, dd), 7.10 (1H, d), 3.66 (2H, q), 1.38 (3H, t).

Preparation Example 5

To a mixture of the intermediate compound 4 2.0 g and toluene 8 mL was added one drop of DMF and phosphorus oxybromide 4.3 g successively. The mixture was stirred at 100° C. for 9 hours. The resulting mixture was allowed to stand to cool to room temperature, and water was then added thereto, and the mixture was extracted with chloroform. The resulting organic layers were washed with water and saturated brine, dried over sodium sulfate, and concentrated under reduced pressure. The resulting residue was subjected to silica gel chromatography to give an intermediate compound 5 represented by the following formula 2.1 g.

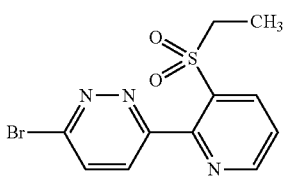

Intermediate compound 5: ¹H-NMR (CDCl₃) δ: 8.93 (1H, dd), 8.54 (1H, dd), 7.88-7.81 (2H, m), 7.66 (1H, dd), 3.89 (2H, q), 1.40 (3H, t).

Preparation Example 6

A mixture of the intermediate compound 5 300 mg, 3,5-difluorophenyl boronic acid 170 mg, tris(dibenzylideneacetone)palladium(0) 42 mg, 4,5-bis(diphenylphosphino)-9,9-dimethyl xanthene 53 mg, trisodium phosphate 12 hydrates 1.0 g, and dimethoxyethane 2 mL was stirred under heating at 80° C. for 7.5 hours. The resulting reaction mixture was allowed to stand to cool to room temperature, and thereto was then added saturated aqueous sodium hydrogen carbonate solution, and the mixture was extracted with ethyl acetate. The resulting organic layers were washed with water and saturated brine, dried over sodium sulfate, and concentrated under reduced pressure. The resulting residue was subjected to silica gel chromatography to give a compound 2 represented by the following formula 230 mg.

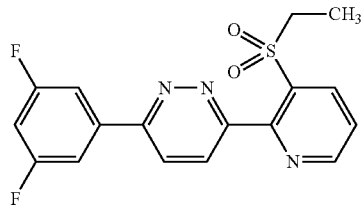 [SMILES: CCS(=O)(=O)c1cccnc1-c1ccc(-c2cc(F)cc(F)c2)nn1]

Compound 2: ¹H-NMR (CDCl₃) δ: 8.97-8.95 (1H, m), 8.58-8.55 (1H, m), 8.07 (1H, d), 8.00 (1H, d), 7.74-7.64 (3H, m), 7.02-6.96 (1H, m), 3.97 (2H, q), 1.44 (3H, t).

Preparation Example 7

The compounds that were prepared according to the similar method to the Preparation Example 6, and their physical property values are shown below.

A compound represented by formula (X):

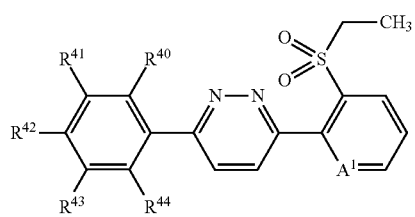

(X)

[wherein, each of A¹, R⁴⁰, R⁴¹, R⁴², R⁴³, and R⁴⁴ represents any group indicated in Table 18].

TABLE 18

| Compound | A¹ | R⁴⁰ | R⁴¹ | R⁴² | R⁴³ | R⁴⁴ |
|---|---|---|---|---|---|---|
| 1 | N | H | CF₃ | H | CF₃ | H |
| 3 | N | H | Cl | H | Cl | H |
| 4 | N | H | CF₃ | H | H | H |
| 5 | N | H | H | CF₃ | H | H |

Compound 1: ¹H-NMR (CDCl₃) δ: 8.98 (1H, dd), 8.64 (2H, s), 8.58 (1H, dd), 8.17-8.11 (2H, m), 8.06 (1H, s), 7.69 (1H, dd), 3.98 (2H, q), 1.45 (3H, t).

Compound 3: ¹H-NMR (CDCl₃) δ: 8.96 (1H, d), 8.56 (1H, d), 8.09-7.98 (4H, m), 7.66 (1H, dd), 7.53 (1H, d), 3.97 (2H, q), 1.43 (3H, t).

Compound 4: ¹H-NMR (CDCl₃) δ: 8.97 (1H, dd), 8.57 (1H, dd), 8.44 (1H, s), 8.32 (1H, d), 8.11-8.05 (2H, m), 7.81 (1H, d), 7.74-7.64 (2H, m), 3.98 (2H, q), 1.44 (3H, t).

Compound 5: ¹H-NMR (CDCl₃) δ: 8.96 (1H, d), 8.57 (1H, d), 8.26 (2H, d), 8.08 (2H, s), 7.83 (2H, d), 7.67 (1H, dd), 3.98 (2H, q), 1.44 (3H, t).

Preparation Example 8

To a mixture of 1.6 m butyl lithium-hexane solution 54 mL and THF 41 mL was added dropwise a mixture of ethyl methyl sulfone 9.3 g and THF 24 ml at −78° C. To the reaction mixture was added dropwise a mixture of 5-bromo-2-cyanopyridine 12 g and THF 41 mL at −78° C. The mixture was warmed gradually to room temperature, and to the reaction mixture was added 2N hydrochloric acid, and the mixture was stirred for 30 minutes. The resulting mixture was extracted with ethyl acetate, and the resulting organic layers were washed with saturated brine. The resulting organic layers were dried over anhydrous sodium sulfate, and concentrated under reduced pressure to give an intermediate compound 6 represented by the following formula 13 g.

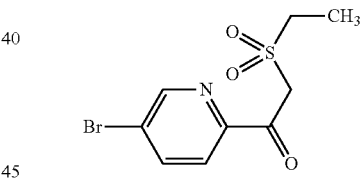

Intermediate compound 6: ¹H NMR (CDCl₃): δ 8.79 (1H, d), 8.04-7.98 (2H, m), 4.97 (2H, s), 3.28 (2H, q), 1.46 (3H, t).

Preparation Example 9

The compound that was prepared according to the similar method to the Preparation Example 8, and its physical property value is shown below.

A compound represented by formula (X-2):

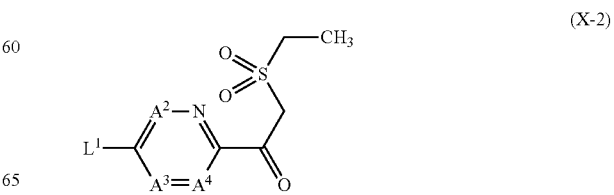

(X-2)

[wherein, each of L¹, A², A³ and A⁴ represents any group indicated in Table 19.]

TABLE 19

| Intermediate compound | L¹ | A² | A³ | A⁴ |
|---|---|---|---|---|
| 7 | Br | CH | CH | N |

Intermediate compound 7: ¹H NMR (CDCl₃): δ 9.04 (2H, s), 4.96 (2H, s), 3.29 (2H, q), 1.47 (3H, t)

Preparation Example 10

To a mixture of oxalyl chloride 8.9 mL and chloroform 68 ml was added dropwise DMF 8 ml under ice-cooling. The mixture was stirred for 30 minutes under ice-cooling, and then stirred at room temperature for 1.5 hours. The mixture was cooled in ice bath, and thereto was then added dropwise butyl vinyl ether 26 mL. The mixture was warmed to room temperature and stirred for 2 hours, and to the mixture was added dropwise a mixture of the intermediate compound 1 10 g, triethylamine 33 mL, and chloroform 23 ml under ice-cooling. The mixture was warmed to room temperature and then stirred for 1.5 hours. The resulting mixture was added to saturated aqueous ammonium chloride solution, and the mixture was extracted with chloroform. The resulting organic layers were washed with water and saturated brine, dried over anhydrous sodium sulfate, and concentrated under reduced pressure. The resulting residue was diluted with ethanol 10 mL, and thereto was added 28% ammonia water 10 mL at room temperature. The mixture was warmed to 60° C. and stirred under heating for 3 hours, and the mixture was allowed to stand to cool to room temperature, and then added to saturated aqueous sodium hydrogen carbonate solution, and the mixture was extracted with ethyl acetate. The resulting organic layers were dried over anhydrous sodium sulfate, and concentrated under reduced pressure. The resulting residue was subjected to silica gel chromatography to give an intermediate compound 8 represented by the following formula 4.5 g.

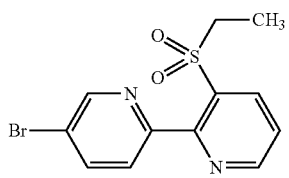 [SMILES: CCS(=O)(=O)c1cccnc1-c1ccc(Br)cn1]

Intermediate compound 8: ¹H NMR (CDCl₃): δ 8.87 (1H, dd), 8.68 (1H, d), 8.49 (1H, dd), 8.01-7.98 (m, 1H), 7.74 (1H, d), 7.56 (1H, dd), 3.86 (2H, q), 1.37 (3H, t).

Preparation Example 11

The compounds that were prepared according to the similar method to the Preparation Example 10, and their physical property values are shown below.

A compound represented by formula (X-3):

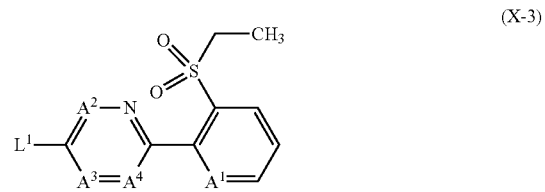

[wherein, each of L¹, A¹, A², A³ and A⁴ represents any groups indicated in Table 20].

TABLE 20

| Intermediate compound | L¹ | A¹ | A² | A³ | A⁴ |
|---|---|---|---|---|---|
| 9 | OCH₃ | N | CH | N | CH |
| 10 | Br | N | CH | CH | N |

Intermediate compound 9: ¹H-NMR (CDCl₃) δ: 8.74 (1H, dd), 8.66 (1H, dd), 8.49 (1H, d), 8.20 (1H, d), 7.55 (1H, dd), 4.05 (3H, s), 3.85 (2H, q), 1.38 (3H, t).

Intermediate compound 10: ¹H-NMR (CDCl₃) δ: 8.98 (1H, dd), 8.95 (2H, s), 8.46 (1H, dd), 7.65 (1H, dd), 3.75 (2H, q), 1.38 (3H, t).

Preparation Example 12

A mixture of the intermediate compound 8 1.3 g, 3,5-bis (trifluoromethyl)phenyl boronic acid 1.3 g, tetrakis(triphenylphosphine)palladium(0) 0.46 g, 2M aqueous sodium carbonate solution 11 mL, and toluene 40 mL was stirred under heating at 130° C. for 14 hours. The resulting reaction mixture was allowed to stand to cool to room temperature, and thereto was then added saturated aqueous sodium hydrogen carbonate solution, and the mixture was extracted with ethyl acetate. The resulting organic layers were washed with water and saturated brine, dried over sodium sulfate, and concentrated under reduced pressure. The resulting residue was subjected to silica gel chromatography to a compound 21 represented by the following formula 540 mg.

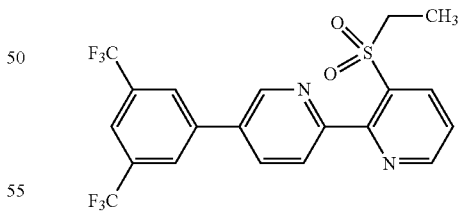

Compound 21: ¹H NMR (CDCl₃): δ 8.92 (1H, dd), 8.59 (1H, d), 8.53 (1H, dd), 8.07 (1H, brs), 7.96-7.91 (2H, m), 7.85 (1H, dd), 7.62-7.58 (2H, m), 3.90 (2H, q), 1.38 (3H, t).

Preparation Example 13

The compounds that were prepared according to the similar method to the Preparation Example 12, and their physical property values are shown below.

A compound represented by formula (X-4):

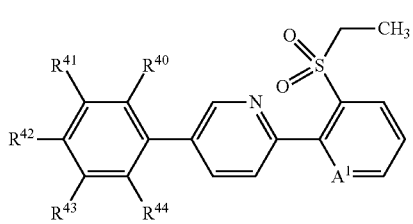

[wherein, each of $A^1$, $R^{40}$, $R^{41}$, $R^{42}$, $R^{43}$, and $R^{44}$ represents any group indicated in Table 21.]

TABLE 21

| Compound | $A^1$ | $R^{40}$ | $R^{41}$ | $R^{42}$ | $R^{43}$ | $R^{44}$ |
|---|---|---|---|---|---|---|
| 6 | N | H | H | $CF_3$ | H | H |
| 7 | N | H | $CF_3$ | H | H | H |
| 8 | N | H | $CF_3$ | Cl | H | H |
| 9 | N | $CF_3$ | H | Cl | H | H |
| 10 | N | H | Cl | H | Cl | H |
| 11 | N | H | F | H | F | H |
| 12 | N | H | F | F | F | H |
| 13 | N | H | $OCF_3$ | H | H | H |
| 14 | N | H | Cl | H | H | H |
| 15 | N | F | H | $CF_3$ | H | H |
| 20 | N | $CF_3$ | H | $CF_3$ | H | H |

Compound 6: $^1$H NMR (CDCl$_3$): δ 8.92-8.86 (2H, m), 8.52 (1H, dd), 8.08 (1H, dd), 7.97-7.95 (1H, m), 7.77 (4H, brs), 7.58 (1H, dd), 3.95 (2H, q), 1.40 (3H, t).

Compound 7: $^1$H NMR (CDCl$_3$): δ 8.92-8.86 (2H, m), 8.52 (1H, dd), 8.09 (1H, dd), 8.09 (1H, dd), 7.97 (1H, dd), 7.90-7.83 (1H, m), 7.71-7.64 (1H, m), 7.62-7.26 (2H, m), 3.96 (2H, q), 1.40 (3H, t).

Compound 8: $^1$H NMR (CDCl$_3$): δ 8.92-8.89 (1H, dd), 8.84 (1H, d), 8.52 (1H, dd), 8.05 (1H, dd), 7.96 (2H, dd), 7.75 (1H, dd), 7.65 (1H, d), 7.58 (1H, dd), 3.94 (2H, q), 1.40 (3H, t).

Compound 9: $^1$H NMR (CDCl$_3$): δ 8.92 (1H, dd), 8.57-8.51 (2H, m), 7.93-7.91 (1H, m), 7.84-7.8 (2H, m), 7.64-7.57 (2H, m), 7.39 (1H, d), 3.96 (2H, q), 1.38 (3H, t).

Compound 10: $^1$H NMR (CDCl$_3$): δ 8.90 (1H, dd), 8.84 (1H, d), 8.52 (1H, dd), 8.02 (1H, dd), 7.95 (1H, d), 7.57 (1H, dd), 7.53 (2H, d), 7.44-7.43 (1H, m), 3.93 (2H, q), 1.40 (3H, t).

Compound 11: $^1$H NMR (CDCl$_3$): δ 8.90 (1H, dd), 8.82 (1H, d), 8.52 (1H, dd), 8.03 (1H, dd), 7.95 (1H, dd), 7.55 (1H, dd), 7.18 (2H, dd), 6.91-6.86 (1H, m), 3.94 (2H, q), 1.40 (3H, t).

Compound 12: $^1$H NMR (CDCl$_3$): δ 8.90 (1H, dd), 8.78-8.77 (1H, m), 8.51 (1H, dd), 7.99-7.93 (2H, m), 7.58 (1H, dd), 7.31-7.23 (2H, m), 3.95 (2H, q), 1.39 (3H, t).

Compound 13: $^1$H NMR (CDCl$_3$): δ 8.91 (1H, dd), 8.84 (1H, dd), 8.52 (1H, dd), 8.06 (1H, dd), 7.95 (1H, dd), 7.6-7.5 (4H, m), 7.31-7.26 (1H, m), 3.96 (2H, q), 1.40 (3H, t).

Compound 14: $^1$H NMR (CDCl$_3$): δ 8.9 (1H, dd), 8.83 (1H, dd), 8.51 (1H, dd), 8.04 (1H, dd), 7.94 (1H, dd), 7.65-7.64 (1H, m), 7.59-7.52 (2H, m), 7.46-7.39 (2H, m), 3.95 (2H, q), 1.40 (3H, t).

Compound 15: $^1$H NMR (CDCl$_3$): δ 8.91 (1H, dd), 8.82 (1H, brs), 8.52 (1H, dd), 8.1-8.06 (1H, m), 7.97 (1H, d), 7.67 (1H, t), 7.61-7.48 (3H, m), 3.94 (2H, q), 1.4 (3H, t).

Compound 20: $^1$H NMR (CDCl$_3$): δ 8.92 (1H, dd), 8.59 (1H, d), 8.53 (1H, dd), 8.07 (1H, brs), 7.96-7.91 (2H, m), 7.85 (1H, dd), 7.62-7.58 (2H, m), 3.90 (2H, q), 1.38 (3H, t).

Preparation Example 14

A mixture of the intermediate compound 8 1.0 g, 5-chloro-2-(trimethylstannyl)pyridine 1.3 g, copper iodide 0.13 g, lithium chloride 0.19 g, tetrakis(triphenylphosphine)palladium(0) 0.14 g, and toluene 50 mL was stirred under heating at 110° C. for 12 hours. The resulting reaction mixture was allowed to stand to cool to room temperature, and thereto was then added saturated aqueous sodium hydrogen carbonate solution, and the mixture was extracted with ethyl acetate. The resulting organic layers were washed with water and saturated brine, dried over sodium sulfate, and concentrated under reduced pressure. The resulting residue was subjected to silica gel chromatography to give a compound 16 represented by the following formula 500 mg.

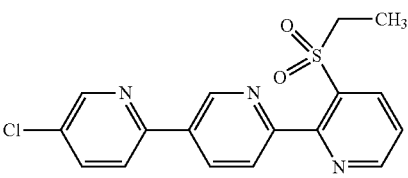 [SMILES: CCS(=O)(=O)c1cccnc1-c1ccc(-c2ccc(Cl)cn2)cn1]

Compound 16: $^1$H NMR (CDCl$_3$): δ 9.24 (1H, d), 8.9 (1H, dd), 8.7 (1H, d), 8.51 (1H, dd), 8.45 (1H, dd), 7.96 (1H, d), 7.79 (2H, d), 7.57 (1H, dd), 3.94 (2H, q), 1.39 (3H, t).

Preparation Example 15

The compounds that were prepared according to the similar method to the Preparation Example 14, and their physical property values are shown below.

A compound represented by formula (X-5):

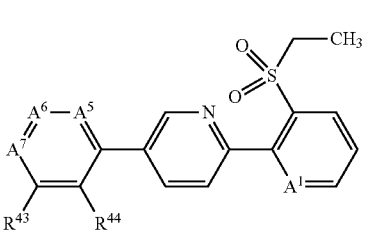

[wherein, each of $A^1$, $A^5$, $A^6$, $A^7$, $R^{43}$, and $R^{44}$ represents any group indicated in Table 22].

TABLE 22

| Compound | $A^1$ | $A^5$ | $A^6$ | $A^7$ | $R^{43}$ | $R^{44}$ |
|---|---|---|---|---|---|---|
| 17 | N | CH | N | CCl | H | H |
| 18 | N | CH | CCl | N | H | H |
| 19 | N | CH | CCl | N | Cl | H |

Compound 17: $^1$H NMR (DMSO-d6): δ 9.07 (1H, d), 8.99 (1H, dd), 8.92 (1H, d), 8.47 (1H, dd), 8.4-8.35 (2H, m), 7.93 (1H, d), 7.82-7.79 (1H, m), 7.70 (1H, d), 3.95 (2H, q), 1.26 (3H, t).

Compound 18: $^1$H NMR (CDCl$_3$): δ 8.91 (2H, dd), 8.88 (1H, dd), 8.50 (1H, dd), 8.10 (1H, dd), 7.99 (1H, dd), 7.63-7.59 (2H, m), 7.51 (1H, dd), 3.92 (2H, q), 1.40 (3H, t).

Compound 19: ¹H NMR (CDCl₃): δ 8.92-8.86 (2H, m), 8.52 (1H, d), 8.08 (1H, dd), 8.01 (1H, d), 7.62-7.55 (1H, m), 7.59 (2H, s), 3.92 (2H, q), 1.40 (3H, t).

Preparation Example 16

A mixture of methyl 5-chloro-2-pyradine carboxylate 10 g, sodium methoxide (28% methanol solution) 28 mL, and THF 100 mL was stirred for 3 hours under ice-cooling. To the resulting reaction mixture was added ethyl methyl sulfone 18 mL under ice-cooling. The reaction mixture was warmed to 80° C., and stirred under heating for 24 hours. The resulting reaction mixture was allowed to stand to cool to room temperature, and thereto was then added 2N hydrochloric acid, and the mixture was extracted with ethyl acetate. The resulting organic layers were dried over anhydrous sodium sulfate, and concentrated. The resulting residue was subjected to silica gel chromatography to give an intermediate compound 11 represented by the following formula 11 g.

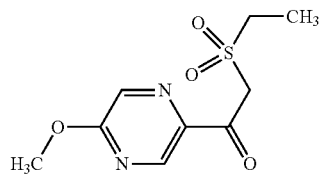 [SMILES: CCS(=O)(=O)CC(=O)c1cnc(OC)cn1]

Intermediate compound 11: ¹H-NMR (CDCl₃) δ: 8.91 (1H, d), 8.25 (1H, d), 4.87 (2H, s), 4.08 (3H, s), 3.29 (2H, q), 1.47 (3H, t).

Preparation Example 17

A mixture of the intermediate compound 9 4.5 g, and 12 N hydrochloric acid 20 mL was stirred under heating at 100° C. for 1 hour. The reaction mixture was allowed to stand to cool to room temperature, and thereto was then added ice water 100 mL. The mixture was alkalified by adding saturated aqueous sodium hydrogen carbonate solution, and the mixture was extracted with ethyl acetate. The resulting organic layers were dried over anhydrous sodium sulfate, and concentrated under reduced pressure. The resulting residue was subjected to silica gel chromatography to give an intermediate compound 12 represented by the following formula 4.3 g.

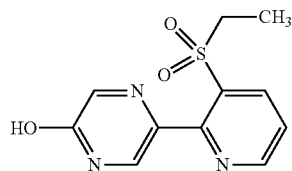 [SMILES: CCS(=O)(=O)c1cccnc1-c1cnc(O)cn1]

Intermediate compound 12: ¹H-NMR (CDCl₃) δ: 8.81 (1H, dd), 8.47 (1H, dd), 8.21 (1H, d), 7.97 (1H, d), 7.52 (1H, dd), 3.83 (2H, q), 1.39 (3H, t).

Preparation Example 18

A mixture of the intermediate compound 12 4.3 g, phosphorus oxychloride 12 mL, and toluene 60 ml was stirred under heating at 100° C. for 2 hours. The resulting reaction mixture was allowed to stand to cool to room temperature, and then concentrated under reduced pressure. To the resulting residue was added water, and the mixture was extracted with chloroform. The resulting organic layers were dried over anhydrous sodium sulfate, and concentrated under reduced pressure to give an intermediate compound 13 represented by the following formula 4.6 g.

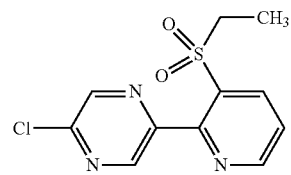 [SMILES: CCS(=O)(=O)c1cccnc1-c1cnc(Cl)cn1]

Intermediate compound 13: ¹H-NMR (CDCl₃) δ: 8.94 (1H, dd), 8.90 (1H, dd), 8.59 (1H, d), 8.52 (1H, d), 7.65 (1H, dd), 3.81 (2H, q), 1.39 (3H, t).

Preparation Example 19

To a mixture of the intermediate compound 2.0 g, and toluene 8 mL were added one drop of DMF and phosphorus oxybromide 4.3 g successively at room temperature. The mixture was stirred at 100° C. for 9 hours. The resulting mixture was allowed to stand to cool to room temperature, and there was then added water, and the mixture was extracted with ethyl acetate. The resulting organic layers were washed with water and saturated brine successively, dried over sodium sulfate, and concentrated under reduced pressure. The resulting residue was subjected to silica gel chromatography to give an intermediate compound 14 represented by the following formula 2.1 g.

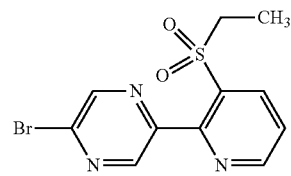 [SMILES: CCS(=O)(=O)c1cccnc1-c1cnc(Br)cn1]

Intermediate compound 14: ¹H-NMR (CDCl₃) δ: 8.91 (1H, d), 8.87 (1H, s), 8.67 (1H, s), 8.50 (1H, d), 7.62 (1H, q), 3.78 (2H, q), 1.37 (3H, t).

Preparation Example 20

A mixture of the intermediate compound 14 1.0 g, 3,5-bis(trifluoromethyl)phenyl boronic acid 1.04 g, dichloro[1,1'-bis(diphenylphosphino)ferrocene]palladium(II) dichloromethane adduct 0.22 g, sodium carbonate 0.96 g, DME 15 mL, and water 3 mL was stirred at 80° C. under argon atmosphere for 16 hours. The resulting mixture was allowed to cool to room temperature, and thereto was then added saturated aqueous sodium hydrogen carbonate solution, and the mixture was extracted with ethyl acetate. The resulting organic layers were washed with water and saturated brine successively, dried over sodium sulfate, and concentrated under reduced pressure. The resulting residue was subjected to silica gel chromatography to give a compound 22 represented by the following formula 460 mg.

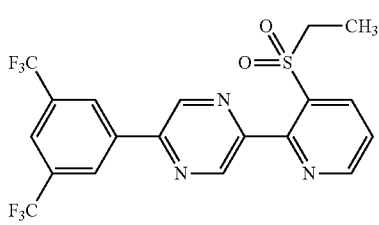 [SMILES: CCS(=O)(=O)c1cccnc1-c1cnc(-c2cc(C(F)(F)F)cc(C(F)(F)F)c2)cn1]

Compound 22: ¹H NMR (CDCl₃) δ 1.42 (3H, t), 3.89 (2H, q), 7.65 (1H, dd), 8.00 (1H, s), 8.54 (1H, d), 8.59 (2H, s), 8.97 (1H, d), 9.11 (1H, s), 9.22 (1H, s).

Preparation Example 21

The compounds that were prepared according to the similar method to the Preparation Example 20, and their physical property values are shown below.

A compound represented by formula (X-5):

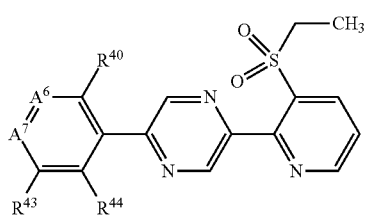

[wherein, each of $A^6$, $A^7$, $R^{40}$, $R^{43}$, and $R^{44}$ represents any group indicated in Table 23].

TABLE 23

| Compound | $A^6$ | $A^7$ | $R^{40}$ | $R^{43}$ | $R^{44}$ |
|---|---|---|---|---|---|
| 23 | CH | CH | H | CF₃ | H |
| 24 | CH | CCF₃ | H | H | H |
| 25 | N | CH | H | CF₃ | H |
| 26 | N | CCF₃ | H | H | H |
| 27 | CH | N | H | CF₃ | H |
| 28 | CH | CH | H | OCF₃ | H |
| 29 | CH | C(OCF₃) | H | H | H |

Compound 23: ¹H NMR (CDCl₃) δ 1.41 (3H, t), 3.91 (2H, q), 7.61-7.70 (2H, m), 7.76 (1H, d), 8.30 (1H, d), 8.38 (1H, s), 8.50-8.57 (1H, m), 8.92-8.99 (1H, m), 9.03-9.09 (1H, m), 9.16-9.22 (1H, m).

Compound 24: ¹H NMR (CDCl₃) δ 1.41 (3H, t), 3.90 (2H, q), 7.63 (1H, dd), 7.79 (2H, d), 8.22 (2H, d), 8.54 (1H, d), 8.96 (1H, d), 9.05 (1H, s), 9.19 (1H, s).

Compound 25: ¹H NMR (CDCl₃) δ 1.42 (3H, t), 3.89 (2H, q), 7.65 (1H, dd), 8.54 (1H, dd), 8.70 (1H, s), 8.95-8.98 (1H, m), 9.01 (1H, s), 9.11 (1H, d), 9.22 (1H, d), 9.51 (1H, s).

Compound 26: ¹H NMR (CDCl₃) δ 1.42 (3H, t), 3.89 (2H, q), 7.65 (1H, dd), 7.87 (1H, d), 8.54 (1H, dd), 8.62 (1H, d), 8.97 (1H, dd), 9.09 (1H, d), 9.23 (1H, d), 9.41 (1H, s)

Compound 27: ¹H NMR (CDCl₃) δ 1.42 (3H, t), 3.88 (2H, q), 7.64-7.67 (1H, m), 8.20 (1H, d), 8.41 (1H, s), 8.53 (1H, d), 8.92 (1H, d), 8.97 (1H, d), 9.13 (1H, s), 9.23 (1H, s).

Compound 28: ¹H NMR (CDCl₃) δ 1.42 (3H, t), 3.90 (2H, q), 7.35 (1H, d), 7.57 (1H, t), 7.62-7.64 (1H, m), 7.99 (1H, s), 8.03 (1H, d), 8.52 (1H, d), 8.95 (1H, d), 9.01 (1H, s), 9.17 (1H, s).

Compound 29: ¹H NMR (CDCl₃) δ 1.40 (3H, t), 3.90 (2H, q), 7.37 (2H, d), 7.58-7.63 (1H, m), 8.14 (2H, d), 8.53 (1H, d), 8.95 (1H, d), 9.00 (1H, s), 9.16 (1H, s).

Preparation Example 22

A mixture of the intermediate compound 14 0.8 g, lithium trihydroxy[4-(trifluoromethyl)pyridin-2-yl]borate 1.04 g, copper(I) chloride 24 mg, zinc chloride 322 mg, dichloro [1,1′-bis(diphenylphoshino)ferrocene]palladium(II) dichloromethane adduct 178 mg, cesium carbonate 1.58 g, and DMF 15 mL was stirred at 100° C. under argon atmosphere for 16 hours. The resulting mixture was allowed to stand to cool to room temperature, and the mixture was then extracted with ethyl acetate. The resulting organic layers were washed with water and saturated brine successively, dried over sodium sulfate, and concentrated under reduced pressure. The resulting residue was subjected to silica gel chromatography to give a compound 30 represented by the following formula 250 mg.

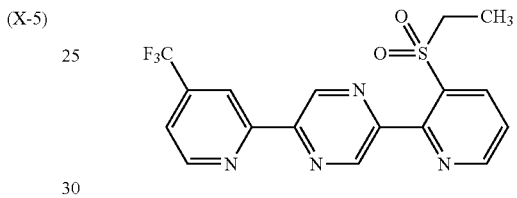

Compound 30: ¹H NMR (CDCl₃) δ 1.40 (3H, t), 3.89 (2H, q), 7.61-7.64 (2H, m), 8.53 (1H, d), 8.72 (1H, s), 8.87-8.96 (2H, m), 9.15 (1H, s), 9.67 (1H, s).

Preparation Example 15

The compound that was prepared according to the similar method to the Preparation Example 22, and its physical property value is shown below.

A compound represented by formula (X-6):

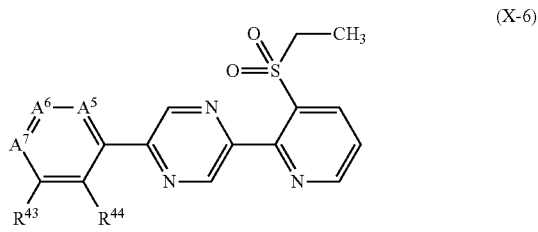

[wherein, each of $A^5$, $A^6$, $A^7$, $R^{43}$, and $R^{44}$ represents any group indicated in Table 24.]

TABLE 24

| Compound | $A^5$ | $A^6$ | $A^7$ | $R^{43}$ | $R^{44}$ |
|---|---|---|---|---|---|
| 31 | N | CCF₃ | CH | H | H |

Compound 31: ¹H NMR (CDCl₃) δ 1.28 (3H, t), 3.92 (2H, q), 7.61-7.64 (1H, m), 7.76 (1H, d), 8.05 (1H, t), 8.53 (1H, d), 8.66 (1H, d), 8.94 (1H, d), 9.14 (1H, s), 9.71 (1H, s).

Next, the formulation examples of the compound of the present invention are shown below. The "parts" represents "part by weight" unless otherwise specified.

Formulation Example 1

Into a mixture of 35 parts of xylene and 35 parts of DMF, 10 parts of any one of the compounds 1 to 31 is dissolved, and then 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of synthetic hydrated silicon oxide fine powder and 54 parts of diatomaceous earth are mixed, and further 20 parts of any one of the compounds 1 to 31 is added, followed by mixing them to obtain each wettable powders.

Formulation Example 3

To 2 parts of any one of the compounds 1 to 31, 1 part of synthetic hydrated silicon oxide fine powder, 2 parts of calcium lignin sulfonate, 30 parts of bentonite and 65 parts of kaolin clay are added, followed by mixing, granulation with a granulator and forced-air drying to obtain each granular formulation.

Formulation Example 4

Into an appropriate amount of acetone, 1 part of any one of the compounds 1 to 31 is mixed, and then 5 parts of synthetic hydrous silicon oxide fine powder, 0.3 parts of isopropyl acid phosphate and 93.7 parts of kaolin clay are added, followed by mixing with stirring thoroughly and removal of acetone from the mixture by evaporation to obtain each of powder formulation.

Formulation Example 5

A mixture of 35 parts of polyoxyethylene alkyl ether sulfate ammonium salt and white carbon (weight ratio of 1:1), 20 parts of any one of the compounds 1 to 31, and 45 parts of water are mixed, followed by finely grounding by a wet grinding method to obtain each flowable formulation.

Formulation Example 6

Into a mixture of 5 parts of xylene and 5 parts of trichloroethane, 0.1 parts of any one of the compounds 1 to 31 is dissolved, and the resulting mixture is then mixed with 89.9 parts of kerosene to obtain each oil solution.

Formulation Example 7

Into 0.5 mL of acetone, 10 mg of any one of the compounds 1 to 31 is dissolved and the solution is added dropwise to 5 g of a solid feed powder for an animal (solid feed powder for rearing and breeding CE-2, manufactured by CLEA Japan, Inc.), followed by mixing the resulting mixture uniformly, and then by drying them by evaporation of acetone to obtain each poison bait.

Formulation Example 8

Into an aerosol can, 0.1 part of any one of the compounds 1 to 31 and 49.9 parts of Neothiozole (Chuo Kasei Co., Ltd.) are placed. After mounting an aerosol valve, 25 parts of dimethylether and 25 parts of LPG are filled, followed by shaking and further mounting an actuator to obtain an oily aerosol.

Formulation Example 9

A mixture of 0.6 part of any one of the compounds 1 to 31, 0.01 part of BHT (2,6-di-tert-butyl-4-methylphenol), 5 parts of xylene, 3.39 parts of deodorized kerosine and 1 part of an emulsifier {Rheodol MO-60 (registered trademark of Kao Corporation)} and 50 parts of distilled water are filled into an aerosol container, and a valve part is attached. Then, 40 parts of a propellant (LPG) is filled therein through the valve under pressure to obtain an aqueous aerosol.

Formulation Example 10

Zero point one (0.1) parts of any one of the compounds 1 to 31 are mixed into 2 mL of propylene glycol, and the resulting solution is impregnated into a ceramic plate having a size of 4.0 cm×4.0 cm and a thickness of 1.2 cm, to obtain thermal fumigants.

Formulation Example 11

Five (5) parts of any one of the compounds 1 to 31, and 95 parts of ethylene-methyl methacrylate copolymer (the ratio of the methyl methacrylate in the copolymer: 10 weight %), Acryft (registered by trademark) WD 301, manufactured by Sumitomo Chemical Co. Ltd.) are melted and kneaded with a closed type pressure kneader (manufactured by Moriyama Manufacturing Co. Ltd.), and the resulting kneaded product is extruded from an extrusion molding machine through a molding die to obtain a rod-shaped molded product having a length of 15 cm and a diameter of 3 mm.

Formulation Example 12

Five (5) parts of any one of the compounds 1 to 31, and 95 parts of plasticized polyvinyl chloride resin are melted and kneaded with a closed type pressure kneader (manufactured by Moriyama Manufacturing Co. Ltd.), and the resulting kneaded product is extruded from an extrusion molding machine through a molding die to obtain a rod-shaped molded product having a length of 15 cm and a diameter of 3 mm.

Formulation Example 13

One hundred (100) mg of any one of the compounds 1 to 31, 68.75 mg of lactose, 237.5 mg of corn starch, 43.75 mg of microcrystalline cellulose, 18.75 mg of polyvinylpyrrolidone, 28.75 mg of sodium carbomethyl starch and 2.5 mg of magnesium stearate are mixed, and the resulting mixture was compressed to an appropriate size to obtain a tablet.

Formulation Example 14

Twenty five (25) mg of any one of the compounds 1 to 31, 60 mg of lactose, 25 mg of corn starch, 6 mg of carmellose calcium and an appropriate amount of 5% of hydroxypropyl methylcellulose are mixed, and the resulting mixture are filled into a hard shell gelatin capsule or a hydroxypropyl methylcellulose capsule to obtain capsules.

Formulation Example 15

To 100 mg of any one of the compounds 1 to 31, 500 mg of fumaric acid, 2000 mg of sodium chloride, 150 mg of methyl paraben, 50 mg of propyl paraben, 25000 mg of granulated sugar, 13,000 mg of sorbitol (70% solution), 100 mg of Veegum K (manufactured by Vanderbilt Co.), 35 mg of perfume and 500 mg of coloring agent, a distilled water is added so that a final volume is set to be 100 mL, followed by mixing them to obtain a suspension for oral administration.

Formulation Example 16

Into a mixture of 5% by weight of an emulsifier, 3% by weight of benzyl alcohol and 30% by weight of propylene glycol, 5% by weight of any one of the compounds 1 to 31 is dissolved, and phosphate buffer is added thereto so that a pH of the solution is set to be 6.0 to 6.5, and water is added as the rest parts to obtain the solution for oral administration.

Formulation Example 17

To a mixture of 57% by weight of fractional distilled palm oil and 3% by weight of polysorbate 85, 5% by weight of aluminum distearate is added, and heated to disperse it. The resulting mixture is cooled to room temperature, and 25% by weight of saccharin is dispersed in an oil vehicle. Ten (10) % by weight of any one of the compounds 1 to 31 is divided thereto to obtain a paste for oral administration.

Formulation Example 18

Five (5) % by weight of any one of the compounds 1 to 31 is mixed with 95% by weight of limestone filler, followed by a wet granulation of the resulting mixture to obtain a granule for oral administration.

Formulation Example 19

Into 80 parts of diethylene glycol monomethyl ether, 5 parts of any one of the compounds 1 to 31 is dissolved, and 15 parts of propylene carbonate is added thereto, and the resulting mixture is mixed to obtain a spot-on solution.

Formulation Example 20

Into 70 parts of diethylene glycol monomethyl ether, 10 parts of any one of the compounds 1 to 31 is dissolved, and 20 parts of 2-octyldodecanol is added thereto, and the resulting mixture is mixed to obtain a pour-on solution.

Formulation Example 21

To 0.5 parts of any one of the compounds 1 to 31, 60 parts of Nikkol (registered by trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly, and 19.5 parts of water is then added thereto and the resulting mixture is further mixed with stirring thoroughly to obtain a hydrogenous solution of shampoo formulation.

Formulation Example 22

Zero point fifteen (0.15) % by weight of any one of the compounds 1 to 31, 95% by weight of animal feed, as well as 4.85% by weight of a mixture of dibasic calcium phosphate, diatomaceous earth, aerosol and carbonate (or chalk) are mixed with stirring thoroughly to obtain a premix for animal feed.

Formulation Example 23

Seven point two (7.2) g of any one of the compounds 1 to 31, and 92.8 g of Hosco (registered trademark) S-55 (manufactured by Maruishi Pharmaceuticals) are melted and mixed at 100° C., and the resulting mixture was poured into a suppository mold, followed by performing a cooling solidification to obtain a suppository.

Next, Test Examples are used to show an efficacy of the Present compound on controlling harmful arthropods.

The following test examples were carried out at 25° C.

Test Example 1

The test compounds are made to a formulation according to a similar method to that described in the Formulation Example 5, and thereto is added water containing 0.03 v/v % of a spreader to prepare a diluted solution containing a prescribed concentration of the test compound.

Cucumber (*Cucumis sativus*) seedling (on the developmental stage of the second true leaf) is planted in a container and approximately 30 cotton aphids (*Aphis gossypii*) (all stages of life) are released onto the leaves of the cucumber. After 1 day, the diluted solutions are sprayed into the seedling in a ratio of 10 mL/seedling. After 5 days, the number of the surviving insects is examined and the controlling value is calculated by the following equation.

$$\text{Controlling value (\%)} = \{1-(Cb \times Tai)/(Cai \times Tb)\} \times 100$$

wherein the symbols in the formula represent the following descriptions.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where the similar treatment procedure to that of the treated group except not using the test compound is done.

The test was conducted by making the prescribed concentration 500 ppm and using the below-mentioned compounds as a test compound according to the test example 1. As a result of the test, the below-mentioned compounds showed 90% or greater as the controlling value.

Compound number: 1, 2, 4, 5, 7, 9, 10, 11, 12, 13, 16, 17, 19, 21, 22, 23, 24, 25, 26, 27, 28, 29 and 31

Test Example 2

The test compounds are made to a formulation according to a similar method to that described in the Formulation Example 5, and thereto is added water containing 0.03 v/v % of a spreader to prepare a diluted solution containing a prescribed concentration of the test compound.

Rice (*Oryza sativa*) seedling (on the developmental stage of the second true leaf) is planted in a container, and the diluted solutions are sprayed into the seedling in a ratio of 10 mL/seedling. Thereafter, 20 3rd instar larvae of brown planthopper (*Nilaparvata lugens*) are released onto the rice leaves. After 6 days, the number of the surviving insects is examined, and the morality of insects is calculated by the following equation.

Morality (%)={1−the number of the surviving insects/20}×100

The test was conducted by making the prescribed concentration 500 ppm and using the below-mentioned compounds as a test compound according to the test example 2. As a result of the test, the below-mentioned compounds showed 90% or greater as the morality.

Compound number: 7, 11, 18, 23, 25, and 26

Test Example 3

The test compounds are made to a formulation according to a similar method to that described in the Formulation Example 5, and thereto is added water to prepare a diluted solution containing a prescribed concentration of the test compound.

In a container, 7.7 g of artificial diet (Insecta LF, manufactured by NOSAN CORPORATION) is placed, and 2 mL of the diluted solution is irrigated thereto. Five (5) fourth instar larvae of tobacco cutworm (*Spodoptera litura*) are released onto the artificial diet. After 5 days, the number of the surviving insects is examined, and the morality of insects is calculated by the following equation.

Morality (%)={1−the number of the surviving insects/5}×100

The test was conducted by making the prescribed concentration 500 ppm and using the below-mentioned compounds as a test compound according to the test example 3. As a result of the test, the below-mentioned compounds showed 80% or greater as the morality.

Compound number: 1, 10 and 22

Test Example 4

The test compounds are made to a formulation according to a similar method to that described in the Formulation Example 5, and thereto is added water to prepare a diluted solution containing a prescribed concentration of the test compound.

The diluted solutions are sprayed into the cabbage (*Brassicae oleracea*) seedling (on the developmental stage of the second to third true leaf) that is planted in a container in a ratio of 20 mL/seedling. Thereafter, the stem and leaf thereof is cut out and then is installed into the container that is covered with the filter paper. Five (5) cabbage moth (*Plutella xylostella*) at the second instar larval stages are released into the cup. After 5 days, the number of the surviving insects is counted, and the mortality of insects is calculated by the following equation.

Morality (%)={1−the number of the surviving insects/5}×100

The test was conducted by making the prescribed concentration 500 ppm and using the below-mentioned compounds as a test compound according to the test example 4. As a result of the test, the below-mentioned compounds showed 80% or greater as the morality.

Compound number: 1, 3, 4, 5, 6, 7, 8, 10, 11, 12, 13, 14, 15, 16, 17, 18, 19, 22, 23, 24, 25, 26, 27, 30, and 31

Test Example 5

The test compounds are dissolved into a mixed solution of polyoxyethylene sorbitan mono-cocoate and acetone (acetone and polyoxyethylene sorbitan mono-cocoate=5:95 (v/v ratio)) in a ratio of 50 μL of the mixed solution per 1 mg of the test compound. Thereto is added water containing 0.03% by volume of a spreader to prepare a diluted solution containing a prescribed concentration of the test compound.

Corns (*Zea mays*) are sown on a tray overlaid with damped KimWipes (registered trademark). After corns were grown for 5 days, the entire seedling of the corn is immersed into the diluted solution for 30 seconds. Thereafter, each two grains of the seedling are installed in a plastic petri dish (90 mm radius), and 10 western corn rootworms (*Diabrotica virgifera virgifera*) at the second instar larval stages are released onto the cup. After 5 days, the number of the died insects is counted, and the mortality of insects is calculated by the following equation.

Morality (%)={1−the number of the surviving insects/10}×100

The test was conducted by making the prescribed concentration 500 ppm and using the below-mentioned compounds as a test compound according to the test example 5. As a result of the test, the below-mentioned compounds showed 80% or greater as the morality.

Compound number: 1, 6, 7, 8, 10, 12, 13, 21, 22, 23, 24, 25, 26, and 31

Test Example 6

The test compounds are dissolved into a mixed solution of xylene, DMF and surfactants (xylene, DMF and surfactants=4:4:1 (v/v ratio)) in a ratio of 10 μL of the mixed solution per 1 mg of the test compound. Thereto is added water containing 0.03% by volume of a spreader to prepare a diluted solution containing a prescribed concentration of the test compound.

The diluted solutions are sprayed into the cucumber seedling (*Cucumis Sativus*) (on the developmental stage of the second to third true leaf) that is planted in the container in a ratio of 10 mL/seedling. Thereafter, the second leaf is cut out, and then installed into the polyethylene cup, and 10 cucurbit leaf beetles (*Aulacophora femoralis*) at the second instar larval stages are released into the container. After 5 days, the number of died insects is counted, and the mortality of insects is calculated by the following equation.

Mortality of insects (%)=(Number of dead insects/10)×100

The test was conducted by making the prescribed concentration 500 ppm and using the below-mentioned compounds as a test compound according to the test example 6. As a result of the test, the below-mentioned compounds showed 80% or greater as the morality.

Compound number: 4 and 5

Test Example 7

The test compounds are made to a formulation according to a similar method to that described in the Formulation Example 5, and thereto is added water to prepare a diluted solution containing a prescribed concentration of the test compound.

The container is matted with a filter paper having 5.5 cm diameter, and 30 mg sucrose is placed on the filter paper, and 0.7 mL of the diluted solution is added dropwise to the filter paper. Ten (10) female adult houseflies (*Musca domestica*) are released into the container. After 24 hours, the number of died insects is counted, and the mortality of insects is calculated by the following equation.

Mortality of insects (%)=(Number of dead insects/Number of test insects)×100

The test was conducted by making the prescribed concentration 500 ppm and using the below-mentioned compounds as a test compound according to the test example 7. As a result of the test, the below-mentioned compounds showed 100% as the morality.

Compound number: 3, 4, and 5

INDUSTRIAL APPLICABILITY

The Present compound shows an excellent control effect against a harmful arthropod.

The invention claimed is:
1. A compound represented by formula (I):

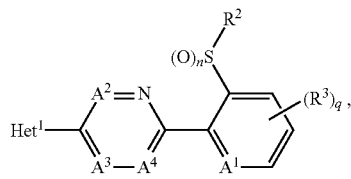

or an N-oxide compound thereof,
wherein
Het$^1$ represents Het$^1$-1:

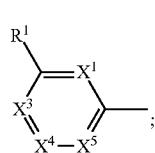

R$^1$ represents OR$^4$, OS(O)$_2$R$^4$, S(O)$_m$R$^4$, NR$^5$S(O)$_2$R$^4$, a C1-C4 chain hydrocarbon group having one or more halogen atoms, or a halogen atom;
R$^4$ represents a C1-C4 chain hydrocarbon group having one or more halogen atoms;
R$^5$ represents a hydrogen atom, or a C1-C6 chain hydrocarbon group optionally having one or more halogen atoms;
X$^1$ represents CR$^{30}$;
X$^3$ represents CR$^{32}$;
X$^4$ represents CR$^{33}$;
X$^5$ represents CR$^{34}$;
R$^{30}$, R$^{32}$, R$^{33}$, and R$^{34}$ represent independently of each other a hydrogen atom, a C1-C6 chain hydrocarbon group optionally having one or more halogen atoms, a C3-C6 alicyclic group optionally having one or more halogen atoms, or a halogen atom,
A$^1$ represents a nitrogen atom;
A$^2$ represents a nitrogen atom, A$^3$ represents CR$^7$, and A$^4$ represents CR$^8$;
R$^7$ and R$^8$ represent independently of each other a hydrogen atom, a C1-C6 chain hydrocarbon group optionally having one or more halogen atoms, a nitro group, OR$^{18}$, NR$^{18}$R$^{19}$, a cyano group, or a halogen atom;
n is 0, 1, or 2;
R$^2$ represents a cyclopropyl group, a cyclopropylmethyl group, or a C1-C6 alkyl group optionally having one or more halogen atoms;
q is 0, 1, 2, or 3;
R$^3$ represents a C1-C6 chain hydrocarbon group optionally having one or more substituents selected from Group B, a phenyl group optionally having one or more substituents selected from Group D, a nitro group, OR$^{12}$, NR$^{11}$R$^{12}$, NR$^{24}$NR$^{11}$R$^{12}$, NR$^{24}$OR$^{11}$, NR$^{11}$C(O)R$^{13}$, NR$^{24}$NR$^{11}$C(O)R$^{13}$, NR$^{11}$C(O)OR$^{14}$, NR$^{24}$NR$^{11}$C(O)OR$^{14}$, NR$^{11}$C(O)NR$^{15}$R$^{16}$, NR$^{24}$NR$^{11}$C(O)NR$^{15}$R$^{16}$, N=CHNR$^{15}$R$^{16}$, N=S(O)$_x$R$^{15}$R$^{16}$, S(O)$_y$R$^{15}$, C(O)OR$^{17}$, C(O)NR$^{11}$R$^{12}$, a cyano group, or a halogen atom, and when q is 2 or 3, two or more R$^3$ is identical to or different from each other;
R$^{11}$, R$^{17}$, R$^{18}$, R$^{19}$ and R$^{24}$ represent independently of each other a hydrogen atom, or a C1-C6 chain hydrocarbon group optionally having one or more halogen atoms;
R$^{12}$ represents a hydrogen atom, S(O)$_2$R$^{23}$, a C1-C6 chain hydrocarbon group optionally having one or more halogen atoms, or a C1-C6 alkyl group having one substituent selected from Group F;
R$^{23}$ represents a C1-C6 chain hydrocarbon group optionally having one or more halogen atoms, or a phenyl group optionally having one or more substituents selected from Group D;
R$^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl) C1-C3 alkyl group optionally having one or more halogen atoms, or a phenyl group optionally having one or more substituents selected from Group D;
R$^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group, wherein the phenyl moiety of the phenyl C1-C3 alkyl group may optionally have one or more substituents selected from Group D;
m is 0, 1, or 2;
x is 0 or 1;
y is 0, 1, or 2;
Group B is selected from the group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom;
Group D is selected from the group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, $NHR^{21}$, $NR^{21}R^{22}$, $C(O)R^{21}$, $OC(O)R^{21}$, $C(O)OR^{21}$, a cyano group, a nitro group, and a halogen atom, wherein said $R^{21}$ and $R^{22}$ represent independently of each other a C1-C6 alkyl group optionally having one or more halogen atoms.

2. The compound according to claim 1, wherein $R^3$ represents a C1-C6 alkyl group optionally having one or more halogen atoms, a phenyl group optionally having one or more substituents selected from Group G, $NR^{11}R^{12}$, $NR^{24}NR^{11}R^{12}$ or a halogen atom, wherein Group G is selected from the group consisting of a halogen atom and a C1-C6 haloalkyl group.

3. The compound according to claim 1, wherein $R^3$ represents a C1-C6 alkyl group optionally having one or more halogen atoms, or a halogen atom.

4. The compound according to claim 1, wherein $R^2$ represents an ethyl group.

5. The compound according to claim 1, wherein $R^1$ represents a C1-C4 chain hydrocarbon group having one or more halogen atoms, or a halogen atom; $R^2$ represents a methyl group, or an ethyl group; and $R^3$ represents a C1-C6 alkyl group optionally having one or more halogen atoms, a phenyl group optionally having one or more substituents selected from Group G, $NR^{11}R^{12}$, $NR^{24}NR^{11}R^{12}$, or a halogen atom; $R^{11}$, $R^{12}$ and $R^{24}$ represent independently of each other a hydrogen atom, a C1-C3 alkyl group optionally having one or more halogen atoms; $R^7$ and $R^8$ represent independently of each other a C1-C6 alkyl group optionally having one or more halogen atoms, a halogen atom; and q is 0 or 1;

wherein Group G is selected from the group consisting of a halogen atom and a C1-C6 haloalkyl group.

6. The compound according to claim 1, wherein $R^1$ represents a C1-C4 chain hydrocarbon group having one or more halogen atoms, or a halogen atom; $R^2$ represents a methyl group, or an ethyl group; $R^3$ represents a C1-C6 alkyl group optionally having one or more halogen atoms, a phenyl group optionally having one or more substituents selected from Group G, $NR^{11}R^{12}$, $NR^{24}NR^{11}R^{12}$, or a halogen atom; $R^{11}$, $R^{12}$, and $R^{24}$ represent independently of each other a hydrogen atom, a C1-C3 alkyl group optionally having one or more halogen atoms; $R^7$ and $R^8$ represent independently of each other a hydrogen atom, a C1-C6 alkyl group optionally having one or more halogen atoms, or a halogen atom; and q is 0 or 1;

wherein Group G is selected from the group consisting of a halogen atom and a C1-C6 haloalkyl group.

7. The compound according to claim 1, wherein $R^1$ represents a C1-C4 chain hydrocarbon group having one or more halogen atoms, or a halogen atom; $R^2$ represents an ethyl group; q is 0 or 1; and $R^3$ represents a C1-C6 alkyl group optionally having one or more halogen atoms, or a halogen atom.

8. A composition for controlling a harmful arthropod comprising the compound according to claim 1 and an inert carrier.

9. The compound according to claim 1, wherein $R^1$ is a C1-C4 chain hydrocarbon group having one or more halogen atoms, or a halogen atom; $X^1$ is CH, $X^3$ is $CR^{32}$, $X^4$ is $CR^{33}$, and $X^5$ is CH; $R^2$ is an ethyl group; and $R^3$ is a C1-C6 alkyl group optionally having one or more halogen atoms, or a halogen atom.

10. A composition for controlling a harmful arthropod comprising the compound according to claim 9 and an inert carrier.

* * * * *